US009764045B2

(12) United States Patent
Nathwani et al.

(10) Patent No.: US 9,764,045 B2
(45) Date of Patent: *Sep. 19, 2017

(54) OPTIMISED CODING SEQUENCE AND PROMOTER

(71) Applicants: UCL BUSINESS PLC, London (GB); THROMBOSIS RESEARCH INSTITUTE, Chelsea (GB); ST. JUDE CHILDREN'S RESEARCH HOSPITAL, Memphis, TN (US)

(72) Inventors: Amit Nathwani, London (GB); Natalie Ward, London (GB); Adrian Thrasher, London (GB); Edward Tuddenham, London (GB); John Mcvey, London (GB); John Gray, Memphis, TN (US); Andrew Davidoff, Memphis, TN (US)

(73) Assignees: UCL BUSINESS PLC, London (GB); THROMBOSIS RESEARCH INSTITUTE, London (GB); ST. JUDE CHILDREN'S RESEARCH HOSPITAL, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/680,836

(22) Filed: Apr. 7, 2015

(65) Prior Publication Data

US 2015/0273082 A1    Oct. 1, 2015

Related U.S. Application Data

(62) Division of application No. 13/382,953, filed as application No. PCT/US2010/041378 on Jul. 8, 2010, now Pat. No. 9,393,323.

(30) Foreign Application Priority Data

Jul. 8, 2009    (GB) .................................. 0911870.4

(51) Int. Cl.
| | | |
|---|---|---|
| C07H 21/04 | (2006.01) | |
| C12N 15/63 | (2006.01) | |
| A61K 48/00 | (2006.01) | |
| C07K 14/755 | (2006.01) | |
| C12N 15/86 | (2006.01) | |
| A61K 38/37 | (2006.01) | |
| C12N 7/00 | (2006.01) | |
| A01K 67/00 | (2006.01) | |
| A61K 38/00 | (2006.01) | |

(52) U.S. Cl.
CPC .......... *A61K 48/0058* (2013.01); *A61K 38/37* (2013.01); *C07K 14/755* (2013.01); *C12N 7/00* (2013.01); *C12N 15/86* (2013.01); *A61K 38/00* (2013.01); *C12N 2710/10041* (2013.01); *C12N 2710/14143* (2013.01); *C12N 2750/14143* (2013.01); *C12N 2800/22* (2013.01); *C12N 2830/008* (2013.01)

(58) Field of Classification Search
CPC .. A61K 48/0058; A61K 38/37; C07K 14/755; C12N 15/86; C12N 2710/14143; C12N 2750/14143; C12N 2830/008
See application file for complete search history.

(56) References Cited

U.S. PATENT DOCUMENTS

| | | |
|---|---|---|
| 6,924,365 B1 | 8/2005 | Miller et al. |
| 7,351,813 B2 | 4/2008 | Miao et al. |
| 8,198,421 B2 | 6/2012 | Samulski |
| 9,393,323 B2 * | 7/2016 | Nathwani ............ C07K 14/755 |
| 2009/0017533 A1 | 1/2009 | Selden et al. |
| 2013/0024960 A1 | 1/2013 | Nathwani et al. |

FOREIGN PATENT DOCUMENTS

| | | |
|---|---|---|
| WO | WO-01/98482 A2 | 12/2001 |
| WO | WO-2005/052171 A2 | 6/2005 |
| WO | WO-2009/017533 A1 | 2/2009 |

OTHER PUBLICATIONS

McIntosh J et al. Therapeutic levels of FVIII following a single peripheral vein administration of rAAV vector encoding a novel human factor VIII variant. Blood 121:3335-3344, 2013.*
Alam et al., Lung surfactant protein B promoter function is dependent on the helical phasing, orientation and combinatorial actions of cis-DNA elements, Gene, 282(1-2):103-11 (2002).
Factor VIII [*Homo sapiens*], GenBank: AAA52484.1 (Nov. 8, 1994).
Grote et al., JCat: a novel tool to adapt codon usage of a target gene to its potential expression host, Nucleic Acids Res., 33:W526-31 (2005).
Lam et al., An efficient and safe herpes simplex virus type 1 amplicon vector for transcriptionally targeted therapy of human hepatocellular carcinomas, Mol. Ther., 15(6):1129-36 (2007).
Lee et al., A new potent hFIX plasmid for hemophilia B gene therapy, Pharm. Res., 21(7):1229-32 (2004).
Miao et al., Bioengineering of coagulation factor VIII for improved secretion, Blood, 103(9):3412-9 (2004).
Müller et al., Repression of lac promoter as a function of distance, phase and quality of an auxiliary lac operator, J. Mol. Biol., 257(1):21-9 (1996).
Okuyama et al., Liver-directed gene therapy: a retroviral vector with a complete LTR and the ApoE enhancer-alpha 1-antitrypsin promoter dramatically increases expression of human alpha 1-antitrypsin in vivo, Hum. Gene Ther., 7(5):637-45 (1996).
Pipe et al., The secretion efficiency of factor VIII can be regulated by the size and oligosaccharide content of the B domain, Blood, 106(11):203A (Nov. 2005).

(Continued)

*Primary Examiner* — Quang Nguyen
(74) *Attorney, Agent, or Firm* — Marshall, Gerstein & Borun LLP

(57) ABSTRACT

An optimized coding sequence of human blood clotting factor eight (VIII) and a promoter may be used in vectors, such as rAAV, for introduction of factor VIII, and/or other blood clotting factors and transgenes. Exemplary of these factors and transgenes are alpha-1-antitrypsin, as well as those involved in the coagulation cascade, hepatocye biology, lysosomal storage, urea cycle disorders, and lipid storage diseases. Cells, vectors, proteins, and glycoproteins produced by cells transformed by the vectors and sequence, may be used in treatment.

3 Claims, 14 Drawing Sheets

(56) References Cited

OTHER PUBLICATIONS

Figure 1:
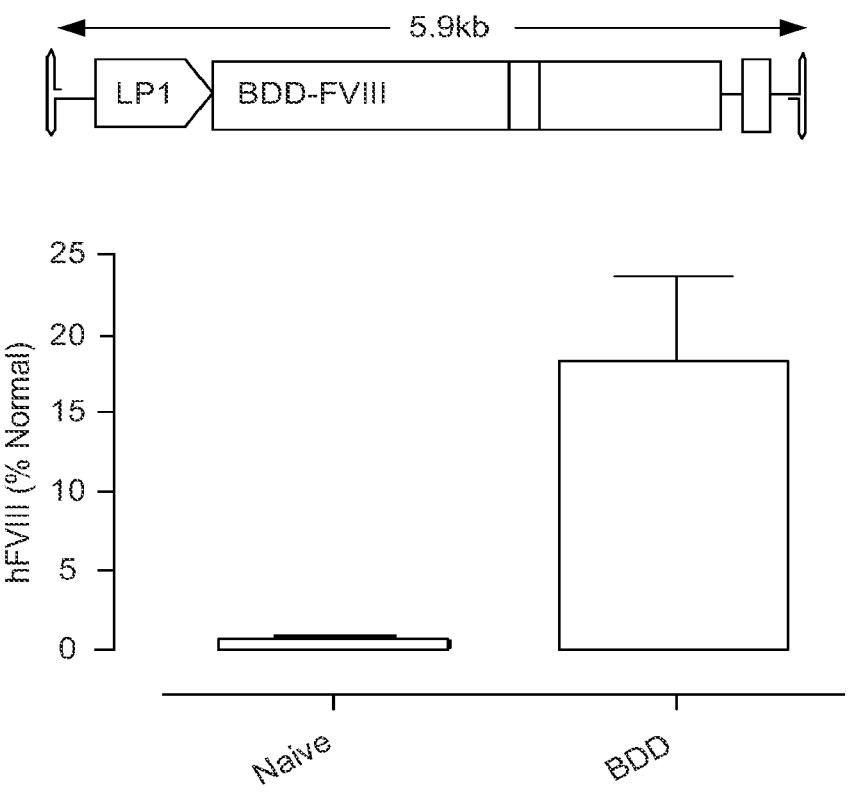

Pittman et al., A2 domain of human recombinant-derived factor VIII is required for procoagulant activity but not for thrombin cleavage, Blood, 79(2):389-97 (1992).
Pittman et al., Role of the B domain for factor VIII and factor V expression and function, Blood, 84(12):4214-25 (1994).
Radcliffe et al., Analysis of factor VIII mediated suppression of lentiviral vector titres, Gene Ther., 15(4):289-97 (2008).
Sandberg et al., Structural and functional characteristics of the B-domain-deleted recombinant factor VIII protein, r-VIII SQ, Thromb. Haemost., 85(1):93-100 (2001).
Shachter et al., Localization of a liver-specific enhanced in the apolipoprotein E/C-I/C-II gene locus, J. Lipid Res., 34(10):1699-707 (1993).
Toole et al., Molecular cloning of a cDNA encoding human antihaemophilic factor, 312(5992):342-7 (1984).
Ward et al., Codon optimization of human factor VIII cDNAS leads to high-level expression, Blood, 117(3):798-807 (2011).
Xie et al., Domains of the rat rDNA promoter must be aligned stereospecifically, Mol. Cell Biol., 12(3):1266-75 (1992).

* cited by examiner

SEQUENCE LISTING

<160> NUMBER OF SEQ ID NOS: 23

<210> SEQ ID NO 1
<211> LENGTH: 4890
<212> TYPE: DNA
<213> ORGANISM: Artificial sequence
<220> FEATURE:
<223> OTHER INFORMATION: Codon optimised modified factor VIII nucleotide
      sequence
<220> FEATURE:
<221> NAME/KEY: CDS
<222> LOCATION: (1)..(4890)

<400> SEQUENCE: 1

```
atg cag att gag ctg agc acc tgc ttc ttc ctg tgc ctg ctg agg ttc      48
Met Gln Ile Glu Leu Ser Thr Cys Phe Phe Leu Cys Leu Leu Arg Phe
1               5                   10                  15 tgc ttc tct gcc acc agg aga tac tac ctg ggg gct gtg gag ctg agc      96
Cys Phe Ser Ala Thr Arg Arg Tyr Tyr Leu Gly Ala Val Glu Leu Ser
            20                  25                  30 tgg gac tac atg cag tct gac ctg ggg gag ctg cct gtg gat gcc agg     144
Trp Asp Tyr Met Gln Ser Asp Leu Gly Glu Leu Pro Val Asp Ala Arg
        35                  40                  45 ttc ccc ccc aga gtg ccc aag agc ttc ccc ttc aac acc tct gtg gtg     192
Phe Pro Pro Arg Val Pro Lys Ser Phe Pro Phe Asn Thr Ser Val Val
    50                  55                  60 tac aag aag acc ctg ttt gtg gag ttc act gac cac ctg ttc aac att     240
Tyr Lys Lys Thr Leu Phe Val Glu Phe Thr Asp His Leu Phe Asn Ile
65                  70                  75                  80 gcc aag ccc agg ccc ccc tgg atg ggc ctg ctg ggc ccc acc atc cag     288
Ala Lys Pro Arg Pro Pro Trp Met Gly Leu Leu Gly Pro Thr Ile Gln
                85                  90                  95 gct gag gtg tat gac act gtg gtg atc acc ctg aag aac atg gcc agc     336
Ala Glu Val Tyr Asp Thr Val Val Ile Thr Leu Lys Asn Met Ala Ser
            100                 105                 110 cac cct gtg agc ctg cat gct gtg ggg gtg agc tac tgg aag gcc tct     384
His Pro Val Ser Leu His Ala Val Gly Val Ser Tyr Trp Lys Ala Ser
        115                 120                 125 gag ggg gct gag tat gat gac cag acc agc cag agg gag aag gag gat     432
Glu Gly Ala Glu Tyr Asp Asp Gln Thr Ser Gln Arg Glu Lys Glu Asp
    130                 135                 140 gac aag gtg ttc cct ggg ggc agc cac acc tat gtg tgg cag gtg ctg     480
Asp Lys Val Phe Pro Gly Gly Ser His Thr Tyr Val Trp Gln Val Leu
145                 150                 155                 160 aag gag aat ggc ccc atg gcc tct gac ccc ctg tgc ctg acc tac agc     528
Lys Glu Asn Gly Pro Met Ala Ser Asp Pro Leu Cys Leu Thr Tyr Ser
                165                 170                 175 tac ctg agc cat gtg gac ctg gtg aag gac ctg aac tct ggc ctg att     576
Tyr Leu Ser His Val Asp Leu Val Lys Asp Leu Asn Ser Gly Leu Ile
            180                 185                 190 ggg gcc ctg ctg gtg tgc agg gag ggc agc ctg gcc aag gag aag acc     624
Gly Ala Leu Leu Val Cys Arg Glu Gly Ser Leu Ala Lys Glu Lys Thr
        195                 200                 205 cag acc ctg cac aag ttc atc ctg ctg ttt gct gtg ttt gat gag ggc     672
Gln Thr Leu His Lys Phe Ile Leu Leu Phe Ala Val Phe Asp Glu Gly
    210                 215                 220 aag agc tgg cac tct gaa acc aag aac agc ctg atg cag gac agg gat     720
Lys Ser Trp His Ser Glu Thr Lys Asn Ser Leu Met Gln Asp Arg Asp
225                 230                 235                 240 gct gcc tct gcc agg gcc tgg ccc aag atg cac act gtg aat ggc tat     768
Ala Ala Ser Ala Arg Ala Trp Pro Lys Met His Thr Val Asn Gly Tyr
                245                 250                 255
```

| | | | | | | | | | | | | | | | | |
|---|---|---|---|---|---|---|---|---|---|---|---|---|---|---|---|---|
| gtg | aac | agg | agc | ctg | cct | ggc | ctg | att | ggc | tgc | cac | agg | aag | tct | gtg | 816 |
| Val | Asn | Arg | Ser | Leu | Pro | Gly | Leu | Ile | Gly | Cys | His | Arg | Lys | Ser | Val | |
| | | | 260 | | | | | 265 | | | | | 270 | | | |
| tac | tgg | cat | gtg | att | ggc | atg | ggc | acc | acc | cct | gag | gtg | cac | agc | atc | 864 |
| Tyr | Trp | His | Val | Ile | Gly | Met | Gly | Thr | Thr | Pro | Glu | Val | His | Ser | Ile | |
| | | 275 | | | | | 280 | | | | | 285 | | | | |
| ttc | ctg | gag | ggc | cac | acc | ttc | ctg | gtc | agg | aac | cac | agg | cag | gcc | agc | 912 |
| Phe | Leu | Glu | Gly | His | Thr | Phe | Leu | Val | Arg | Asn | His | Arg | Gln | Ala | Ser | |
| | 290 | | | | | 295 | | | | | 300 | | | | | |
| ctg | gag | atc | agc | ccc | atc | acc | ttc | ctg | act | gcc | cag | acc | ctg | ctg | atg | 960 |
| Leu | Glu | Ile | Ser | Pro | Ile | Thr | Phe | Leu | Thr | Ala | Gln | Thr | Leu | Leu | Met | |
| 305 | | | | | 310 | | | | | 315 | | | | | 320 | |
| gac | ctg | ggc | cag | ttc | ctg | ctg | ttc | tgc | cac | atc | agc | agc | cac | cag | cat | 1008 |
| Asp | Leu | Gly | Gln | Phe | Leu | Leu | Phe | Cys | His | Ile | Ser | Ser | His | Gln | His | |
| | | | | 325 | | | | | 330 | | | | | 335 | | |
| gat | ggc | atg | gag | gcc | tat | gtg | aag | gtg | gac | agc | tgc | cct | gag | gag | ccc | 1056 |
| Asp | Gly | Met | Glu | Ala | Tyr | Val | Lys | Val | Asp | Ser | Cys | Pro | Glu | Glu | Pro | |
| | | | 340 | | | | | 345 | | | | | 350 | | | |
| cag | ctg | agg | atg | aag | aac | aat | gag | gag | gct | gag | gac | tat | gat | gat | gac | 1104 |
| Gln | Leu | Arg | Met | Lys | Asn | Asn | Glu | Glu | Ala | Glu | Asp | Tyr | Asp | Asp | Asp | |
| | | 355 | | | | | 360 | | | | | 365 | | | | |
| ctg | act | gac | tct | gag | atg | gat | gtg | gtg | agg | ttt | gat | gat | gac | aac | agc | 1152 |
| Leu | Thr | Asp | Ser | Glu | Met | Asp | Val | Val | Arg | Phe | Asp | Asp | Asp | Asn | Ser | |
| | 370 | | | | | 375 | | | | | 380 | | | | | |
| ccc | agc | ttc | atc | cag | atc | agg | tct | gtg | gcc | aag | aag | cac | ccc | aag | acc | 1200 |
| Pro | Ser | Phe | Ile | Gln | Ile | Arg | Ser | Val | Ala | Lys | Lys | His | Pro | Lys | Thr | |
| 385 | | | | | 390 | | | | | 395 | | | | | 400 | |
| tgg | gtg | cac | tac | att | gct | gct | gag | gag | gag | gac | tgg | gac | tat | gcc | ccc | 1248 |
| Trp | Val | His | Tyr | Ile | Ala | Ala | Glu | Glu | Glu | Asp | Trp | Asp | Tyr | Ala | Pro | |
| | | | | 405 | | | | | 410 | | | | | 415 | | |
| ctg | gtg | ctg | gcc | cct | gat | gac | agg | agc | tac | aag | agc | cag | tac | ctg | aac | 1296 |
| Leu | Val | Leu | Ala | Pro | Asp | Asp | Arg | Ser | Tyr | Lys | Ser | Gln | Tyr | Leu | Asn | |
| | | | 420 | | | | | 425 | | | | | 430 | | | |
| aat | ggc | ccc | cag | agg | att | ggc | agg | aag | tac | aag | aag | gtc | agg | ttc | atg | 1344 |
| Asn | Gly | Pro | Gln | Arg | Ile | Gly | Arg | Lys | Tyr | Lys | Lys | Val | Arg | Phe | Met | |
| | | | 435 | | | | | 440 | | | | | 445 | | | |
| gcc | tac | act | gat | gaa | acc | ttc | aag | acc | agg | gag | gcc | atc | cag | cat | gag | 1392 |
| Ala | Tyr | Thr | Asp | Glu | Thr | Phe | Lys | Thr | Arg | Glu | Ala | Ile | Gln | His | Glu | |
| | 450 | | | | | 455 | | | | | 460 | | | | | |
| tct | ggc | atc | ctg | ggc | ccc | ctg | ctg | tat | ggg | gag | gtg | ggg | gac | acc | ctg | 1440 |
| Ser | Gly | Ile | Leu | Gly | Pro | Leu | Leu | Tyr | Gly | Glu | Val | Gly | Asp | Thr | Leu | |
| 465 | | | | | 470 | | | | | 475 | | | | | 480 | |
| ctg | atc | atc | ttc | aag | aac | cag | gcc | agc | agg | ccc | tac | aac | atc | tac | ccc | 1488 |
| Leu | Ile | Ile | Phe | Lys | Asn | Gln | Ala | Ser | Arg | Pro | Tyr | Asn | Ile | Tyr | Pro | |
| | | | | 485 | | | | | 490 | | | | | 495 | | |
| cat | ggc | atc | act | gat | gtg | agg | ccc | ctg | tac | agc | agg | agg | ctg | ccc | aag | 1536 |
| His | Gly | Ile | Thr | Asp | Val | Arg | Pro | Leu | Tyr | Ser | Arg | Arg | Leu | Pro | Lys | |
| | | | 500 | | | | | 505 | | | | | 510 | | | |
| ggg | gtg | aag | cac | ctg | aag | gac | ttc | ccc | atc | ctg | cct | ggg | gag | atc | ttc | 1584 |
| Gly | Val | Lys | His | Leu | Lys | Asp | Phe | Pro | Ile | Leu | Pro | Gly | Glu | Ile | Phe | |
| | | 515 | | | | | 520 | | | | | 525 | | | | |
| aag | tac | aag | tgg | act | gtg | act | gtg | gag | gat | ggc | ccc | acc | aag | tct | gac | 1632 |
| Lys | Tyr | Lys | Trp | Thr | Val | Thr | Val | Glu | Asp | Gly | Pro | Thr | Lys | Ser | Asp | |
| | 530 | | | | | 535 | | | | | 540 | | | | | |
| ccc | agg | tgc | ctg | acc | aga | tac | tac | agc | agc | ttt | gtg | aac | atg | gag | agg | 1680 |
| Pro | Arg | Cys | Leu | Thr | Arg | Tyr | Tyr | Ser | Ser | Phe | Val | Asn | Met | Glu | Arg | |
| 545 | | | | | 550 | | | | | 555 | | | | | 560 | |
| gac | ctg | gcc | tct | ggc | ctg | att | ggc | ccc | ctg | ctg | atc | tgc | tac | aag | gag | 1728 |
| Asp | Leu | Ala | Ser | Gly | Leu | Ile | Gly | Pro | Leu | Leu | Ile | Cys | Tyr | Lys | Glu | |

-continued

|  |  |  |  |  |  |  |  |  |  |  |  |  |  |  |  |
|---|---|---|---|---|---|---|---|---|---|---|---|---|---|---|---|
|  |  | 565 |  |  |  | 570 |  |  |  |  | 575 |  |  |  |  |
| tct | gtg | gac | cag | agg | ggc | aac | cag | atc | atg | tct | gac | aag | agg | aat | gtg | 1776 |
| Ser | Val | Asp | Gln | Arg | Gly | Asn | Gln | Ile | Met | Ser | Asp | Lys | Arg | Asn | Val |  |
|  |  | 580 |  |  |  |  | 585 |  |  |  | 590 |  |  |  |  |  |
| atc | ctg | ttc | tct | gtg | ttt | gat | gag | aac | agg | agc | tgg | tac | ctg | act | gag | 1824 |
| Ile | Leu | Phe | Ser | Val | Phe | Asp | Glu | Asn | Arg | Ser | Trp | Tyr | Leu | Thr | Glu |  |
|  |  |  | 595 |  |  |  |  | 600 |  |  |  | 605 |  |  |  |  |
| aac | atc | cag | agg | ttc | ctg | ccc | aac | cct | gct | ggg | gtg | cag | ctg | gag | gac | 1872 |
| Asn | Ile | Gln | Arg | Phe | Leu | Pro | Asn | Pro | Ala | Gly | Val | Gln | Leu | Glu | Asp |  |
|  | 610 |  |  |  |  | 615 |  |  |  | 620 |  |  |  |  |  |  |
| cct | gag | ttc | cag | gcc | agc | aac | atc | atg | cac | agc | atc | aat | ggc | tat | gtg | 1920 |
| Pro | Glu | Phe | Gln | Ala | Ser | Asn | Ile | Met | His | Ser | Ile | Asn | Gly | Tyr | Val |  |
| 625 |  |  |  |  | 630 |  |  |  |  | 635 |  |  |  |  | 640 |  |
| ttt | gac | agc | ctg | cag | ctg | tct | gtg | tgc | ctg | cat | gag | gtg | gcc | tac | tgg | 1968 |
| Phe | Asp | Ser | Leu | Gln | Leu | Ser | Val | Cys | Leu | His | Glu | Val | Ala | Tyr | Trp |  |
|  |  |  |  | 645 |  |  |  |  | 650 |  |  |  |  | 655 |  |  |
| tac | atc | ctg | agc | att | ggg | gcc | cag | act | gac | ttc | ctg | tct | gtg | ttc | ttc | 2016 |
| Tyr | Ile | Leu | Ser | Ile | Gly | Ala | Gln | Thr | Asp | Phe | Leu | Ser | Val | Phe | Phe |  |
|  |  |  | 660 |  |  |  |  | 665 |  |  |  | 670 |  |  |  |  |
| tct | ggc | tac | acc | ttc | aag | cac | aag | atg | gtg | tat | gag | gac | acc | ctg | acc | 2064 |
| Ser | Gly | Tyr | Thr | Phe | Lys | His | Lys | Met | Val | Tyr | Glu | Asp | Thr | Leu | Thr |  |
|  |  | 675 |  |  |  |  | 680 |  |  |  | 685 |  |  |  |  |  |
| ctg | ttc | ccc | ttc | tct | ggg | gag | act | gtg | ttc | atg | agc | atg | gag | aac | cct | 2112 |
| Leu | Phe | Pro | Phe | Ser | Gly | Glu | Thr | Val | Phe | Met | Ser | Met | Glu | Asn | Pro |  |
|  | 690 |  |  |  |  | 695 |  |  |  | 700 |  |  |  |  |  |  |
| ggc | ctg | tgg | att | ctg | ggc | tgc | cac | aac | tct | gac | ttc | agg | aac | agg | ggc | 2160 |
| Gly | Leu | Trp | Ile | Leu | Gly | Cys | His | Asn | Ser | Asp | Phe | Arg | Asn | Arg | Gly |  |
| 705 |  |  |  |  | 710 |  |  |  |  | 715 |  |  |  |  | 720 |  |
| atg | act | gcc | ctg | ctg | aaa | gtc | tcc | agc | tgt | gac | aag | aac | act | ggg | gac | 2208 |
| Met | Thr | Ala | Leu | Leu | Lys | Val | Ser | Ser | Cys | Asp | Lys | Asn | Thr | Gly | Asp |  |
|  |  |  |  | 725 |  |  |  |  | 730 |  |  |  |  | 735 |  |  |
| tac | tat | gag | gac | agc | tat | gag | gac | atc | tct | gcc | tac | ctg | ctg | agc | aag | 2256 |
| Tyr | Tyr | Glu | Asp | Ser | Tyr | Glu | Asp | Ile | Ser | Ala | Tyr | Leu | Leu | Ser | Lys |  |
|  |  |  | 740 |  |  |  |  | 745 |  |  |  | 750 |  |  |  |  |
| aac | aat | gcc | att | gag | ccc | agg | agc | ttc | agc | cag | aac | agc | agg | cac | ccc | 2304 |
| Asn | Asn | Ala | Ile | Glu | Pro | Arg | Ser | Phe | Ser | Gln | Asn | Ser | Arg | His | Pro |  |
|  |  | 755 |  |  |  |  | 760 |  |  |  | 765 |  |  |  |  |  |
| agc | acc | agg | cag | aag | cag | ttc | aat | gcc | acc | acc | atc | cct | gag | aat | gac | 2352 |
| Ser | Thr | Arg | Gln | Lys | Gln | Phe | Asn | Ala | Thr | Thr | Ile | Pro | Glu | Asn | Asp |  |
|  | 770 |  |  |  |  | 775 |  |  |  | 780 |  |  |  |  |  |  |
| ata | gag | aag | aca | gac | cca | tgg | ttt | gcc | cac | cgg | acc | ccc | atg | ccc | aag | 2400 |
| Ile | Glu | Lys | Thr | Asp | Pro | Trp | Phe | Ala | His | Arg | Thr | Pro | Met | Pro | Lys |  |
| 785 |  |  |  |  | 790 |  |  |  |  | 795 |  |  |  |  | 800 |  |
| atc | cag | aat | gtg | agc | agc | tct | gac | ctg | ctg | atg | ctg | ctg | agg | cag | agc | 2448 |
| Ile | Gln | Asn | Val | Ser | Ser | Ser | Asp | Leu | Leu | Met | Leu | Leu | Arg | Gln | Ser |  |
|  |  |  |  | 805 |  |  |  |  | 810 |  |  |  |  | 815 |  |  |
| ccc | acc | ccc | cat | ggc | ctg | agc | ctg | tct | gac | ctg | cag | gag | gcc | aag | tat | 2496 |
| Pro | Thr | Pro | His | Gly | Leu | Ser | Leu | Ser | Asp | Leu | Gln | Glu | Ala | Lys | Tyr |  |
|  |  |  | 820 |  |  |  |  | 825 |  |  |  | 830 |  |  |  |  |
| gaa | acc | ttc | tct | gat | gac | ccc | agc | cct | ggg | gcc | att | gac | agc | aac | aac | 2544 |
| Glu | Thr | Phe | Ser | Asp | Asp | Pro | Ser | Pro | Gly | Ala | Ile | Asp | Ser | Asn | Asn |  |
|  |  | 835 |  |  |  |  | 840 |  |  |  | 845 |  |  |  |  |  |
| agc | ctg | tct | gag | atg | acc | cac | ttc | agg | ccc | cag | ctg | cac | cac | tct | ggg | 2592 |
| Ser | Leu | Ser | Glu | Met | Thr | His | Phe | Arg | Pro | Gln | Leu | His | His | Ser | Gly |  |
|  | 850 |  |  |  |  | 855 |  |  |  | 860 |  |  |  |  |  |  |
| gac | atg | gtg | ttc | acc | cct | gag | tct | ggc | ctg | cag | ctg | agg | ctg | aat | gag | 2640 |
| Asp | Met | Val | Phe | Thr | Pro | Glu | Ser | Gly | Leu | Gln | Leu | Arg | Leu | Asn | Glu |  |
| 865 |  |  |  |  | 870 |  |  |  |  | 875 |  |  |  |  | 880 |  |
| aag | ctg | ggc | acc | act | gct | gcc | act | gag | ctg | aag | aag | ctg | gac | ttc | aaa | 2688 |

```
                                       -continued

Lys Leu Gly Thr Thr Ala Ala Thr Glu Leu Lys Lys Leu Asp Phe Lys
                    885                 890                 895 gtc tcc agc acc agc aac aac ctg atc agc acc atc ccc tct gac aac    2736
Val Ser Ser Thr Ser Asn Asn Leu Ile Ser Thr Ile Pro Ser Asp Asn
                900                 905                 910 ctg gct gct ggc act gac aac acc agc agc ctg ggc ccc ccc agc atg    2784
Leu Ala Ala Gly Thr Asp Asn Thr Ser Ser Leu Gly Pro Pro Ser Met
                915                 920                 925 cct gtg cac tat gac agc cag ctg gac acc acc ctg ttt ggc aag aag    2832
Pro Val His Tyr Asp Ser Gln Leu Asp Thr Thr Leu Phe Gly Lys Lys
            930                 935                 940 agc agc ccc ctg act gag tct ggg ggc ccc ctg agc ctg tct gag gag    2880
Ser Ser Pro Leu Thr Glu Ser Gly Gly Pro Leu Ser Leu Ser Glu Glu
945                 950                 955                 960 aac aat gac agc aag ctg ctg gag tct ggc ctg atg aac agc cag gag    2928
Asn Asn Asp Ser Lys Leu Leu Glu Ser Gly Leu Met Asn Ser Gln Glu
                965                 970                 975 agc agc tgg ggc aag aat gtg agc acc agg agc ttc cag aag aag acc    2976
Ser Ser Trp Gly Lys Asn Val Ser Thr Arg Ser Phe Gln Lys Lys Thr
                980                 985                 990 agg cac tac ttc att gct gct gtg  gag agg ctg tgg gac  tat ggc atg   3024
Arg His Tyr Phe Ile Ala Ala Val  Glu Arg Leu Trp Asp  Tyr Gly Met
            995                 1000                1005 agc agc  agc ccc cat gtg ctg  agg aac agg gcc cag  tct ggc tct      3069
Ser Ser  Ser Pro His Val Leu  Arg Asn Arg Ala Gln  Ser Gly Ser
1010                1015                1020 gtg ccc  cag ttc aag aag gtg  gtg ttc cag gag ttc  act gat ggc      3114
Val Pro  Gln Phe Lys Lys Val  Val Phe Gln Glu Phe  Thr Asp Gly
1025                1030                1035 agc ttc  acc cag ccc ctg tac  aga ggg gag ctg aat  gag cac ctg      3159
Ser Phe  Thr Gln Pro Leu Tyr  Arg Gly Glu Leu Asn  Glu His Leu
1040                1045                1050 ggc ctg  ctg ggc ccc tac atc  agg gct gag gtg gag  gac aac atc      3204
Gly Leu  Leu Gly Pro Tyr Ile  Arg Ala Glu Val Glu  Asp Asn Ile
1055                1060                1065 atg gtg  acc ttc agg aac cag  gcc agc agg ccc tac  agc ttc tac      3249
Met Val  Thr Phe Arg Asn Gln  Ala Ser Arg Pro Tyr  Ser Phe Tyr
1070                1075                1080 agc agc  ctg atc agc tat gag  gag gac cag agg cag  ggg gct gag      3294
Ser Ser  Leu Ile Ser Tyr Glu  Glu Asp Gln Arg Gln  Gly Ala Glu
1085                1090                1095 ccc agg  aag aac ttt gtg aag  ccc aat gaa acc aag  acc tac ttc      3339
Pro Arg  Lys Asn Phe Val Lys  Pro Asn Glu Thr Lys  Thr Tyr Phe
1100                1105                1110 tgg aag  gtg cag cac cac atg  gcc ccc acc aag gat  gag ttt gac      3384
Trp Lys  Val Gln His His Met  Ala Pro Thr Lys Asp  Glu Phe Asp
1115                1120                1125 tgc aag  gcc tgg gcc tac ttc  tct gat gtg gac ctg  gag aag gat      3429
Cys Lys  Ala Trp Ala Tyr Phe  Ser Asp Val Asp Leu  Glu Lys Asp
1130                1135                1140 gtg cac  tct ggc ctg att ggc  ccc ctg ctg gtg tgc  cac acc aac      3474
Val His  Ser Gly Leu Ile Gly  Pro Leu Leu Val Cys  His Thr Asn
1145                1150                1155 acc ctg  aac cct gcc cat ggc  agg cag gtg act gtg  cag gag ttt      3519
Thr Leu  Asn Pro Ala His Gly  Arg Gln Val Thr Val  Gln Glu Phe
1160                1165                1170 gcc ctg  ttc ttc acc atc ttt  gat gaa acc aag agc  tgg tac ttc      3564
Ala Leu  Phe Phe Thr Ile Phe  Asp Glu Thr Lys Ser  Trp Tyr Phe
1175                1180                1185
```

-continued

| | | | | | | | | | | | | |
|---|---|---|---|---|---|---|---|---|---|---|---|---|
| act | gag | aac | atg | gag | agg | aac | tgc | agg | gcc | ccc | tgc | aac atc cag | 3609 |
| Thr | Glu | Asn | Met | Glu | Arg | Asn | Cys | Arg | Ala | Pro | Cys | Asn Ile Gln |
| 1190 | | | | 1195 | | | | | 1200 | | | |
| atg | gag | gac | ccc | acc | ttc | aag | gag | aac | tac | agg | ttc | cat gcc atc | 3654 |
| Met | Glu | Asp | Pro | Thr | Phe | Lys | Glu | Asn | Tyr | Arg | Phe | His Ala Ile |
| 1205 | | | | 1210 | | | | | 1215 | | | |
| aat | ggc | tac | atc | atg | gac | acc | ctg | cct | ggc | ctg | gtg | atg gcc cag | 3699 |
| Asn | Gly | Tyr | Ile | Met | Asp | Thr | Leu | Pro | Gly | Leu | Val | Met Ala Gln |
| 1220 | | | | 1225 | | | | | 1230 | | | |
| gac | cag | agg | atc | agg | tgg | tac | ctg | ctg | agc | atg | ggc | agc aat gag | 3744 |
| Asp | Gln | Arg | Ile | Arg | Trp | Tyr | Leu | Leu | Ser | Met | Gly | Ser Asn Glu |
| 1235 | | | | 1240 | | | | | 1245 | | | |
| aac | atc | cac | agc | atc | cac | ttc | tct | ggc | cat | gtg | ttc | act gtg agg | 3789 |
| Asn | Ile | His | Ser | Ile | His | Phe | Ser | Gly | His | Val | Phe | Thr Val Arg |
| 1250 | | | | 1255 | | | | | 1260 | | | |
| aag | aag | gag | gag | tac | aag | atg | gcc | ctg | tac | aac | ctg | tac cct ggg | 3834 |
| Lys | Lys | Glu | Glu | Tyr | Lys | Met | Ala | Leu | Tyr | Asn | Leu | Tyr Pro Gly |
| 1265 | | | | 1270 | | | | | 1275 | | | |
| gtg | ttt | gag | act | gtg | gag | atg | ctg | ccc | agc | aag | gct | ggc atc tgg | 3879 |
| Val | Phe | Glu | Thr | Val | Glu | Met | Leu | Pro | Ser | Lys | Ala | Gly Ile Trp |
| 1280 | | | | 1285 | | | | | 1290 | | | |
| agg | gtg | gag | tgc | ctg | att | ggg | gag | cac | ctg | cat | gct | ggc atg agc | 3924 |
| Arg | Val | Glu | Cys | Leu | Ile | Gly | Glu | His | Leu | His | Ala | Gly Met Ser |
| 1295 | | | | 1300 | | | | | 1305 | | | |
| acc | ctg | ttc | ctg | gtg | tac | agc | aac | aag | tgc | cag | acc | ccc ctg ggc | 3969 |
| Thr | Leu | Phe | Leu | Val | Tyr | Ser | Asn | Lys | Cys | Gln | Thr | Pro Leu Gly |
| 1310 | | | | 1315 | | | | | 1320 | | | |
| atg | gcc | tct | ggc | cac | atc | agg | gac | ttc | cag | atc | act | gcc tct ggc | 4014 |
| Met | Ala | Ser | Gly | His | Ile | Arg | Asp | Phe | Gln | Ile | Thr | Ala Ser Gly |
| 1325 | | | | 1330 | | | | | 1335 | | | |
| cag | tat | ggc | cag | tgg | gcc | ccc | aag | ctg | gcc | agg | ctg | cac tac tct | 4059 |
| Gln | Tyr | Gly | Gln | Trp | Ala | Pro | Lys | Leu | Ala | Arg | Leu | His Tyr Ser |
| 1340 | | | | 1345 | | | | | 1350 | | | |
| ggc | agc | atc | aat | gcc | tgg | agc | acc | aag | gag | ccc | ttc | agc tgg atc | 4104 |
| Gly | Ser | Ile | Asn | Ala | Trp | Ser | Thr | Lys | Glu | Pro | Phe | Ser Trp Ile |
| 1355 | | | | 1360 | | | | | 1365 | | | |
| aag | gtg | gac | ctg | ctg | gcc | ccc | atg | atc | atc | cat | ggc | atc aag acc | 4149 |
| Lys | Val | Asp | Leu | Leu | Ala | Pro | Met | Ile | Ile | His | Gly | Ile Lys Thr |
| 1370 | | | | 1375 | | | | | 1380 | | | |
| cag | ggg | gcc | agg | cag | aag | ttc | agc | agc | ctg | tac | atc | agc cag ttc | 4194 |
| Gln | Gly | Ala | Arg | Gln | Lys | Phe | Ser | Ser | Leu | Tyr | Ile | Ser Gln Phe |
| 1385 | | | | 1390 | | | | | 1395 | | | |
| atc | atc | atg | tac | agc | ctg | gat | ggc | aag | aag | tgg | cag | acc tac agg | 4239 |
| Ile | Ile | Met | Tyr | Ser | Leu | Asp | Gly | Lys | Lys | Trp | Gln | Thr Tyr Arg |
| 1400 | | | | 1405 | | | | | 1410 | | | |
| ggc | aac | agc | act | ggc | acc | ctg | atg | gtg | ttc | ttt | ggc | aat gtg gac | 4284 |
| Gly | Asn | Ser | Thr | Gly | Thr | Leu | Met | Val | Phe | Phe | Gly | Asn Val Asp |
| 1415 | | | | 1420 | | | | | 1425 | | | |
| agc | tct | ggc | atc | aag | cac | aac | atc | ttc | aac | ccc | ccc | atc att gcc | 4329 |
| Ser | Ser | Gly | Ile | Lys | His | Asn | Ile | Phe | Asn | Pro | Pro | Ile Ile Ala |
| 1430 | | | | 1435 | | | | | 1440 | | | |
| aga | tac | atc | agg | ctg | cac | ccc | acc | cac | tac | agc | atc | agg agc acc | 4374 |
| Arg | Tyr | Ile | Arg | Leu | His | Pro | Thr | His | Tyr | Ser | Ile | Arg Ser Thr |
| 1445 | | | | 1450 | | | | | 1455 | | | |
| ctg | agg | atg | gag | ctg | atg | ggc | tgt | gac | ctg | aac | agc | tgc agc atg | 4419 |
| Leu | Arg | Met | Glu | Leu | Met | Gly | Cys | Asp | Leu | Asn | Ser | Cys Ser Met |
| 1460 | | | | 1465 | | | | | 1470 | | | |
| ccc | ctg | ggc | atg | gag | agc | aag | gcc | atc | tct | gat | gcc | cag atc act | 4464 |
| Pro | Leu | Gly | Met | Glu | Ser | Lys | Ala | Ile | Ser | Asp | Ala | Gln Ile Thr |
| 1475 | | | | 1480 | | | | | 1485 | | | |

-continued

```
gcc agc agc tac ttc acc aac atg ttt gcc acc tgg agc ccc agc    4509
Ala Ser Ser Tyr Phe Thr Asn Met Phe Ala Thr Trp Ser Pro Ser
    1490            1495                1500 aag gcc agg ctg cac ctg cag ggc agg agc aat gcc tgg agg ccc    4554
Lys Ala Arg Leu His Leu Gln Gly Arg Ser Asn Ala Trp Arg Pro
1505                1510                1515 cag gtc aac aac ccc aag gag tgg ctg cag gtg gac ttc cag aag    4599
Gln Val Asn Asn Pro Lys Glu Trp Leu Gln Val Asp Phe Gln Lys
    1520            1525                1530 acc atg aag gtg act ggg gtg acc acc cag ggg gtg aag agc ctg    4644
Thr Met Lys Val Thr Gly Val Thr Thr Gln Gly Val Lys Ser Leu
        1535            1540                1545 ctg acc agc atg tat gtg aag gag ttc ctg atc agc agc agc cag    4689
Leu Thr Ser Met Tyr Val Lys Glu Phe Leu Ile Ser Ser Ser Gln
    1550            1555                1560 gat ggc cac cag tgg acc ctg ttc ttc cag aat ggc aag gtg aag    4734
Asp Gly His Gln Trp Thr Leu Phe Phe Gln Asn Gly Lys Val Lys
    1565            1570                1575 gtg ttc cag ggc aac cag gac agc ttc acc cct gtg gtg aac agc    4779
Val Phe Gln Gly Asn Gln Asp Ser Phe Thr Pro Val Val Asn Ser
    1580            1585                1590 ctg gac ccc ccc ctg ctg acc aga tac ctg agg att cac ccc cag    4824
Leu Asp Pro Pro Leu Leu Thr Arg Tyr Leu Arg Ile His Pro Gln
    1595            1600                1605 agc tgg gtg cac cag att gcc ctg agg atg gag gtg ctg ggc tgt    4869
Ser Trp Val His Gln Ile Ala Leu Arg Met Glu Val Leu Gly Cys
    1610            1615                1620 gag gcc cag gac ctg tac tga                                    4890
Glu Ala Gln Asp Leu Tyr
    1625

<210> SEQ ID NO 2
<211> LENGTH: 1629
<212> TYPE: PRT
<213> ORGANISM: Artificial sequence
<220> FEATURE:
<223> OTHER INFORMATION: Synthetic Construct

<400> SEQUENCE: 2

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
```

```
            145                 150                 155                 160
        Lys Glu Asn Gly Pro Met Ala Ser Asp Pro Leu Cys Leu Thr Tyr Ser
                        165                 170                 175
        Tyr Leu Ser His Val Asp Leu Val Lys Asp Leu Asn Ser Gly Leu Ile
                        180                 185                 190
        Gly Ala Leu Leu Val Cys Arg Glu Gly Ser Leu Ala Lys Glu Lys Thr
                        195                 200                 205
        Gln Thr Leu His Lys Phe Ile Leu Leu Phe Ala Val Phe Asp Glu Gly
                210                 215                 220
        Lys Ser Trp His Ser Glu Thr Lys Asn Ser Leu Met Gln Asp Arg Asp
        225                 230                 235                 240
        Ala Ala Ser Ala Arg Ala Trp Pro Lys Met His Thr Val Asn Gly Tyr
                        245                 250                 255
        Val Asn Arg Ser Leu Pro Gly Leu Ile Gly Cys His Arg Lys Ser Val
                        260                 265                 270
        Tyr Trp His Val Ile Gly Met Gly Thr Thr Pro Glu Val His Ser Ile
                        275                 280                 285
        Phe Leu Glu Gly His Thr Phe Leu Val Arg Asn His Arg Gln Ala Ser
                290                 295                 300
        Leu Glu Ile Ser Pro Ile Thr Phe Leu Thr Ala Gln Thr Leu Leu Met
        305                 310                 315                 320
        Asp Leu Gly Gln Phe Leu Leu Phe Cys His Ile Ser Ser His Gln His
                        325                 330                 335
        Asp Gly Met Glu Ala Tyr Val Lys Val Asp Ser Cys Pro Glu Glu Pro
                        340                 345                 350
        Gln Leu Arg Met Lys Asn Asn Glu Glu Ala Glu Asp Tyr Asp Asp Asp
                        355                 360                 365
        Leu Thr Asp Ser Glu Met Asp Val Val Arg Phe Asp Asp Asp Asn Ser
                370                 375                 380
        Pro Ser Phe Ile Gln Ile Arg Ser Val Ala Lys Lys His Pro Lys Thr
        385                 390                 395                 400
        Trp Val His Tyr Ile Ala Ala Glu Glu Glu Asp Trp Asp Tyr Ala Pro
                        405                 410                 415
        Leu Val Leu Ala Pro Asp Asp Arg Ser Tyr Lys Ser Gln Tyr Leu Asn
                        420                 425                 430
        Asn Gly Pro Gln Arg Ile Gly Arg Lys Tyr Lys Lys Val Arg Phe Met
                        435                 440                 445
        Ala Tyr Thr Asp Glu Thr Phe Lys Thr Arg Glu Ala Ile Gln His Glu
                450                 455                 460
        Ser Gly Ile Leu Gly Pro Leu Leu Tyr Gly Glu Val Gly Asp Thr Leu
        465                 470                 475                 480
        Leu Ile Ile Phe Lys Asn Gln Ala Ser Arg Pro Tyr Asn Ile Tyr Pro
                        485                 490                 495
        His Gly Ile Thr Asp Val Arg Pro Leu Tyr Ser Arg Arg Leu Pro Lys
                        500                 505                 510
        Gly Val Lys His Leu Lys Asp Phe Pro Ile Leu Pro Gly Glu Ile Phe
                        515                 520                 525
        Lys Tyr Lys Trp Thr Val Thr Val Glu Asp Gly Pro Thr Lys Ser Asp
                530                 535                 540
        Pro Arg Cys Leu Thr Arg Tyr Tyr Ser Ser Phe Val Asn Met Glu Arg
        545                 550                 555                 560
        Asp Leu Ala Ser Gly Leu Ile Gly Pro Leu Leu Ile Cys Tyr Lys Glu
                        565                 570                 575
```

```
Ser Val Asp Gln Arg Gly Asn Gln Ile Met Ser Asp Lys Arg Asn Val
        580                 585                 590
Ile Leu Phe Ser Val Phe Asp Glu Asn Arg Ser Trp Tyr Leu Thr Glu
        595                 600                 605
Asn Ile Gln Arg Phe Leu Pro Asn Pro Ala Gly Val Gln Leu Glu Asp
        610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
            675                 680                 685
Leu Phe Pro Phe Ser Gly Glu Thr Val Phe Met Ser Met Glu Asn Pro
        690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gln Asn Ser Arg His Pro
        755                 760                 765
Ser Thr Arg Gln Lys Gln Phe Asn Ala Thr Thr Ile Pro Glu Asn Asp
        770                 775                 780
Ile Glu Lys Thr Asp Pro Trp Phe Ala His Arg Thr Pro Met Pro Lys
785                 790                 795                 800
Ile Gln Asn Val Ser Ser Ser Asp Leu Leu Met Leu Leu Arg Gln Ser
                805                 810                 815
Pro Thr Pro His Gly Leu Ser Leu Ser Asp Leu Gln Glu Ala Lys Tyr
            820                 825                 830
Glu Thr Phe Ser Asp Asp Pro Ser Pro Gly Ala Ile Asp Ser Asn Asn
            835                 840                 845
Ser Leu Ser Glu Met Thr His Phe Arg Pro Gln Leu His His Ser Gly
        850                 855                 860
Asp Met Val Phe Thr Pro Glu Ser Gly Leu Gln Leu Arg Leu Asn Glu
865                 870                 875                 880
Lys Leu Gly Thr Thr Ala Ala Thr Glu Leu Lys Lys Leu Asp Phe Lys
                885                 890                 895
Val Ser Ser Thr Ser Asn Asn Leu Ile Ser Thr Ile Pro Ser Asp Asn
            900                 905                 910
Leu Ala Ala Gly Thr Asp Asn Thr Ser Ser Leu Gly Pro Pro Ser Met
        915                 920                 925
Pro Val His Tyr Asp Ser Gln Leu Asp Thr Thr Leu Phe Gly Lys Lys
        930                 935                 940
Ser Ser Pro Leu Thr Glu Ser Gly Gly Pro Leu Ser Leu Ser Glu Glu
945                 950                 955                 960
Asn Asn Asp Ser Lys Leu Leu Glu Ser Gly Leu Met Asn Ser Gln Glu
                965                 970                 975
Ser Ser Trp Gly Lys Asn Val Ser Thr Arg Ser Phe Gln Lys Lys Thr
            980                 985                 990
```

-continued

Arg His Tyr Phe Ile Ala Ala Val Glu Arg Leu Trp Asp Tyr Gly Met
            995                 1000                1005

Ser Ser Ser Pro His Val Leu Arg Asn Arg Ala Gln Ser Gly Ser
    1010            1015            1020

Val Pro Gln Phe Lys Lys Val Val Phe Gln Glu Phe Thr Asp Gly
    1025            1030            1035

Ser Phe Thr Gln Pro Leu Tyr Arg Gly Glu Leu Asn Glu His Leu
    1040            1045            1050

Gly Leu Leu Gly Pro Tyr Ile Arg Ala Glu Val Glu Asp Asn Ile
    1055            1060            1065

Met Val Thr Phe Arg Asn Gln Ala Ser Arg Pro Tyr Ser Phe Tyr
    1070            1075            1080

Ser Ser Leu Ile Ser Tyr Glu Glu Asp Gln Arg Gln Gly Ala Glu
    1085            1090            1095

Pro Arg Lys Asn Phe Val Lys Pro Asn Glu Thr Lys Thr Tyr Phe
    1100            1105            1110

Trp Lys Val Gln His His Met Ala Pro Thr Lys Asp Glu Phe Asp
    1115            1120            1125

Cys Lys Ala Trp Ala Tyr Phe Ser Asp Val Asp Leu Glu Lys Asp
    1130            1135            1140

Val His Ser Gly Leu Ile Gly Pro Leu Leu Val Cys His Thr Asn
    1145            1150            1155

Thr Leu Asn Pro Ala His Gly Arg Gln Val Thr Val Gln Glu Phe
    1160            1165            1170

Ala Leu Phe Phe Thr Ile Phe Asp Glu Thr Lys Ser Trp Tyr Phe
    1175            1180            1185

Thr Glu Asn Met Glu Arg Asn Cys Arg Ala Pro Cys Asn Ile Gln
    1190            1195            1200

Met Glu Asp Pro Thr Phe Lys Glu Asn Tyr Arg Phe His Ala Ile
    1205            1210            1215

Asn Gly Tyr Ile Met Asp Thr Leu Pro Gly Leu Val Met Ala Gln
    1220            1225            1230

Asp Gln Arg Ile Arg Trp Tyr Leu Leu Ser Met Gly Ser Asn Glu
    1235            1240            1245

Asn Ile His Ser Ile His Phe Ser Gly His Val Phe Thr Val Arg
    1250            1255            1260

Lys Lys Glu Glu Tyr Lys Met Ala Leu Tyr Asn Leu Tyr Pro Gly
    1265            1270            1275

Val Phe Glu Thr Val Glu Met Leu Pro Ser Lys Ala Gly Ile Trp
    1280            1285            1290

Arg Val Glu Cys Leu Ile Gly Glu His Leu His Ala Gly Met Ser
    1295            1300            1305

Thr Leu Phe Leu Val Tyr Ser Asn Lys Cys Gln Thr Pro Leu Gly
    1310            1315            1320

Met Ala Ser Gly His Ile Arg Asp Phe Gln Ile Thr Ala Ser Gly
    1325            1330            1335

Gln Tyr Gly Gln Trp Ala Pro Lys Leu Ala Arg Leu His Tyr Ser
    1340            1345            1350

Gly Ser Ile Asn Ala Trp Ser Thr Lys Glu Pro Phe Ser Trp Ile
    1355            1360            1365

Lys Val Asp Leu Leu Ala Pro Met Ile Ile His Gly Ile Lys Thr
    1370            1375            1380

Gln Gly Ala Arg Gln Lys Phe Ser Ser Leu Tyr Ile Ser Gln Phe

```
     1385                1390                1395
Ile  Ile  Met  Tyr  Ser  Leu  Asp  Gly  Lys  Lys  Trp  Gln  Thr  Tyr  Arg
     1400                1405                1410

Gly  Asn  Ser  Thr  Gly  Thr  Leu  Met  Val  Phe  Phe  Gly  Asn  Val  Asp
     1415                1420                1425

Ser  Ser  Gly  Ile  Lys  His  Asn  Ile  Phe  Asn  Pro  Pro  Ile  Ile  Ala
     1430                1435                1440

Arg  Tyr  Ile  Arg  Leu  His  Pro  Thr  His  Tyr  Ser  Ile  Arg  Ser  Thr
     1445                1450                1455

Leu  Arg  Met  Glu  Leu  Met  Gly  Cys  Asp  Leu  Asn  Ser  Cys  Ser  Met
     1460                1465                1470

Pro  Leu  Gly  Met  Glu  Ser  Lys  Ala  Ile  Ser  Asp  Ala  Gln  Ile  Thr
     1475                1480                1485

Ala  Ser  Ser  Tyr  Phe  Thr  Asn  Met  Phe  Ala  Thr  Trp  Ser  Pro  Ser
     1490                1495                1500

Lys  Ala  Arg  Leu  His  Leu  Gln  Gly  Arg  Ser  Asn  Ala  Trp  Arg  Pro
     1505                1510                1515

Gln  Val  Asn  Asn  Pro  Lys  Glu  Trp  Leu  Gln  Val  Asp  Phe  Gln  Lys
     1520                1525                1530

Thr  Met  Lys  Val  Thr  Gly  Val  Thr  Thr  Gln  Gly  Val  Lys  Ser  Leu
     1535                1540                1545

Leu  Thr  Ser  Met  Tyr  Val  Lys  Glu  Phe  Leu  Ile  Ser  Ser  Ser  Gln
     1550                1555                1560

Asp  Gly  His  Gln  Trp  Thr  Leu  Phe  Phe  Gln  Asn  Gly  Lys  Val  Lys
     1565                1570                1575

Val  Phe  Gln  Gly  Asn  Gln  Asp  Ser  Phe  Thr  Pro  Val  Val  Asn  Ser
     1580                1585                1590

Leu  Asp  Pro  Pro  Leu  Leu  Thr  Arg  Tyr  Leu  Arg  Ile  His  Pro  Gln
     1595                1600                1605

Ser  Trp  Val  His  Gln  Ile  Ala  Leu  Arg  Met  Glu  Val  Leu  Gly  Cys
     1610                1615                1620

Glu  Ala  Gln  Asp  Leu  Tyr
     1625
```

<210> SEQ ID NO 3
<211> LENGTH: 251
<212> TYPE: DNA
<213> ORGANISM: Artificial sequence
<220> FEATURE:
<223> OTHER INFORMATION: modified promoter sequence

<400> SEQUENCE: 3
tgtttgctgc ttgcaatgtt tgcccatttt agggtggaca caggacgctg tggtttctga     60 gccaggggc gactcagatc ccagccagtg gacttagccc ctgtttgctc ctccgataac    120
tggggtgacc ttggttaata ttcaccagca gcctcccccg ttgcccctct ggatccactg    180
cttaaatacg gacgaggaca gggccctgtc tcctcagctt caggcaccac cactgacctg    240
ggacagtgaa t                                                         251

<210> SEQ ID NO 4
<211> LENGTH: 5061
<212> TYPE: DNA
<213> ORGANISM: Artificial sequence
<220> FEATURE:
<223> OTHER INFORMATION: Codon optimised modified factor VIII nucleotide
      sequence

```
<400> SEQUENCE: 4
atgcagatcg agctgtccac ctgcttttt ctgtgcctgc tgcggttctg cttcagcgcc      60
acccggcggt actacctggg cgccgtggag ctgtcctggg actacatgca gagcgacctg     120
ggcgagctgc ccgtggacgc ccggttcccc cccagagtgc ccaagagctt ccccttcaac     180
accagcgtgg tgtacaagaa accctgttc gtggagttca ccgaccacct gttcaatatc     240
gccaagccca ggcccccctg gatgggcctg ctgggcccca ccatccaggc cgaggtgtac     300
gacaccgtgg tgatcaccct gaagaacatg gccagccacc ccgtgagcct gcacgccgtg     360
ggcgtgagct actggaaggc cagcgagggc gccgagtacg acgaccagac cagccagcgg     420
gagaaagaag atgacaaggt gttccctggc ggcagccaca cctacgtgtg gcaggtgctg     480
aaagaaaacg cccccatggc ctccgacccc ctgtgcctga cctacagcta cctgagccac     540
gtggacctgg tgaaggacct gaacagcggc ctgatcggcg ctctgctcgt ctgccgggag     600
ggcagcctgg ccaaagagaa acccagacc ctgcacaagt tcatcctgct gttcgccgtg     660
ttcgacgagg gcaagagctg gcacagcgag acaaagaaca gcctgatgca ggaccgggac     720
gccgcctctg ccagagcctg gcccaagatg cacaccgtga acggctacgt gaacagaagc     780
ctgcccggcc tgattggctg ccaccggaag agcgtgtact ggcacgtgat cggcatgggc     840
accacacccg aggtgcacag catctttctg gaagggcaca cctttctggt ccggaaccac     900
cggcaggcca gcctggaaat cagccctatc accttcctga ccgcccagac actgctgatg     960
gacctgggcc agttcctgct gttttgccac atcagctctc accagcacga cggcatggaa    1020
gcctacgtga aggtggactc ttgccccgag gaacccagc tgcggatgaa gaacaacgag    1080
gaagccgagg actacgacga cgacctgacc gacagcgaga tggacgtggt gcggttcgac    1140
gacgacaaca gccccagctt catccagatc agaagcgtgg ccaagaagca ccccaagacc    1200
tgggtgcact atatcgccgc cgaggaagag gactgggact acgccccct ggtgctggcc    1260 cccgacgaca gaagctacaa gagccagtac ctgaacaatg gccccagcg gatcggccgg    1320 aagtacaaga agtgcggtt catggcctac accgacgaga cattcaagac ccggggaggcc    1380 atccagcacg agagcggcat cctgggcccc ctgctgtacg cgaagtggg cgacacactg    1440 ctgatcatct tcaagaacca ggctagccgg ccctacaaca tctaccccca cggcatcacc    1500
gacgtgcggc cctgtacag caggcggctg cccaagggcg tgaagcacct gaaggacttc    1560
cccatcctgc ccggcgagat cttcaagtac aagtggaccg tgaccgtgga ggacggcccc    1620
accaagagcg accccagatg cctgaccgg tactacagca gcttcgtgaa catggaacgg    1680
gacctggcct ccgggctgat cggacctctg ctgatctgct acaaagaaag cgtggaccag    1740
cggggcaacc agatcatgag cgacaagcgg aacgtgatcc tgttcagcgt gttcgatgag    1800
aaccggtcct ggtatctgac cgagaacatc cagcggtttc tgcccaaccc tgccggcgtg    1860
cagctggaag atcccgagtt ccaggccagc aacatcatgc actccatcaa tggctacgtg    1920
ttcgactctc tgcagctctc cgtgtgtctg cacgaggtgg cctactggta catcctgagc    1980
atcggcgccc agaccgactt cctgagcgtg ttcttcagcg gctacacctt caagcacaag    2040
atggtgtacg aggacaccct gaccctgttc cctttcagcg gcgagacagt gttcatgagc    2100
atggaaaacc ccggcctgtg gattctgggc tgccacaaca gcgacttccg gaaccggggc    2160
atgaccgccc tgctgaaggt gtccagctgc gacaagaaca ccggcgacta ctacgaggac    2220
agctacgagg atatcagcgc ctacctgctg tccaagaaca cgccatcga accccggagc    2280 ttcagccaga accccccgt gctgacgcgt agcttcagcc agaacagccg gcaccccagc    2340
```

```
acccggcaga agcagttcaa cgccaccacc atccccgaga acgacatcga gaaaaccgac    2400
ccttggtttg cccaccggac ccccatgccc aagatccaga acgtgtccag cagcgacctg    2460
ctgatgctgc tgcggcagag ccccacccct cacggcctga gcctgagcga cctgcaggaa    2520
gccaagtacg agacattcag cgacgacccc agccctggcg ccatcgacag caacaacagc    2580
ctgtccgaga tgacccactt ccggcccag ctgcaccaca gcggcgacat ggtgttcacc    2640
cccgagagcg gcctgcagct gcggctgaac agagaagctgg gcaccaccgc cgccaccgag    2700
ctgaagaagc tggacttcaa ggtctccagc accagcaaca acctgatcag caccatcccc    2760
agcgacaacc tggccgctgg caccgacaac accagcagcc tgggccctcc cagcatgccc    2820
gtgcactacg acagccagct ggacaccacc ctgttcggca agaagtccag cccctgacc    2880 gagtccggcg acccctgtc cctgagcgag aaaacaacg acagcaagct gctgaaaagc    2940
ggcctgatga acagccagga aagcagctgg ggcaagaatg tgtccagcac gcgtcaccag    3000
cgggagatca cccggacaac cctgcagtcc gaccaggaag agatcgatta cgacgacacc    3060
atcagcgtgg agatgaagaa agaggatttc gatatctacg acgaggacga gaaccagagc    3120
cccagaagct tccagaagaa aacccggcac tacttcattg ccgccgtgga gaggctgtgg    3180
gactacggca tgagttctag ccccccacgtg ctgcggaacc gggcccagag cggcagcgtg    3240
ccccagttca agaaagtggt gttccaggaa ttcacagacg gcagcttcac ccagcctctg    3300
tatagaggcg agctgaacga gcacctgggg ctgctggggc cctacatcag ggccgaagtg    3360
gaggacaaca tcatggtgac cttccggaat caggccagca gacccactc cttctacagc    3420 agcctgatca gctacgaaga ggaccagcgg cagggcgccg aaccccggaa gaacttcgtg    3480
aagcccaacg aaaccaagac ctacttctgg aaagtgcagc accacatggc ccccaccaag    3540
gacgagttcg actgcaaggc ctgggcctac ttcagcgacg tggatctgga aaaggacgtg    3600
cactctggac tgattggccc actcctggtc tgccacacta caccctcaa cccgcccac    3660 ggccgccagg tgaccgtgca ggaattcgcc ctgttcttca ccatcttcga cgagacaaag    3720
tcctggtact tcaccgagaa tatgaacgg aactgcagag ccccctgcaa catccagatg    3780
gaagatccta ccttcaaaga gaactaccgg ttccacgcca tcaacggcta catcatggac    3840
accctgcctg gctggtgat ggcccaggac cagagaatcc ggtggtatct gctgtccatg    3900
ggcagcaacg agaatatcca cagcatccac ttcagcggcc acgtgttcac cgtgcggaag    3960
aaagaagagt acaagatggc cctgtacaac ctgtaccccg gcgtgttcga cagtggag    4020 atgctgccca gcaaggccgg catctggcgg gtggagtgtc tgatcggcga gcacctgcac    4080
gctggcatga gcaccctgtt tctggtgtac agcaacaagt gccagacccc actgggcatg    4140
gcctctggcc acatccggga cttccagatc ccgcctccg gccagtacgg ccagtgggcc    4200
cccaagctgg ccagactgca ctacagcggc agcatcaacg cctggtccac caaagagccc    4260
ttcagctgga tcaaggtgga cctgctgcc cctatgatca tccacggcat taagacccag    4320
ggcgccaggc agaagttcag cagcctgtac atcagccagt tcatcatcat gtacagcctg    4380
gacggcaaga gtggcagac ctaccggggc aacagcaccg gcaccctgat ggtgttcttc    4440
ggcaatgtgg acagcagcgg catcaagcac aacatcttca cccccccat cattgcccgg    4500 tacatccggc tgcacccac ccactacagc attagatcca cactgagaat ggaactgatg    4560
ggctgcgacc tgaactcctg cagcatgcct ctgggcatgg aaagcaaggc catcagcgac    4620
gcccagatca cagccagcag ctacttcacc aacatgttcg ccacctggtc cccctccaag    4680
```

```
gccaggctgc acctgcaggg ccggtccaac gcctggcggc ctcaggtcaa caaccccaaa    4740
gaatggctgc aggtggactt tcagaaaacc atgaaggtga ccggcgtgac cacccagggc    4800
gtgaaaagcc tgctgaccag catgtacgtg aaagagtttc tgatcagcag ctctcaggat    4860
ggccaccagt ggaccctgtt ctttcagaac ggcaaggtga agtgttcca gggcaaccag    4920 gactccttca ccccgtggt gaactccctg accccccc tgctgacccg ctacctgaga    4980
atccaccccc agtcttgggt gcaccagatc gccctcagga tggaagtcct gggatgtgag    5040
gcccaggatc tgtactgatg a                                              5061
```

<210> SEQ ID NO 5
<211> LENGTH: 4377
<212> TYPE: DNA
<213> ORGANISM: Artificial sequence
<220> FEATURE:
<223> OTHER INFORMATION: Codon optimised modified factor VIII nucleotide
      sequence

<400> SEQUENCE: 5

```
atgcagatcg agctgtccac ctgctttttt ctgtgcctgc tgcggttctg cttcagcgcc      60
acccggcggt actacctggg cgccgtggag ctgtcctggg actacatgca gagcgacctg     120
ggcgagctgc ccgtggacgc ccggttcccc ccagagtgc ccaagagctt ccccttcaac     180
accagcgtgg tgtacaagaa aaccctgttc gtggagttca ccgaccacct gttcaatatc     240
gccaagccca ggccccctg gatgggcctg ctgggcccca ccatccaggc cgaggtgtac     300
gacaccgtgg tgatcaccct gaagaacatg gccagccacc ccgtgagcct gcacgccgtg     360
ggcgtgagct actggaaggc cagcgagggc gccgagtacg acgaccagac cagccagcgg     420
gagaaagaag atgacaaggt gttccctggc ggcagccaca cctacgtgtg gcaggtgctg     480
aaagaaaacg gccccatggc ctccgacccc ctgtgcctga cctacagcta cctgagccac     540
gtggacctgg tgaaggacct gaacagcggc ctgatcggcg ctctgctcgt ctgccgggag     600
ggcagcctgg ccaaagagaa acccagacc ctgcacaagt tcatcctgct gttcgccgtg     660
ttcgacgagg gcaagagctg gcacagcgag acaaagaaca gcctgatgca ggaccgggac     720
gccgcctctg ccagagcctg gccaagatg cacaccgtga acggctacgt gaacagaagc     780
ctgcccggcc tgattggctg ccaccggaag agcgtgtact ggcacgtgat cggcatgggc     840
accacacccg aggtgcacag catctttctg gaagggcaca cctttctggt ccggaaccac     900
cggcaggcca gctggaaat cagcccctatc accttcctga ccgcccagac actgctgatg     960
gacctgggcc agttcctgct gttttgccac atcagctctc accagcacga cggcatggaa    1020
gcctacgtga aggtggactc ttgccccgag gaacccagc tgcggatgaa gaacaacgag    1080
gaagccgagg actacgacga cgacctgacc gacagcgaga tggacgtggt gcggttcgac    1140
gacgacaaca gccccagctt catccagatc agaagcgtgg ccaagaagca cccaagacc    1200 tgggtgcact atatcgccgc cgaggaagag actgggact acgcccccct ggtgctggcc    1260
cccgacgaca gaagctacaa gagccagtac ctgaacaatg ccccccagcg gatcggccgg    1320
aagtacaaga agtgcggtt catggcctac accgacgaga cattcaagac ccgggaggcc    1380
atccagcacg agagcggcat cctgggccc tgctgtacg cgaagtgggc gacacactg    1440 ctgatcatct tcaagaacca ggctagccgg ccctacaaca tctaccccca cggcatcacc    1500
gacgtgcggc cctgtacag caggcggctg ccaagggcg tgaagcacct gaaggacttc    1560
cccatcctgc ccggcgagat cttcaagtac aagtggaccg tgaccgtgga ggacggcccc    1620
```

-continued

```
accaagagcg accccagatg cctgacccgg tactacagca gcttcgtgaa catggaacgg    1680
gacctggcct ccgggctgat cggacctctg ctgatctgct acaaagaaag cgtggaccag    1740
cggggcaacc agatcatgag cgacaagcgg aacgtgatcc tgttcagcgt gttcgatgag    1800
aaccggtcct ggtatctgac cgagaacatc cagcggtttc tgcccaaccc tgccggcgtg    1860
cagctggaag atcccgagtt ccaggccagc aacatcatgc actccatcaa tggctacgtg    1920
ttcgactctc tgcagctctc cgtgtgtctg cacgaggtgg cctactggta catcctgagc    1980
atcggcgccc agaccgactt cctgagcgtg ttcttcagcg gctacacctt caagcacaag    2040
atggtgtacg aggacaccct gaccctgttc cctttcagcg cgagacagt gttcatgagc    2100 atggaaaacc ccggcctgtg gattctgggc tgccacaaca gcgacttccg gaaccggggc    2160
atgaccgccc tgctgaaggt gtccagctgc gacaagaaca ccggcgacta ctacgaggac    2220
agctacgagg atatcagcgc ctacctgctg tccaagaaca acgccatcga accccggagc    2280
ttcagccaga accccccgt gctgacgcgt caccagcggg agatcacccg gacaaccctg    2340
cagtccgacc aggaagagat cgattacgac gacaccatca gcgtggagat gaagaaagag    2400
gatttcgata tctacgacga ggacgagaac cagagcccca gaagcttcca gaagaaaacc    2460
cggcactact tcattgccgc cgtggagagg ctgtgggact acggcatgag ttctagcccc    2520
cacgtgctgc ggaaccgggc ccagagcggc agcgtgcccc agttcaagaa agtggtgttc    2580
caggaattca cagacggcag cttcacccag cctctgtata gaggcgagct gaacgagcac    2640
ctggggctgc tggggcccta catcagggcc gaagtggagg acaacatcat ggtgaccttc    2700
cggaatcagg ccagcagacc ctactccttc tacagcagcc tgatcagcta cgaagaggac    2760
cagcggcagg cgccgaacc ccggaagaac ttcgtgaagc ccaacgaaac caagacctac    2820
ttctggaaag tgcagcacca catggccccc accaaggacg agttcgactg caaggcctgg    2880
gcctacttca gcgacgtgga tctggaaaag gacgtgcact ctggactgat tggcccactc    2940
ctggtctgcc acactaacac cctcaacccc gcccacggcc gccaggtgac cgtgcaggaa    3000
ttcgccctgt tcttcaccat cttcgacgag acaaagtcct ggtacttcac cgagaatatg    3060
gaacggaact gcagagcccc ctgcaacatc cagatggaag atcctacctt caaagagaac    3120
taccggttcc acgccatcaa cggctacatc atggacaccc tgcctggcct ggtgatggcc    3180
caggaccaga gaatccggtg gtatctgctg tccatgggca gcaacgagaa tatccacagc    3240
atccacttca gcggccacgt gttcaccgtg cggaagaaag aagagtacaa gatggcactg    3300
tacaacctgt accccggcgt gttcgagaca gtggagatgc tgcccagcaa ggccggcatc    3360
tggcgggtgg agtgtctgat cggcgagcac ctgcacgctg gcatgagcac cctgtttctg    3420
gtgtacagca caagtgcca gaccccactg ggcatggcct ctggccacat ccgggacttc    3480
cagatcaccg cctccggcca gtacggccag tgggccccca gctggccag actgcactac    3540 agcggcagca tcaacgcctg gtccaccaaa gagcccttca gctggatcaa ggtggacctg    3600
ctggccccta tgatcatcca cggcattaag acccagggcg ccaggcagaa gttcagcagc    3660
ctgtacatca gccagttcat catcatgtac agcctggacg gcaagaagtg gcagacctac    3720
cggggcaaca gcaccggcac cctgatggtg ttcttcggca atgtggacag cagcggcatc    3780
aagcacaaca tcttcaaccc cccatcatt gcccggtaca tccggctgca ccccacccac    3840
tacagcatta gatccacact gagaatggaa ctgatgggct gcgacctgaa ctcctgcagc    3900
atgcctctgg gcatggaaag caaggccatc agcgacgccc agatcacagc cagcagctac    3960
ttcaccaaca tgttcgccac ctggtccccc tccaaggcca ggctgcacct gcagggccgg    4020
```

```
tccaacgcct ggcggcctca ggtcaacaac cccaaagaat ggctgcaggt ggactttcag    4080
aaaaccatga aggtgaccgg cgtgaccacc cagggcgtga aaagcctgct gaccagcatg    4140
tacgtgaaag agtttctgat cagcagctct caggatggcc accagtggac cctgttcttt    4200
cagaacggca aggtgaaagt gttccagggc aaccaggact ccttcacccc cgtggtgaac    4260
tccctggacc ccccctgct gacccgctac ctgagaatcc accccagtc ttgggtgcac     4320 cagatcgccc tcaggatgga agtcctggga tgtgaggccc aggatctgta ctgatga      4377
```

<210> SEQ ID NO 6
<211> LENGTH: 4980
<212> TYPE: DNA
<213> ORGANISM: Artificial sequence
<220> FEATURE:
<223> OTHER INFORMATION: Codon optimised modified factor VIII nucleotide sequence

<400> SEQUENCE: 6

```
atgcagatcg agctgtccac ctgctttttt ctgtgcctgc tgcggttctg cttcagcgcc     60
acccggcggt actacctggg cgccgtggag ctgtcctggg actacatgca gagcgacctg    120
ggcgagctgc ccgtgacgc ccggttcccc ccagagtgc ccaagagctt ccccttcaac      180
accagcgtgg tgtacaagaa aaccctgttc gtggagttca ccgaccacct gttcaatatc    240
gccaagccca ggccccctg gatgggcctg ctgggcccca ccatccaggc cgaggtgtac    300
gacaccgtgg tgatcaccct gaagaacatg gccagccacc ccgtgagcct gcacgccgtg    360
ggcgtgagct actggaaggc cagcgagggc gccgagtacg acgaccagac cagccagcgg    420 gagaagaag atgacaaggt gttccctggc ggcagccaca cctacgtgtg gcaggtgctg     480
aaagaaaacg cccccatggc ctccgacccc ctgtgcctga cctacagcta cctgagccac    540
gtggacctgg tgaaggacct gaacagcggc ctgatcggcg ctctgctcgt ctgccgggag    600
ggcagcctgc ccaaagagaa acccagacc tgcacaagt tcatcctgct gttcgccgtg      660
ttcgacgagg gcaagagctg gcacagcgag acaaagaaca gcctgatgca ggaccgggac    720
gccgcctctg ccagagcctg gcccaagatg cacaccgtga acggctacgt gaacagaagc    780
ctgcccggcc tgattggctg ccaccggaag agcgtgtact ggcacgtgat cggcatgggc    840
accacacccg aggtgcacag catctttctg gaagggcaca cctttctggt ccggaaccac    900
cggcaggcca gcctggaaat cagccctatc accttcctga ccgcccagac actgctgatg    960
gacctgggcc agttcctgct gttttgccac atcagctctc accagcacga cggcatggaa   1020
gcctacgtga aggtggactc ttgccccgag gaaccccagc tgcggatgaa gaacaacgag   1080
gaagccgagg actacgacga cgacctgacc gacagcgaga tggacgtggt gcggttcgac   1140
gacgacaaca gccccagctt catccagatc agaagcgtgg ccaagaagca ccccaagacc   1200
tgggtgcact atatcgccgc cgaggaagag actgggact acgccccct ggtgctggcc    1260 cccgacgaca agctacaa gagccagtac ctgaacaatg ccccccagcg gatcggccgg    1320
aagtacaaga agtgcggtt catggcctac accgacgaga cattcaagac ccgggaggcc   1380
atccagcacg agagcggcat cctgggcccc ctgctgtacg gcgaagtggg cgacacactg   1440
ctgatcatct tcaagaacca ggctagccgg ccctacaaca tctacccca cggcatcacc    1500 gacgtgcggc ccctgtacag caggcggctg cccaagggcg tgaagcacct gaaggacttc   1560
cccatcctgc ccggcgagat cttcaagtac aagtggaccg tgaccgtgga ggacggcccc   1620
accaagagcg accccagatg cctgacccgg tactacagca gcttcgtgaa catggaacgg   1680
```

```
gacctggcct ccgggctgat cggacctctg ctgatctgct acaaagaaag cgtggaccag    1740
cggggcaacc agatcatgag cgacaagcgg aacgtgatcc tgttcagcgt gttcgatgag    1800
aaccggtcct ggtatctgac cgagaacatc cagcggtttc tgcccaaccc tgccggcgtg    1860
cagctggaag atcccgagtt ccaggccagc aacatcatgc actccatcaa tggctacgtg    1920
ttcgactctc tgcagctctc cgtgtgtctg cacgaggtgg cctactggta catcctgagc    1980 atcgcgccc agaccgactt cctgagcgtg ttcttcagcg gctacacctt caagcacaag    2040
atggtgtacg aggacaccct gaccctgttc cctttcagcg gcgagacagt gttcatgagc    2100
atggaaaacc ccgcctgtg gattctgggc tgccacaaca gcgacttccg gaaccggggc    2160
atgaccgccc tgctgaaggt gtccagctgc gacaagaaca ccggcgacta ctacgaggac    2220
agctacgagg atatcagcgc ctacctgctg tccaagaaca cgccatcga accccggagc    2280 ttcagccaga accccccgt gctgacgcgt ggcatgcggc cagaaaccca ccgtgctg    2340 ctgaaagtgt gcaacaaggt gcccatcaac aacagcaccc acagcgtgaa caccagcacc    2400
ctgaacgcca ccgacggcag gcggtgctac ctgaagaagg tgaccctgac cccccctggc    2460
ggcgaggacg ccaacatcac ctctggcgag cgcatccccg aggacatcct ggaagagctg    2520
cagctggatg gcgaagtgac agccgcccct tccggcatcc tgagagtggg cgagcaggcc    2580
ctgcggcgga aaggcaggc cgaggacaac tccaccgact cgacatcta cagcggcgac    2640 gagggcggcg aagagcggag cgagatccag gaacgcccag ccgagaaccg gaccaccgcc    2700
aacgccaccg gcatcaaccg gaccaaagag ctggaagagg gcaacgagat cctgctgacc    2760
ggcaaccccg gcaacagcaa gcggagcttc accgtggagc ccgtgaccag cgaggaaatg    2820
gtgcagaact acatcatgtc tgaggaagag aagctgaagc cccaccatca gcagcccggc    2880
aacgtggccg tgaacgagct gtctgtgacg cgtcaccagc gggagatcac ccggacaacc    2940
ctgcagtccg accaggaaga gatcgattac gacgacacca tcagcgtgga gatgaagaaa    3000
gaggatttcg atatctacga cgaggacgag aaccagagcc cagaagctt ccagaagaaa    3060 acccggcact acttcattgc cgccgtggag aggctgtggg actacggcat gagttctagc    3120
ccccacgtgc tgcggaaccg ggcccagagc ggcagcgtgc cccagttcaa gaaagtggtg    3180
ttccaggaat tcacagacgg cagcttcacc cagcctctgt atagaggcga gctgaacgag    3240
cacctggggc tgctggggcc ctacatcagg gccgaagtgg aggacaacat catggtgacc    3300
ttccggaatc aggccagcag accctactcc ttctacagca gcctgatcag ctacgaagag    3360
gaccagcggc agggcgccga accccggaag aacttcgtga agcccaacga aaccaagacc    3420
tacttctgga aagtgcagca ccacatggcc cccaccaagg acgagttcga ctgcaaggcc    3480
tgggcctact tcagcgacgt ggatctggaa aaggacgtgc actctggact gattggccca    3540
ctcctggtct gccacactaa caccctcaac cccgcccacg gccgccaggt gaccgtgcag    3600
gaattcgccc tgttcttcac catcttcgac gagacaaagt cctggtactt caccgagaat    3660
atggaacgga actgcagagc ccctgcaac atccagatgg aagatcctac cttcaaagag    3720
aactaccggt ccacgccat caacggctac atcatggaca ccctgcctgg cctggtgatg    3780
gcccaggacc agagaatccg gtggtatctg ctgtccatgg gcagcaacga gaatatccac    3840
agcatccact tcagcggcca cgtgttcacc gtgcggaaga agaagagta caagatggcc    3900 ctgtacaacc tgtaccccgg cgtgttcgag acagtggaga tgctgcccag caaggccggc    3960
atctggcggg tggagtgtct gatcggcgag cacctgcacg ctggcatgag cacccctgttt    4020
```

```
ctggtgtaca gcaacaagtg ccagacccca ctgggcatgg cctctggcca catccgggac    4080
ttccagatca ccgcctccgg ccagtacggc cagtgggccc caagctggc cagactgcac     4140 tacagcggca gcatcaacgc ctggtccacc aaagagccct tcagctggat caaggtggac    4200
ctgctggccc ctatgatcat ccacggcatt aagacccagg gcgccaggca gaagttcagc    4260
agcctgtaca tcagccagtt catcatcatg tacagcctgg acggcaagaa gtggcagacc    4320
taccggggca cagcaccgg cacctgatg gtgttcttcg gcaatgtgga cagcagcggc      4380
atcaagcaca acatcttcaa ccccccatc attgcccggt catccggct gcacccacc       4440 cactacagca ttagatccac actgagaatg gaactgatgg gctgcgacct gaactcctgc    4500
agcatgcctc tgggcatgga aagcaaggcc atcagcgacg cccagatcac agccagcagc    4560
tacttcacca acatgttcgc cacctggtcc cctccaagg ccaggctgca cctgcagggc     4620
cggtccaacg cctggcggcc tcaggtcaac aaccccaaag aatggctgca ggtggacttt    4680
cagaaaacca tgaaggtgac cggcgtgacc acccagggcg tgaaaagcct gctgaccagc    4740
atgtacgtga aagagtttct gatcagcagc tctcaggatg ccaccagtg gaccctgttc     4800 tttcagaacg gcaaggtgaa agtgttccag ggcaaccagg actccttcac ccccgtggtg    4860
aactccctgg accccccct gctgaccgc tacctgagaa tccaccccca gtcttgggtg      4920
caccagatcg ccctcaggat ggaagtcctg ggatgtgagg cccaggatct gtactgatga    4980
```

<210> SEQ ID NO 7
<211> LENGTH: 5336
<212> TYPE: DNA
<213> ORGANISM: Artificial sequence
<220> FEATURE:
<223> OTHER INFORMATION: Codon optimised modified factor VIII nucleotide sequence

<400> SEQUENCE: 7

```
tgtttgctgc ttgcaatgtt tgcccatttt agggtggaca caggacgctg tggtttctga      60
gccagggggc gactcagatc ccagccagtg gacttagccc ctgtttgctc ctccgataac     120
tggggtgacc ttggttaata ttcaccagca gcctcccccg ttgcccctct ggatccactg    180
cttaaatacg gacgaggaca gggccctgtc tcctcagctt caggcaccac cactgacctg    240
ggacagtgaa tcgcggccgc caccatgcag attgagctga gcacctgctt cttcctgtgc    300
ctgctgaggt tctgcttctc tgccaccagg agatactacc tggggggctgt ggagctgagc    360 tgggactaca tgcagtctga cctgggggag ctgcctgtgg atgccaggtt ccccccagag    420
gtgcccaaga gcttccccct caacacctct gtggtgtaca agaagaccct gtttgtggag    480
ttcactgacc acctgttcaa cattgccaag cccaggcccc cctggatggg cctgctgggc    540
cccaccatcc aggctgaggt gtatgacact gtggtgatca ccctgaagaa catgccagc    600 caccctgtga gcctgcatgc tgtggggtgt agctactgga aggcctctga ggggctgag     660 tatgatgacc agaccagcca gagggagaag gaggatgaca agtgttccc tggggggcagc    720 cacacctatg tgtggcaggt gctgaaggag aatggcccca tggcctctga ccccctgtgc    780
ctgacctaca gctacctgag ccatgtggac ctggtgaagg acctgaactc tggcctgatt    840
ggggccctgc tggtgtgcag ggagggcagc ctggccaaga gaagaccca gcccctgcac    900 aagttcatcc tgctgtttgc tgtgtttgat gagggcaaga gctggcactc tgaaaccaag    960
aacagcctga tgcaggacag ggatgctgcc tctgccaggg cctggccaa gatgcacact    1020 gtgaatggct atgtgaacag gagcctgcct ggcctgattg gctgccacag gaagtctgtg    1080
```

```
tactggcatg tgattggcat gggcaccacc cctgaggtgc acagcatctt cctggagggc    1140
cacaccttcc tggtcaggaa ccacaggcag gccagcctgg agatcagccc catcaccttc    1200
ctgactgccc agaccctgct gatggacctg gccagttcc tgctgttctg ccacatcagc     1260
agccaccagc atgatggcat ggaggcctat gtgaaggtgg acagctgccc tgaggagccc    1320
cagctgagga tgaagaacaa tgaggaggct gaggactatg atgatgacct gactgactct    1380
gagatggatg tggtgaggtt tgatgatgac aacagcccca gcttcatcca gatcaggtct    1440
gtggccaaga agcaccccaa gacctgggtg cactacattg ctgctgagga ggaggactgg    1500
gactatgccc cctggtgct ggcccctgat gacaggagct acaagagcca gtacctgaac     1560
aatggccccc agaggattgg caggaagtac aagaaggtca ggttcatggc ctacactgat    1620
gaaaccttca agaccaggga ggccatccag catgagtctg gcatcctggg cccctgctg     1680 tatggggagg tgggggacac cctgctgatc atcttcaaga accaggccag caggccctac    1740
aacatctacc cccatggcat cactgatgtg aggcccctgt acagcaggag gctgcccaag    1800 gggtgaagc acctgaagga cttccccatc ctgcctgggg agatcttcaa gtacaagtgg    1860
actgtgactg tggaggatgg ccccaccaag tctgaccccca ggtgcctgac cagatactac   1920
agcagctttg tgaacatgga gagggacctg gcctctggcc tgattggccc cctgctgatc    1980
tgctacaagg agtctgtgga ccagaggggc aaccagatca tgtctgacaa gaggaatgtg    2040
atcctgttct ctgtgtttga tgagaacagg agctggtacc tgactgagaa catccagagg    2100
ttcctgccca accctgctgg ggtgcagctg gaggaccctg agttccaggc cagcaacatc    2160
atgcacagca tcaatggcta tgtgtttgac agcctgcagc tgtctgtgtg cctgcatgag    2220
gtggcctact ggtacatcct gagcattggg gcccagactg acttcctgtc tgtgttcttc    2280
tctggctaca ccttcaagca caagatggtg tatgaggaca ccctgaccct gttcccttc     2340 tctggggaga ctgtgttcat gagcatggag aaccctggcc tgtggattct gggctgccac    2400
aactctgact tcaggaacag gggcatgact gccctgctga agtctccag ctgtgacaag     2460 aacactgggg actactatga ggacagctat gaggacatct ctgcctacct gctgagcaag    2520
aacaatgcca ttgagcccag gagcttcagc cagaacagca ggcacccag caccaggcag     2580 aagcagttca atgccaccac catccctgag aatgacatag agaagacaga cccatggttt    2640
gcccaccgga cccccatgcc caagatccag aatgtgagca gctctgacct gctgatgctg    2700
ctgaggcaga gccccacccc catggcctg agcctgtctg acctgcagga ggccaagtat     2760
gaaaccttct ctgatgaccc cagccctggg gccattgaca gcaacaacag cctgtctgag    2820
atgacccact tcaggcccca gctgcaccac tctggggaca tggtgttcac ccctgagtct    2880
ggcctgcagc tgaggctgaa tgagaagctg ggcaccactg ctgccactga gctgaagaag    2940
ctggacttca agtctccag caccagcaac aacctgatca gcaccatccc ctctgacaac    3000
ctggctgctg gcactgacaa caccagcagc ctgggccccc ccagcatgcc tgtgcactat    3060
gacagccagc tggacaccac cctgtttggc aagaagagca gccccctgac tgagtctggg    3120
ggccccctga gcctgtctga ggagaacaat gacagcaagc tgctggagtc tggcctgatg    3180
aacagccagg agagcagctg gggcaagaat gtgagcagca gggagatcac caggaccacc    3240
ctgcagtctg accaggagga gattgactat gatgacacca tctctgtgga tgaagaagag    3300
gaggactttg acatctacga cgaggacgag aaccagagcc caggagcttc cagaagaag    3360 accaggcact acttcattgc tgctgtggag aggctgtggg actatggcat gagcagcagc    3420
ccccatgtgc tgaggaacag ggcccagtct ggctctgtgc cccagttcaa gaaggtggtg    3480
```

```
ttccaggagt tcactgatgg cagcttcacc cagcccctgt acagagggga gctgaatgag    3540
cacctgggcc tgctgggccc ctacatcagg gctgaggtgg aggacaacat catggtgacc    3600
ttcaggaacc aggccagcag gccctacagc ttctacagca gcctgatcag ctatgaggag    3660
gaccagaggc aggggctga gcccaggaag aactttgtga agcccaatga aaccaagacc    3720
tacttctgga aggtgcagca ccacatggcc cccaccaagg atgagtttga ctgcaaggcc    3780
tgggcctact tctctgatgt ggacctggag aaggatgtgc actctggcct gattggcccc    3840
ctgctggtgt gccacaccaa cccctgaac cctgcccatg gcaggcaggt gactgtgcag    3900
gagtttgccc tgttcttcac catctttgat gaaaccaaga gctggtactt cactgagaac    3960
atggagagga actgcagggc cccctgcaac atccagatgg aggaccccac cttcaaggag    4020
aactacaggt tccatgccat caatggctac atcatggaca ccctgcctgg cctggtgatg    4080
gcccaggacc agaggatcag gtggtacctg ctgagcatgg gcagcaatga gaacatccac    4140
agcatccact tctctggcca tgtgttcact gtgaggaaga aggaggagta caagatggcc    4200
ctgtacaacc tgtaccctgg ggtgtttgag actgtggaga tgctgcccag caaggctggc    4260
atctggaggg tggagtgcct gattggggag caccctgcatg ctggcatgag cacctgttc    4320 ctggtgtaca gcaacaagtg ccagaccccc ctgggcatgg cctctggcca catcagggac    4380
ttccagatca ctgcctctgg ccagtatggc cagtgggccc caagctggc caggctgcac    4440 tactctggca gcatcaatgc ctggagcacc aaggagccct cagctggat caaggtggac    4500 ctgctggccc ccatgatcat ccatggcatc aagacccagg gggccaggca gaagttcagc    4560
agcctgtaca tcagccagtt catcatcatg tacagcctgg atggcaagaa gtggcagacc    4620
tacaggggca acagcactgg cacccctgatg gtgttctttg gcaatgtgga cagctctggc    4680
atcaagcaca acatcttcaa cccccccatc attgccagat acatcaggct gcaccccacc    4740
cactacagca tcaggagcac cctgaggatg gagctgatgg gctgtgacct gaacagctgc    4800
agcatgcccc tgggcatgga gagcaaggcc atctctgatg cccagatcac tgccagcagc    4860
tacttcacca acatgtttgc cacctggagc cccagcaagg ccaggctgca cctgcagggc    4920
aggagcaatg cctggaggcc ccaggtcaac aaccccaagg agtggctgca ggtggacttc    4980
cagaagacca tgaaggtgac tggggtgacc acccaggggg tgaagagcct gctgaccagc    5040
atgtatgtga aggagttcct gatcagcagc agccaggatg ccaccagtga ccctgttc    5100 ttccagaatg gcaaggtgaa ggtgttccag ggcaaccagg acagcttcac ccctgtggtg    5160
aacagcctgg accccccct gctgaccaga tacctgagga ttcaccccca gagctgggtg    5220
caccagattg ccctgaggat ggaggtgctg gctgtgagg cccaggacct gtactgatcg    5280
cgaataaaag atctttattt tcattagatc tgtgtgttgg ttttttgtgt gatgca         5336
```

<210> SEQ ID NO 8
<211> LENGTH: 42
<212> TYPE: DNA
<213> ORGANISM: Artificial sequence
<220> FEATURE:
<223> OTHER INFORMATION: Synthetic construct

<400> SEQUENCE: 8

```
agcttcagcc agaacccccc cgtgctgacg cgtcaccagc gg                         42
```

<210> SEQ ID NO 9
<211> LENGTH: 20
<212> TYPE: DNA

```
<213> ORGANISM: Artificial sequence
<220> FEATURE:
<223> OTHER INFORMATION: Primer

<400> SEQUENCE: 9
tgtgtgcccg tctgttgtgt                                               20

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
gagtcctgcg tcgagagagc                                               20

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
cgcccgaaca gggacttgaa                                               20

<210> SEQ ID NO 12
<211> LENGTH: 21
<212> TYPE: DNA
<213> ORGANISM: Artificial sequence
<220> FEATURE:
<223> OTHER INFORMATION: Primer

<400> SEQUENCE: 12
aaaacgagca gtgacctgag g                                             21

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
ttcagtcatg ctgctagcgc                                               20

<210> SEQ ID NO 14
<211> LENGTH: 22
<212> TYPE: DNA
<213> ORGANISM: Artificial sequence
<220> FEATURE:
<223> OTHER INFORMATION: Primer

<400> SEQUENCE: 14
tgcacggaat ctcgtctcag tc                                            22

<210> SEQ ID NO 15
<211> LENGTH: 25
<212> TYPE: DNA
<213> ORGANISM: Artificial sequence
<220> FEATURE:
<223> OTHER INFORMATION: Primer

<400> SEQUENCE: 15
tcacccacaa gttgcccatc tacga                                         25
```

```
<210> SEQ ID NO 16
<211> LENGTH: 25
<212> TYPE: DNA
<213> ORGANISM: Artificial sequence
<220> FEATURE:
<223> OTHER INFORMATION: Primer

<400> SEQUENCE: 16
cagcggaacc gctcattgcc aatgg                                              25

<210> SEQ ID NO 17
<211> LENGTH: 26
<212> TYPE: DNA
<213> ORGANISM: Artificial sequence
<220> FEATURE:
<223> OTHER INFORMATION: Primer

<400> SEQUENCE: 17
atgccctccc ccatgccatc ctgcgt                                             26

<210> SEQ ID NO 18
<211> LENGTH: 14
<212> TYPE: PRT
<213> ORGANISM: Artificial sequence
<220> FEATURE:
<223> OTHER INFORMATION: Synthetic construct

<400> SEQUENCE: 18

Ser Phe Ser Gln Asn Pro Pro Val Leu Thr Arg His Gln Arg
1               5                   10

<210> SEQ ID NO 19
<211> LENGTH: 11
<212> TYPE: PRT
<213> ORGANISM: Artificial sequence
<220> FEATURE:
<223> OTHER INFORMATION: Synthetic construct

<400> SEQUENCE: 19

Ser Phe Ser Gln Asn Pro Pro Val Leu Thr Arg
1               5                   10

<210> SEQ ID NO 20
<211> LENGTH: 5
<212> TYPE: PRT
<213> ORGANISM: Artificial sequence
<220> FEATURE:
<223> OTHER INFORMATION: Synthetic construct

<400> SEQUENCE: 20

Thr Arg His Gln Arg
1               5

<210> SEQ ID NO 21
<211> LENGTH: 1670
<212> TYPE: PRT
<213> ORGANISM: Artificial sequence
<220> FEATURE:
<223> OTHER INFORMATION: Modified Factor VIII protein

<400> SEQUENCE: 21

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30
```

```
Trp Asp Tyr Met Gln Ser Asp Leu Gly Glu Leu Pro Val Asp Ala Arg
         35                  40                  45

Phe Pro Pro Arg Val Pro Lys Ser Phe Pro Phe Asn Thr Ser Val Val
 50                  55                  60

Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                 85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
                115                 120                 125

Glu Gly Ala Glu Tyr Asp Asp Gln Thr Ser Gln Arg Glu Lys Glu Asp
130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
                180                 185                 190

Gly Ala Leu Leu Val Cys Arg Glu Gly Ser Leu Ala Lys Glu Lys Thr
                195                 200                 205

Gln Thr Leu His Lys Phe Ile Leu Leu Phe Ala Val Phe Asp Glu Gly
                210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
                260                 265                 270

Tyr Trp His Val Ile Gly Met Gly Thr Thr Pro Glu Val His Ser Ile
                275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
                355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
                435                 440                 445
```

-continued

```
Ala Tyr Thr Asp Glu Thr Phe Lys Thr Arg Glu Ala Ile Gln His Glu
            450             455             460
Ser Gly Ile Leu Gly Pro Leu Leu Tyr Gly Glu Val Gly Asp Thr Leu
465             470             475             480
Leu Ile Ile Phe Lys Asn Gln Ala Ser Arg Pro Tyr Asn Ile Tyr Pro
                485             490             495
His Gly Ile Thr Asp Val Arg Pro Leu Tyr Ser Arg Arg Leu Pro Lys
            500             505             510
Gly Val Lys His Leu Lys Asp Phe Pro Ile Leu Pro Gly Glu Ile Phe
                515             520             525
Lys Tyr Lys Trp Thr Val Thr Val Glu Asp Gly Pro Thr Lys Ser Asp
530             535             540
Pro Arg Cys Leu Thr Arg Tyr Tyr Ser Ser Phe Val Asn Met Glu Arg
545             550             555             560
Asp Leu Ala Ser Gly Leu Ile Gly Pro Leu Leu Ile Cys Tyr Lys Glu
                565             570             575
Ser Val Asp Gln Arg Gly Asn Gln Ile Met Ser Asp Lys Arg Asn Val
            580             585             590
Ile Leu Phe Ser Val Phe Asp Glu Asn Arg Ser Trp Tyr Leu Thr Glu
        595             600             605
Asn Ile Gln Arg Phe Leu Pro Asn Pro Ala Gly Val Gln Leu Glu Asp
    610             615             620
Pro Glu Phe Gln Ala Ser Asn Ile Met His Ser Ile Asn Gly Tyr Val
625             630             635             640
Phe Asp Ser Leu Gln Leu Ser Val Cys Leu His Glu Val Ala Tyr Trp
                645             650             655
Tyr Ile Leu Ser Ile Gly Ala Gln Thr Asp Phe Leu Ser Val Phe Phe
            660             665             670
Ser Gly Tyr Thr Phe Lys His Lys Met Val Tyr Glu Asp Thr Leu Thr
            675             680             685
Leu Phe Pro Phe Ser Gly Glu Thr Val Phe Met Ser Met Glu Asn Pro
        690             695             700
Gly Leu Trp Ile Leu Gly Cys His Asn Ser Asp Phe Arg Asn Arg Gly
705             710             715             720
Met Thr Ala Leu Leu Lys Val Ser Ser Cys Asp Lys Asn Thr Gly Asp
                725             730             735
Tyr Tyr Glu Asp Ser Tyr Glu Asp Ile Ser Ala Tyr Leu Leu Ser Lys
            740             745             750
Asn Asn Ala Ile Glu Pro Arg Ser Phe Ser Gln Asn Ser Arg His Pro
            755             760             765
Ser Thr Arg Gln Lys Gln Phe Asn Ala Thr Thr Ile Pro Glu Asn Asp
770             775             780
Ile Glu Lys Thr Asp Pro Trp Phe Ala His Arg Thr Pro Met Pro Lys
785             790             795             800
Ile Gln Asn Val Ser Ser Ser Asp Leu Leu Met Leu Leu Arg Gln Ser
                805             810             815
Pro Thr Pro His Gly Leu Ser Leu Ser Asp Leu Gln Glu Ala Lys Tyr
            820             825             830
Glu Thr Phe Ser Asp Asp Pro Ser Pro Gly Ala Ile Asp Ser Asn Asn
            835             840             845
Ser Leu Ser Glu Met Thr His Phe Arg Pro Gln Leu His His Ser Gly
850             855             860
Asp Met Val Phe Thr Pro Glu Ser Gly Leu Gln Leu Arg Leu Asn Glu
```

```
                865                 870                 875                 880
Lys Leu Gly Thr Thr Ala Ala Thr Glu Leu Lys Lys Leu Asp Phe Lys
                    885                 890                 895
Val Ser Ser Thr Ser Asn Asn Leu Ile Ser Thr Ile Pro Ser Asp Asn
                    900                 905                 910
Leu Ala Ala Gly Thr Asp Asn Thr Ser Ser Leu Gly Pro Ser Met
                    915                 920                 925
Pro Val His Tyr Asp Ser Gln Leu Asp Thr Thr Leu Phe Gly Lys Lys
                    930                 935                 940
Ser Ser Pro Leu Thr Glu Ser Gly Gly Pro Leu Ser Leu Ser Glu Glu
945                 950                 955                 960
Asn Asn Asp Ser Lys Leu Leu Glu Ser Gly Leu Met Asn Ser Gln Glu
                    965                 970                 975
Ser Ser Trp Gly Lys Asn Val Ser Arg Glu Ile Thr Arg Thr Thr
                    980                 985                 990
Leu Gln Ser Asp Gln Glu Glu Ile Asp Tyr Asp Asp Thr Ile Ser Val
                    995                 1000                1005
Glu Met Lys Lys Glu Asp Phe Asp Ile Tyr Asp Glu Asp Glu Asn
        1010                1015                1020
Gln Ser Pro Arg Ser Phe Gln Lys Lys Thr Arg His Tyr Phe Ile
        1025                1030                1035
Ala Ala Val Glu Arg Leu Trp Asp Tyr Gly Met Ser Ser Ser Pro
        1040                1045                1050
His Val Leu Arg Asn Arg Ala Gln Ser Gly Ser Val Pro Gln Phe
        1055                1060                1065
Lys Lys Val Val Phe Gln Glu Phe Thr Asp Gly Ser Phe Thr Gln
        1070                1075                1080
Pro Leu Tyr Arg Gly Glu Leu Asn Glu His Leu Gly Leu Leu Gly
        1085                1090                1095
Pro Tyr Ile Arg Ala Glu Val Glu Asp Asn Ile Met Val Thr Phe
        1100                1105                1110
Arg Asn Gln Ala Ser Arg Pro Tyr Ser Phe Tyr Ser Ser Leu Ile
        1115                1120                1125
Ser Tyr Glu Glu Asp Gln Arg Gln Gly Ala Glu Pro Arg Lys Asn
        1130                1135                1140
Phe Val Lys Pro Asn Glu Thr Lys Thr Tyr Phe Trp Lys Val Gln
        1145                1150                1155
His His Met Ala Pro Thr Lys Asp Glu Phe Asp Cys Lys Ala Trp
        1160                1165                1170
Ala Tyr Phe Ser Asp Val Asp Leu Glu Lys Asp Val His Ser Gly
        1175                1180                1185
Leu Ile Gly Pro Leu Leu Val Cys His Thr Asn Thr Leu Asn Pro
        1190                1195                1200
Ala His Gly Arg Gln Val Thr Val Gln Glu Phe Ala Leu Phe Phe
        1205                1210                1215
Thr Ile Phe Asp Glu Thr Lys Ser Trp Tyr Phe Thr Glu Asn Met
        1220                1225                1230
Glu Arg Asn Cys Arg Ala Pro Cys Asn Ile Gln Met Glu Asp Pro
        1235                1240                1245
Thr Phe Lys Glu Asn Tyr Arg Phe His Ala Ile Asn Gly Tyr Ile
        1250                1255                1260
Met Asp Thr Leu Pro Gly Leu Val Met Ala Gln Asp Gln Arg Ile
        1265                1270                1275
```

Arg Trp Tyr Leu Leu Ser Met Gly Ser Asn Glu Asn Ile His Ser
1280                1285                1290

Ile His Phe Ser Gly His Val Phe Thr Val Arg Lys Lys Glu Glu
1295                1300                1305

Tyr Lys Met Ala Leu Tyr Asn Leu Tyr Pro Gly Val Phe Glu Thr
1310                1315                1320

Val Glu Met Leu Pro Ser Lys Ala Gly Ile Trp Arg Val Glu Cys
1325                1330                1335

Leu Ile Gly Glu His Leu His Ala Gly Met Ser Thr Leu Phe Leu
1340                1345                1350

Val Tyr Ser Asn Lys Cys Gln Thr Pro Leu Gly Met Ala Ser Gly
1355                1360                1365

His Ile Arg Asp Phe Gln Ile Thr Ala Ser Gly Gln Tyr Gly Gln
1370                1375                1380

Trp Ala Pro Lys Leu Ala Arg Leu His Tyr Ser Gly Ser Ile Asn
1385                1390                1395

Ala Trp Ser Thr Lys Glu Pro Phe Ser Trp Ile Lys Val Asp Leu
1400                1405                1410

Leu Ala Pro Met Ile Ile His Gly Ile Lys Thr Gln Gly Ala Arg
1415                1420                1425

Gln Lys Phe Ser Ser Leu Tyr Ile Ser Gln Phe Ile Ile Met Tyr
1430                1435                1440

Ser Leu Asp Gly Lys Lys Trp Gln Thr Tyr Arg Gly Asn Ser Thr
1445                1450                1455

Gly Thr Leu Met Val Phe Phe Gly Asn Val Asp Ser Ser Gly Ile
1460                1465                1470

Lys His Asn Ile Phe Asn Pro Pro Ile Ile Ala Arg Tyr Ile Arg
1475                1480                1485

Leu His Pro Thr His Tyr Ser Ile Arg Ser Thr Leu Arg Met Glu
1490                1495                1500

Leu Met Gly Cys Asp Leu Asn Ser Cys Ser Met Pro Leu Gly Met
1505                1510                1515

Glu Ser Lys Ala Ile Ser Asp Ala Gln Ile Thr Ala Ser Ser Tyr
1520                1525                1530

Phe Thr Asn Met Phe Ala Thr Trp Ser Pro Ser Lys Ala Arg Leu
1535                1540                1545

His Leu Gln Gly Arg Ser Asn Ala Trp Arg Pro Gln Val Asn Asn
1550                1555                1560

Pro Lys Glu Trp Leu Gln Val Asp Phe Gln Lys Thr Met Lys Val
1565                1570                1575

Thr Gly Val Thr Thr Gln Gly Val Lys Ser Leu Leu Thr Ser Met
1580                1585                1590

Tyr Val Lys Glu Phe Leu Ile Ser Ser Ser Gln Asp Gly His Gln
1595                1600                1605

Trp Thr Leu Phe Phe Gln Asn Gly Lys Val Lys Val Phe Gln Gly
1610                1615                1620

Asn Gln Asp Ser Phe Thr Pro Val Val Asn Ser Leu Asp Pro Pro
1625                1630                1635

Leu Leu Thr Arg Tyr Leu Arg Ile His Pro Gln Ser Trp Val His
1640                1645                1650

Gln Ile Ala Leu Arg Met Glu Val Leu Gly Cys Glu Ala Gln Asp
1655                1660                1665

-continued

```
Leu Tyr
    1670

<210> SEQ ID NO 22
<211> LENGTH: 20
<212> TYPE: PRT
<213> ORGANISM: Artificial Sequence
<220> FEATURE:
<223> OTHER INFORMATION: Synthetic construct

<400> SEQUENCE: 22

Glu Pro Arg Ser Phe Ser Gln Asn Pro Pro Val Leu Lys Arg His Gln
1               5                   10                  15

Arg Glu Ile Thr
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic construct

<400> SEQUENCE: 23

Glu Pro Arg Ser Phe Ser Gln Asn Pro Pro Val Leu Thr Arg His Gln
1               5                   10                  15

Arg Glu Ile Thr
            20
```

OPTIMISED CODING SEQUENCE AND PROMOTER

This application is a divisional of U.S. patent application Ser. No. 13/382,953, filed Apr. 18, 2012, which is a U.S. National Phase Application of International Application No. PCT/US2010/041378, filed Jul. 8, 2010, which claims priority to United Kingdom Application No. 0911870.4, filed Jul. 8, 2009, which is incorporated by reference herein in its entirety.

FIELD OF THE INVENTION

The invention relates to an optimised coding sequence of human blood clotting factor eight (VIII) and a new promoter, which may be used in such vectors as rAAV for introduction of factor VIII, other blood clotting factors and transgenes including those involved in the coagulation cascade, hepatocytes biology, lysosomal storage, and urea cycle disorders, lipid storage disease, alpha-1-antitrypsin, into cells to bring about expression thereof. The invention also relates to cells transformed with such vectors, proteins and glycoproteins produced by such cells, transgenically modified animals containing cells modified using the vectors and methods of treatment utilising the vectors in a gene replacement approach and using proteins and glycoproteins produced by cells transformed with the vectors in a more conventional approach.

BACKGROUND TO THE INVENTION

The inventors are interested in developing a safe and efficient gene transfer strategy for the treatment of haemophilia A (HA), the most common inherited bleeding disorder. This would represent a major clinical advance with significant implications for other congenital disorders that lack effective treatment. The inventors have already developed a promising gene therapy approach for haemophilia B using recombinant adeno-associated viral (rAAV) vectors. Haemophilia A poses several new challenges due to the distinct molecular and biochemical properties of human factor VIII (hFVIII), a molecule that is mutated in this disease. These include the relatively large size of the hFVIII cDNA and the fact that hFVIII protein expression is highly inefficient. The inventors have begun to address some of these limitations through advances in vector technology and the development of a novel more potent hFVIII variant (codop-hFVIII) that can be efficiently packaged into rAAV.

Haemophilia A (HA) is an X-linked bleeding disorder that affects approximately 1 in 5,000 males, that is caused by mutations in the factor VIII (FVIII) gene, which codes for an essential cofactor in the coagulation cascade. Severe HA patients (>50% of patients) have less than 1% of normal FVIII activity, and suffer from spontaneous haemorrhage into weight bearing joints and soft tissues, which cause permanent disability and occasionally death. The current standard of care for HA consists of recombinant hFVIII protein concentrates, which can arrest haemorrhage but do not abrogate chronic damage that ensues after a bleed. Prophylactic administration of factor concentrates to maintain plasma FVIII levels above 1% (>2 ng/ml) leads to a marked reduction in spontaneous haemorrhage and chronic arthropathy. However, the half life of FVIII is short (8-12 hours), necessitating three intravenous administration of concentrates per week. This is prohibitively expensive (>£100,000/year/patient), highly invasive and time consuming. Because of its high cost and limited supply, over 75% of severe HA patients receive no, or only sporadic treatment with FVIII concentrates. These individuals face a drastically shortened life of pain and disability.

Attention has, therefore, turned to somatic gene therapy for HA because of its potential for a cure through continuous endogenous production of FVIII following a single administration of vector. Haemophilia A, is in fact well suited for a gene replacement approach because its clinical manifestations are entirely attributable to the lack of a single gene product (FVIII) that circulates in minute amounts (200 ng/ml) in the plasma. Tightly regulated control of gene expression is not essential and a modest increase in the level of FVIII (>1% of normal) can ameliorate the severe phenotype. The availability of animal models including FVIII-knockout mice and haemophilia A dogs can facilitate extensive preclinical evaluation of gene therapy strategies. Finally, the consequences of gene transfer can be assessed using simple quantitative rather than qualitative endpoints that can be easily assayed in most clinical laboratories, which contrasts with other gene therapy targets where expression is difficult to assess or is influenced by additional factors such as substrate flux.

Three gene transfer Phase I trials have been conducted thus far for HA using direct in vivo gene delivery of onco-retro- or adenoviral vectors as well as autologous transplant of plasmid modified autologous fibroblasts. Stable expression of hFVIII at above 1% was not achieved. These and subsequent preclinical studies highlighted several critical biological obstacles to successful gene therapy of HA.

Cellular processing of the wild type full length FVIII molecule is highly complex and expression is confounded by mRNA instability, interaction with endoplasmic reticulum (ER) chaperones, and a requirement for facilitated ER to Golgi transport through interaction with the mannose-binding lectin LMAN1. Novel more potent FVIII variants have, however, been developed through incremental advances in our understanding of the biology of FVIII expression. For instance biochemical studies demonstrated that the FVIII B-domain was dispensable for FVIII cofactor activity. Deletion of the B-domain resulted in a 17-fold increase in mRNA levels over full-length wild-type FVIII and a 30% increase in secreted protein. This led to the development of B-domain deleted (BDD) FVIII protein concentrate, which is now widely used in the clinic. Recent studies, however, indicate that full length and BDD hFVIII misfold in the ER lumen, resulting in activation of the unfolded protein response (UPR) and apoptosis of murine hepatocytes. However, the addition of a short B-domain spacer, rich in asparagine-linked oligosaccharides, to BDD-FVIII (=N6-FVIII) overcomes this problem in part through improved transport from the ER to the Golgi. N6-FVIII is secreted at 10 fold higher levels than full length wild type FVIII but the inventors believe that FVIII secretion can be improved further through modification of the FVIII genome.

rAAV currently shows most promise for chronic disorders such as HA because of its excellent safety profile. In addition, the inventors and others have shown that a single administration of rAAV vector is sufficient to direct long-term transgene expression without significant toxicity in a variety of animal models including non-human primates. Integration of the rAAV provirus has been described, but at a frequency that is exceedingly low and comparable to that of plasmid DNA. Stable transgene expression is, therefore, mediated mainly by episomally retained rAAV genomes in post-mitotic tissues, thereby reducing the risk of insertional oncogenesis. This contrasts with integrating vectors that have been shown to cause a lymphoproliferative disorder in children with SCID-XI. Whilst promising results have recently been reported in patients suffering from Parkinson's disease and Leber's congenital amaurosis following rAAV mediated gene transfer, until recently the large size of the hFVIII cDNA (~7 kb), which exceeds the relatively small packaging capacity of rAAV of ~4.7 to 4.9 kb, has limited the use of this vector for HA. A recent report from Pierce and colleagues demonstrated long-term (>4 years) expression of B domain deleted (BDD) canine FVIII at 2.5-5% of normal following a single administration of rAAV in haemophilia A dogs. However, rAAV mediated expression of human FVIII has not been established to the same degree.

Currently, the most severe and challenging complication of treatment with FVIII concentrates is the development of neutralising antibodies to FVIII (FVIII inhibitors), which occurs in up to 30% of patients with HA. These inhibitors negate the biological effects of FVIII concentrates and making it difficult to treat bleeding episodes, except with bypass agents such as recombinant activated factor VII (rFVIIa). The significant cost of rFVIIa (~£500,000 per episode of orthopaedic surgery) and toxicity (e.g. thrombosis) precludes prophylactic use. Immune tolerance induction (ITI) is an alternative but this it is less effective in patients with longstanding, high titre, inhibitors. Peripheral tolerance has, in fact, been achieved in some patients with intractable FVIII inhibitors following liver transplantation, suggesting that stable long-term endogenous expression of hFVIII may be important for achieving tolerance. The inventors' data in mice and non-human primates and that of others clearly shows that liver targeted gene transfer with rAAV promotes a state of permanent tolerance towards the transgene through expansion of transgene specific regulatory T cells (Tregs). Therefore, gene transfer may provide an alternative means for prevention and eradication of intractable inhibitors.

A key lesson from previous clinical trials with rAAV is that preclinical studies need to be evaluated in a context relevant to humans. They have, therefore, focused on non-human primates for evaluation of rAAV vectors because, like humans, macaques are natural hosts for AAV infection. This provides an important opportunity to evaluate gene transfer efficiency with rAAV vectors in out-bred animals previously sensitised to wild type AAV, which is not possible with murine or canine models. Finally, regulatory authorities in Europe and the United States are now requesting preclinical safety and efficacy studies in nonhuman primates as a condition for authorisation of a clinical trial.

To overcome the disadvantages mentioned above, the inventors have created an improved isolated nucleotide sequence encoding Factor VIII, along with a new promoter.

SUMMARY OF THE INVENTION

In a first aspect, the present invention provides an isolated nucleic acid molecule comprising a nucleotide sequence having at least 75% homology to the nucleotide sequence of SEQ ID NO: 1 and which encodes functional factor VIII (fVIII or FVIII).

The present invention also provides a vector comprising a nucleic acid molecule which comprises a nucleotide sequence having at least 75% homology to the nucleotide sequence of SEQ ID NO: 1 and which encodes functional factor VIII.

Further, the present invention provides a host cell comprising a nucleic acid molecule as described above or a vector as described above.

Additionally, the present invention provides a protein or glycoprotein expressed by a host cell as described above.

Furthermore, the present invention provides a transgenic animal comprising cells which comprise a nucleic acid molecule or a vector as described above.

The present invention also provides a method of treating haemophilia comprising administering a vector as described above or a protein as described above to a patient suffering from haemophilia.

Further, the present invention provides a nucleic acid molecule as described above, a protein as described above or a vector as described above for use in therapy.

Additionally, the present invention provides a nucleic acid molecule as described above, a protein as described above or a vector as described above for use in the treatment of haemophilia.

Also, the present invention provides a method for delivery of a nucleotide sequence encoding a function factor VIII to a subject, which method comprises administering to the said subject a nucleic acid molecule as described above, a protein as described above or a vector as described above.

Furthermore, the present invention provides a promoter comprising a nucleotide sequence having at least 85% homology to the nucleotide sequence of SEQ ID NO: 3.

The present invention also provides a second vector comprising a promoter which comprises a nucleotide sequence having at least 85% homology to the nucleotide sequence of SEQ ID NO: 3.

Further, the present invention provides a second host cell comprising the promoter as described above or the second vector as described above.

Additionally, the present invention provides an expression product expressed by the second host cell as described above, wherein an expressible nucleotide sequence is operably linked to the promoter.

Furthermore, the present invention provides a second transgenic animal comprising cells which comprise the promoter as described above or the second vector as described above.

The present invention also provides a method for the preparation of a parvoviral gene delivery vector, the method comprising the steps of:
  (a) providing an insect cell comprising one or more nucleic acid constructs comprising:
    (i) a nucleic acid molecule of any one of claims 1 to 6 that is flanked by at least one parvoviral inverted terminal repeat nucleotide sequence;
    (ii) a first expression cassette comprising a nucleotide sequence encoding one or more parvoviral Rep proteins which is operably linked to a promoter that is capable of driving expression of the Rep protein(s) in the insect cell;
    (iii) a second expression cassette comprising a nucleotide sequence encoding one or more parvoviral capsid proteins which is operably linked to a promoter that is capable of driving expression of the capsid protein(s) in the insect cell;
  (b) culturing the insect cell defined in (a) under conditions conducive to the expression of the Rep and the capsid proteins; and, optionally,
  (c) recovering the parvoviral gene delivery vector.

DETAILED DESCRIPTION OF THE INVENTION

According to a first aspect of the invention, there is provided an isolated nucleic acid molecule comprising a nucleotide sequence having substantial homology to the nucleotide sequence of SEQ ID NO: 1. The term substantial homology can be further defined with reference to a percentage homology. This is discussed in further detail below.

The term "isolated" when used in relation to a nucleic acid molecule of the invention typically refers to a nucleic acid sequence that is identified and separated from at least one contaminant nucleic acid with which it is ordinarily associated in its natural source. Isolated nucleic acid may be present in a form or setting that is different from that in which it is found in nature. In contrast, non-isolated nucleic acids are nucleic acids such as DNA and RNA found in the state they exist in nature. For example, a given DNA sequence (e.g. a gene) is found on the host cell chromosome in proximity to neighbouring genes; RNA sequences, such as a specific mRNA sequence encoding a specific protein, are found in the cell as a mixture with numerous other mRNAs which encode a multitude of proteins. The isolated nucleic acid molecule of the invention may be present in single-stranded or double-stranded form. When an isolated nucleic acid molecule is to be utilized to express a protein, it will typically contain at a minimum the sense or coding strand (i.e., nucleic acid molecule may be single-stranded), but may contain both the sense and anti-sense strands (i.e., the nucleic acid molecule may be double-stranded).

The nucleic acid molecule of the invention preferably has at least 75%, more preferably at least 80%, more preferably still at least 85%, even more preferably at least 90%, and more preferably at least 95% homology, for example at least 98% homology to the nucleotide sequence of SEQ ID NO: 1. It also preferably has at least 70%, more preferably at least 75%, and more preferably at least 80% homology to wild-type factor VIII. Further, the nucleic acid molecule preferably encodes for a functional factor VIII protein, that is to say it encodes for factor VIII which, when expressed, has the functionality of wild type factor VIII. The nucleic acid molecule, when expressed in a suitable system (e.g. a host cell), produces a functional factor VIII protein and at a relatively high level. Since the factor VIII that is produced is functional, it will have a conformation which is the same as at least a portion of the wild type factor VIII. In one embodiment, the factor VIII produced by the nucleic acid will have the same conformation as the N6 factor VIII which has been previously described. A functional factor VIII protein produced by the invention allows at least some blood coagulation to take place in a subject. This causes a decrease in the time it takes for blood to clot in a subject suffering from haemophilia. Normal factor VIII participates in blood coagulation via the coagulation cascade. Normal factor VIII is a cofactor for factor IXa which, in the presence of $Ca^2$ and phospholipids forms a complex that converts factor X to the activated form Xa. Therefore, a functional factor VIII protein according to the invention can form a functional complex with factor IXa which can convert factor X to the activated form Xa.

Previously used factor VIII nucleotide sequences have had problems with expression of functional protein. This is thought to be due to inefficient expression of mRNA, protein misfolding with subsequent intracellular degradation, and inefficient transport of the primary translation product from the endoplasmic reticulum to the Golgi apparatus. The inventors have found that the nucleic acid molecule provided by the invention causes surprisingly high levels of expression of a factor VIII protein both in vitro and in vivo. This means that this nucleic acid molecule could be used in gene therapy to treat haemophilia such as haemophilia A.

The nucleotide sequence of SEQ ID NO: 1 is a codon optimised human factor VIII nucleic acid sequence which is based on the sequence of the N6 factor VIII nucleotide sequence. The N6 factor VIII nucleotide sequence is a Factor VIII sequence from which the B domain has been deleted and replaced with a short B-domain spacer, rich in asparagine-linked oligosaccharides, which improves transport of the N6-FVIII from the ER to the Golgi.

The inventors have shown that SEQ ID NO:1 and sequences which are similar to it, i.e. those sequences which have a relatively high level of homology, all show surprisingly high levels of expression of functional protein. In this regard, SEQ ID NOs: 4, 5, 6 and 7 are also codon optimised factor VIII nucleic acid sequences, the % homology of which are 88%, 77%, 82% and 97% respectively, compared to SEQ ID NO: 1.

A nucleotide sequence of the invention may have at least about 400, at least about 650, at least about 890, at least about 1140, at least about 1380, at least about 1530 of all codons coding for the functional Factor VIII being identical to the codons (in corresponding positions) in SEQ ID NO: 1.

The invention also provides a nucleic acid molecule which has at least 75%, preferably at least 80%, more preferably at least 85%, even more preferably at least 90%, and more preferably at least 95% homology, for example 98% homology to the nucleotide sequence of SEQ ID NO: 4.

A nucleotide sequence of the invention may have at least about 410, at least about 670, at least about 920, at least about 1180, at least about 1430, at least about 1580 of all codons coding for the functional Factor VIII being identical to the codons (in corresponding positions) in SEQ ID NO: 4.

The nucleotide sequence of SEQ ID NO: 4 is a codon optimised factor VIII nucleic acid sequence which is based on the sequence of an SQ N6 factor VIII nucleotide sequence. The SQ N6 factor VIII nucleotide sequence is a Factor VIII sequence from which the B domain has been deleted and replaced with an SQ link of 14 amino acids between the a2 and a3 domains. Within the SQ link, an N6 B-domain has been inserted.

Further, the invention provides a nucleic acid molecule which has at least 75%, preferably at least 80%, more preferably at least 85%, even more preferably at least 90%, and more preferably at least 95% homology, for example 98% homology to the nucleotide sequence of SEQ ID NO: 5.

A nucleotide sequence of the invention may have at least about 360, at least about 580, at least about 800, at least about 1020, at least about 1380, at least about 1230 of all codons coding for the functional Factor VIII being identical to the condos (in corresponding positions) in SEQ ID NO: 5.

The nucleotide sequence of SEQ ID NO: 5 is a condo optimised factor VIII nucleic acid sequence which is based on the sequence of an SQ factor VIII nucleotide sequence. The SQ factor VIII nucleotide sequence is a Factor VIII sequence from which the B domain has been deleted and replaced with an SQ link of 14 amino acids between the a2 and a3 domains. The presence of the SQ link in the complex promotes efficient intracellular cleavage of the primary single chain translation product of 170 kDa due to the basic arginine residues which form a recognition motif for proteolytic cleavage by the membrane bound subtilisin-like protease furin.

Additionally, the invention provides a nucleic acid molecule which has at least 75%, preferably at least 80%, more preferably at least 85%, even more preferably at least 90%, and more preferably at least 95% homology, for example 98% homology to the nucleotide sequence of SEQ ID NO: 6.

A nucleotide sequence of the invention may have at least about 410, at least about 660, at least about 910, at least about 1160, at least about 1410, at least about 1560 of all codons coding for the functional Factor VIII being identical to the codons (in corresponding positions) in SEQ ID NO: 6.

The nucleotide sequence of SEQ ID NO: 6 is a codon optimised factor VIII nucleic acid sequence which is based on the sequence of an SQ Fugu B factor VIII nucleotide sequence. The SQ Fugu B factor VIII nucleotide sequence is a Factor VIII sequence from which the B domain has been deleted and replaced with an SQ link of 14 amino acids between the a2 and a3 domains. Within the SQ link, a Fugu B-domain has been inserted. A Fugu B domain is the factor VIII B-domain from the teleost puffer fish *Fugu rubripes*. The Fugu B domain has a high concentration of N-linked glycosylation sites which greatly improve intracellular trafficking and expression of the sequence.

Furthermore, the invention provides a nucleic acid molecule which has at least 75%, preferably at least 80%, more preferably at least 85%, even more preferably at least 90%, and more preferably at least 95% homology, for example 98% homology to the nucleotide sequence of SEQ ID NO: 7.

A nucleotide sequence of the invention may have at least about 440, at least about 710, at least about 970, at least about 1240, at least about 1500, at least about 1670 of all codons coding for the functional Factor VIII being identical to the codons (in corresponding positions) in SEQ ID NO: 7.

The nucleotide sequence of SEQ ID NO: 7 is a codon optimised factor VIII nucleic acid sequence which is based on the sequence of the N6 factor VIII nucleotide sequence.

All the above embodiments relating to different sequences preferably encode for a functional factor VIII. Further preferred features are the same as those relating to SEQ ID NO: 1 where appropriate. This will be apparent to a person skilled in the art.

In one embodiment, any of the nucleic acid molecules of the invention may comprise a nucleotide sequence encoding for an SQ link in the factor VIII protein. The amino acid sequence of the SQ link is preferably the sequence of SEQ ID NO: 18.

In another embodiment, any of the nucleic acid molecules of the invention may comprise a nucleotide sequence encoding for an N6 B-domain in the factor VIII protein.

In a further embodiment, any of the nucleic acid molecules of the invention may comprise a nucleotide sequence encoding for a Fugu B-domain in the factor VIII protein.

The nucleic acid of the invention may comprise an SQ link and an N6 B-domain in the factor VIII protein, or an SQ link and a Fugu B-domain in the factor VIII protein.

Generally, codon optimisation does not change the amino acid for which each codon encodes. It simply changes the nucleotide sequence so that it is more likely to be expressed at a relatively high level compared to the non-codon optimised sequence. Therefore, in one embodiment, the nucleic acid molecule of the invention encodes for a protein having between 0 and 350, between 0 and 300, between 0 and 250, between 0 and 200, between 0 and 150, between 0 and 100, between 0 and 50, between 0 and 30, between 0 and 20, between 0 and 15, between 0 and 10, or between 0 and 5 amino acid changes to the protein encoded by the nucleotide sequence of SEQ ID NO: 1, SEQ ID NO: 4, SEQ ID NO: 5, SEQ ID NO: 6 or SEQ ID NO: 7. This means that the nucleotide sequence of the nucleic acid of the invention and, for example, SEQ ID NO: 1 (or SEQ ID NO: 4, etc.) may be different but when they are translated the amino acid sequence of the protein that is produced only differs by between 0 and 10 amino acids. Preferably, any amino acid changes encoded for by the nucleic acid of the invention compared to SEQ ID NO: 1, SEQ ID NO: 4, SEQ ID NO: 5, SEQ ID NO: 6 or SEQ ID NO: 7 are in the portion of the sequence which replaced the B-domain of the factor VIII protein, i.e. the changes do not occur in the other domains of the protein such as the A1, a1, A2, a2, a3, A3, C1 or C2 domains. Amino acid changes in the other domains of the factor VIII protein affect the biological activity of the factor VIII protein.

Further, the nucleic acid molecule of the invention may encode for a protein which is encoded by the nucleotide sequence of SEQ ID NO: 1, SEQ ID NO: 4, SEQ ID NO: 5, SEQ ID NO: 6 or SEQ ID NO: 7. This means that the nucleotide sequences of the nucleic acid of the invention and, for example, SEQ ID NO: 1 (or SEQ ID NO: 4, etc.) may be different but when they are translated the amino acid sequence of the protein that is produced is the same.

In a preferred embodiment of the invention, the nucleotide sequence coding for a functional Factor VIII has an improved codon usage bias for the human cell as compared to naturally occurring nucleotide sequence coding for the corresponding non-codon optimized sequence. The adaptiveness of a nucleotide sequence encoding a functional Factor VIII to the codon usage of human cells may be expressed as codon adaptation index (CAI). A codon adaptation index is herein defined as a measurement of the relative adaptiveness of the codon usage of a gene towards the codon usage of highly expressed human genes. The relative adaptiveness (w) of each codon is the ratio of the usage of each codon, to that of the most abundant codon for the same amino acid. The CAI is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Kim et al., Gene. 1997, 199:293-301; zur Megede et al., Journal of Virology, 2000, 74: 2628-2635). Preferably, a nucleic acid molecule encoding a Factor VIII has a CAI of at least 0.8, 0.85, 0.90, 0.92, 0.94, 0.95, 0.96 or 0.97.

In a particular embodiment, the nucleic acid molecule encodes for a protein comprising the sequence of SEQ ID NO: 2 or SEQ ID NO: 21 having between 0 and 250, between 0 and 200, between 0 and 150, between 0 and 100, between 0 and 50, between 0 and 30, between 0 and 20, between 0 and 15, between 0 and 10, or between 0 and 5 amino acid changes thereto. If the nucleic acid molecule encodes for a protein comprising the sequence of SEQ ID NO: 2 or SEQ ID NO: 21 having changes to any of the amino acids, the protein should still be a functional protein. A skilled person will appreciate that minor changes can be made to some of the amino acids of the protein without affecting the function of the protein. Preferably, the amino acid changes are in the portion of the sequence which replaced the B-domain of the factor VIII protein, i.e. the changes do not occur in the other domains of the protein such as the A1, a1, A2, a2, a3, A3, C1 or C2 domains. In other embodiments, the nucleic acid molecule may encode for a protein comprising or consisting of the sequence of SEQ ID NO: 2 or SEQ ID NO: 21.

It would be well with the capabilities of a skilled person to produce a nucleic acid molecule according to the invention. This could be done, for example, using chemical synthesis of a given sequence.

Further, a skilled person would readily be able to determine whether a nucleic acid according to the invention expresses a functional protein. Suitable methods would be apparent to those skilled in the art. For example, one suitable in vitro method involves inserting the nucleic acid into a vector, such as a lentiviral or an AAV vector, transducing host cells, such as 293T or HeLa cells, with the vector, and assaying for factor VIII activity. Alternatively, a suitable in vivo method involves transducing a vector containing the nucleic acid into haemophiliac mice and assaying for functional factor VIII in the plasma of the mice. Suitable methods are described in more detail below.

The nucleic acid can be any type of nucleic acid composed of nucleotides. The nucleic acid should be able to be expressed so that a protein is produced. Preferably, the nucleic acid is DNA or RNA.

The nucleic acid molecule preferably comprises a nucleotide sequence selected from the sequence of SEQ ID NO: 1, SEQ ID NO: 4, SEQ ID NO: 5, SEQ ID NO: 6 and SEQ ID NO: 7. In one embodiment, the nucleic acid molecule comprises a nucleotide sequence selected from the sequence of SEQ ID NO: 1 and SEQ ID NO: 7. The nucleic acid molecule may consist of a nucleotide sequence selected from the sequence of SEQ ID NO: 1, SEQ ID NO: 4, SEQ TD NO: 5, SEQ ID NO: 6 and SEQ ID NO: 7. Further, The nucleic acid molecule may consist of a nucleotide sequence selected from the sequence of SEQ ID NO: 1 and SEQ ID NO: 7. In one embodiment, the nucleic acid molecule consists of a nucleotide sequence of SEQ ID NO: 1.

Also provided is a vector comprising the nucleic acid molecule of the invention. The vector may be any appropriate vector, including viral and non-viral vectors. Viral vectors include lenti-, adeno-, herpes viral vectors. It is preferably a recombinant adeno-associated viral (rAAV) vector or a lentiviral vector. Alternatively, non-viral systems may be used, including using naked DNA (with or without chromatin attachment regions) or conjugated DNA that is introduced into cells by various transfection methods such as lipids or electroporation.

The vector preferably also comprises any other components required for expression of the nucleic acid molecule, such as promoters. Any appropriate promoters may be used, such as LP1, HCR-hAAT, ApoE-hAAT, and LSP. These promoters are described in more detail in the following references: LP1: Nathwani A. et al. Blood. 2006 Apr. 1; 107(7): 2653-2661; HCR-hAAT: Miao C H et al. Mol Ther. 2000; 1: 522-532; ApoE-hAAT: Okuyama T et al. Human Gene Therapy, 7, 637-645 (1996); and LSP: Wang L et al. Proc Natl Acad Sci USA. 1999 Mar. 30; 96(7): 3906-3910.

A particular preferred promoter is provided by the invention. Accordingly, there is provided a promoter comprising a nucleotide sequence having substantial homology to the nucleotide sequence of SEQ ID NO: 3. The promoter is liver specific. In one embodiment, the nucleic acid molecule described above further comprises a nucleotide sequence having substantial homology to the nucleotide sequence of SEQ ID NO: 3. The term substantial homology can be further defined with reference to a percentage homology. This is discussed in further detail below.

A vector according to the invention may be a gene delivery vector. Such a gene delivery vector may be a viral gene delivery vector or a non-viral gene delivery vector.

Non-viral gene delivery may be carried out using naked DNA which is the simplest method of non-viral transfection. It may be possible, for example, to administer a nucleic acid of the invention using naked plasmid DNA. Alternatively, methods such as electroporation, sonoporation or the use of a "gene gun", which shoots DNA coated gold particles into the cell using, for example, high pressure gas or an inverted 0.22 calibre gun, may be used.

To improve the delivery of a nucleic acid into a cell, it may be necessary to protect it from damage and its entry into the cell may be facilitated. To this end, lipoplexes and polyplexes may be used that have the ability to protect a nucleic acid from undesirable degradation during the transfection process.

Plasmid DNA may be coated with lipids in an organized structure such as a micelle or a liposome. When the organized structure is complexed with DNA it is called a lipoplex. Anionic and neutral lipids may be used for the construction of lipoplexes for synthetic vectors. Preferably, however, cationic lipids, due to their positive charge, may be used to condense negatively charged DNA molecules so as to facilitate the encapsulation of DNA into liposomes. If may be necessary to add helper lipids (usually electroneutral lipids, such as DOPE) to cationic lipids so as to form lipoplexes.

Complexes of polymers with DNA, called polyplexes, may be used to deliver a nucleic acid of the invention. Most polyplexes consist of cationic polymers and their production is regulated by ionic interactions. Polyplexes typically cannot release their DNA load into the cytoplasm. Thus, co-transfection with endosome-lytic agents (to lyse the endosome that is made during endocytosis, the process by which the polyplex enters the cell), such as inactivated adenovirus, may be necessary.

Hybrid methods may be used to deliver a nucleic acid of the invention that combines two or more techniques. Virosomes are one example; they combine liposomes with an inactivated HIV or influenza virus. Other methods involve mixing other viral vectors with cationic lipids or hybridizing viruses and may be used to deliver a nucleic acid of the invention.

A dendrimer may be used to deliver a nucleic acid of the invention, in particular, a cationic dendrimer, i.e. one with a positive surface charge. When in the presence of genetic material such as DNA or RNA, charge complimentarity leads to a temporary association of the nucleic acid with the cationic dendrimer. On reaching its destination the dendrimer-nucleic acid complex is then imported into the cell via endocytosis.

More typically, a suitable viral gene delivery vector may be used to deliver a nucleic acid of the invention. Viral vectors suitable for use in the invention may be a parvovirus, an adenovirus, a retrovirus, a lentivirus or a herpes simplex virus. The parvovirus may be an adenovirus-associated virus (AAV).

As used herein, in the context of gene delivery, the term "vector" or "gene delivery vector" may refer to a particle that functions as a gene delivery vehicle, and which comprises nucleic acid (i.e., the vector genome) packaged within, for example, an envelope or capsid. Alternatively, in some contexts, the term "vector" may be used to refer only to the vector genome.

Accordingly, the present invention provides gene delivery vectors (comprising a nucleic acid of the invention) based on animal parvoviruses, in particular dependoviruses such as infectious human or simian AAV, and the components thereof (e.g., an animal parvovirus genome) for use as vectors for introduction and/or expression of a Factor VIII polypeptide in a mammalian cell. The term "parvoviral" as used herein thus encompasses dependoviruses such as any type of AAV.

Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus Dependovirus. As may be deduced from the name of their genus, members of the Dependovirus are unique in that they usually require coinfection with a helper virus such as adenovirus or herpes virus for productive infection in cell culture. The genus Dependovirus includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996). For convenience the present invention is further exemplified and described herein by reference to AAV. It is, however, understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wild type (wt) AAV infection in mammalian cells the Rep genes (i.e. encoding Rep78 and Rep52 proteins) are expressed from the P5 promoter and the P19 promoter, respectively and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

In an AAV suitable for use as a gene therapy vector, the vector genome typically comprises a nucleic acid of the invention (as described herein) to be packaged for delivery to a target cell. According to this particular embodiment, the heterologous nucleotide sequence is located between the viral ITRs at either end of the vector genome. In further preferred embodiments, the parvovirus (e. g. AAV) cap genes and parvovirus (e.g. AAV) rep genes are deleted from the template genome (and thus from the virion DNA produced therefrom). This configuration maximizes the size of the nucleic acid sequence(s) that can be carried by the parvovirus capsid.

According to this particular embodiment, the nucleic acid of the invention is located between the viral ITRs at either end of the substrate. It is possible for a parvoviral genome to function with only one ITR. Thus, in a gene therapy vector of the invention based on a parvovirus, the vector genome is flanked by at least one ITR, but, more typically, by two AAV ITRs (generally with one either side of the vector genome, i.e. one at the 5' end and one at the 3' end). There may be intervening sequences between the nucleic acid of the invention in the vector genome and one or more of the ITRs.

Preferably, the nucleic acid encoding a functional Factor VIII polypeptide (for expression in the mammalian cell) will be incorporated into a parvoviral genome located between two regular ITRs or located on either side of an ITR engineered with two D regions.

AAV sequences that may be used in the present invention for the production of AAV gene therapy vectors can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g. GenBank Accession number U89790; GenBank Accession number J01901; GenBank Accession number AF043303; GenBank Accession number AF085716; Chiorini et al. (1997, J. Vir. 71: 6823-33); Srivastava et al. (1983, J. Vir. 45:555-64); Chiorini et al. (1999, J. Vir. 73:1309-1319); Rutledge et al. (1998, J. Vir. 72:309-319); and Wu et al. (2000, J. Vir. 74: 8635-47). AAV serotype 1, 2, 3, 4, 5, 6, 7, 8 or 9 may be used in the present invention. However, AAV serotypes 1, 5 or 8 are preferred sources of AAV sequences for use in the context of the present invention.

Preferably the AAV ITR sequences for use in the context of the present invention are derived from AAV1, AAV2, AAV4 and/or AAV6. Likewise, the Rep (Rep78 and Rep52) coding sequences are preferably derived from AAV1, AAV2, AAV4 and/or AAV6. The sequences coding for the VP1, VP2, and VP3 capsid proteins for use in the context of the present invention may however be taken from any of the known 42 serotypes, more preferably from AAV1, AAV2, AAV3, AAV4, AAV5, AAV6, AAV7, AAV8 or AAV9 or newly developed AAV-like particles obtained by e.g. capsid shuffling techniques and AAV capsid libraries.

AAV Rep and ITR sequences are particularly conserved among most serotypes. The Rep78 proteins of various AAV serotypes are e.g. more than 89% identical and the total nucleotide sequence identity at the genome level between AAV2, AAV3A, AAV3B, and AAV6 is around 82% (Bantel-Schaal et al., 1999, J. Virol., 73(2):939-947). Moreover, the Rep sequences and ITRs of many AAV serotypes are known to efficiently cross-complement (i.e., functionally substitute) corresponding sequences from other serotypes in production of AAV particles in mammalian cells. US2003148506 reports that AAV Rep and ITR sequences also efficiently cross-complement other AAV Rep and ITR sequences in insect cells.

The AAV VP proteins are known to determine the cellular tropicity of the AAV virion. The VP protein-encoding sequences are significantly less conserved than Rep proteins and genes among different AAV serotypes. The ability of Rep and ITR sequences to cross-complement corresponding sequences of other serotypes allows for the production of pseudotyped AAV particles comprising the capsid proteins of a serotype (e.g., AAV1, 5 or 8) and the Rep and/or ITR sequences of another AAV serotype (e.g., AAV2). Such pseudotyped rAAV particles are a part of the present invention.

Modified "AAV" sequences also can be used in the context of the present invention, e.g. for the production of AAV gene therapy vectors. Such modified sequences e.g. include sequences having at least about 70%, at least about 75%, at least about 80%, at least about 85%, at least about 90%, at least about 95%, or more nucleotide and/or amino acid sequence identity (e.g., a sequence having about 75-99% nucleotide sequence identity) to an AAV1, AAV2, AAV3, AAV4, AAV5, AAV6, AAV7, AAV8 or AAV9 ITR, Rep, or VP can be used in place of wild-type AAV ITR, Rep, or VP sequences.

Although similar to other AAV serotypes in many respects, AAV5 differs from other human and simian AAV serotypes more than other known human and simian serotypes. In view thereof, the production of rAAV5 can differ from production of other serotypes in insect cells. Where methods of the invention are employed to produce rAAV5, it is preferred that one or more constructs comprising, collectively in the case of more than one construct, a nucleotide sequence comprising an AAV5 ITR, a nucleotide sequence comprises an AAV5 Rep coding sequence (i.e. a nucleotide sequence comprises an AAV5 Rep78). Such ITR and Rep sequences can be modified as desired to obtain efficient production of AAV5 or pseudotyped AAV5 vectors. For example, the start codon of the Rep sequences can be modified, VP splice sites can be modified or eliminated, and/or the VP1 start codon and nearby nucleotides can be modified to improve the production of AAV5 vectors.

Thus, the viral capsid used in the invention may be from any parvovirus, either an autonomous parvovirus or dependovirus, as described above. Preferably, the viral capsid is an AAV capsid (e. g., AAV1, AAV2, AAV3, AAV4, AAV5 or AAV6 capsid). In general, the AAV1 capsid or AAV6 capsid are preferred. The choice of parvovirus capsid may be based on a number of considerations as known in the art, e.g., the target cell type, the desired level of expression, the nature of the heterologous nucleotide sequence to be expressed, issues related to viral production, and the like. For example, the AAV1 and AAV6 capsid may be advantageously employed for skeletal muscle; AAV1, AAV5 and AAV8 for the liver and cells of the central nervous system (e.g., brain); AAV5 for cells in the airway and lung or brain; AAV3 for bone marrow cells; and AAV4 for particular cells in the brain (c. g., appendable cells).

It is within the technical skills of the skilled person to select the most appropriate virus, virus subtype or virus serotype. Some subtypes or serotypes may be more appropriate than others for a certain type of tissue.

For example, liver-specific expression of a nucleic acid of the invention may advantageously be induced by AAV-mediated transduction of liver cells. Liver is amenable to AAV-mediated transduction, and different scrotypes may be used (for example, AAV1, AAV5 or AAV8). Transduction of muscle may be accomplished by administration of an AAV encoding a nucleic acid of the invention via the blood stream. Thus, intravenous or intra-arterial administration is applicable.

A parvovirus gene therapy vector prepared according to the invention may be a "hybrid" particle in which the viral TRs and viral capsid are from different parvoviruses. Preferably, the viral TRs and capsid are from different serotypes of AAV. Likewise, the parvovirus may have a "chimeric" capsid (e. g., containing sequences from different parvoviruses, preferably different AAV serotypes) or a "targeted" capsid (e. g., a directed tropism).

In the context of the invention "at least one parvoviral ITR nucleotide sequence" is understood to mean a palindromic sequence, comprising mostly complementary, symmetrically arranged sequences also referred to as "A," "B," and "C" regions. The ITR functions as an origin of replication, a site having a "cis" role in replication, i.e., being a recognition site for trans-acting replication proteins such as e.g. Rep 78 (or Rep68) which recognize the palindrome and specific sequences internal to the palindrome. One exception to the symmetry of the ITR sequence is the "D" region of the ITR. It is unique (not having a complement within one ITR). Nicking of single-stranded DNA occurs at the junction between the A and D regions. It is the region where new DNA synthesis initiates. The D region normally sits to one side of the palindrome and provides directionality to the nucleic acid replication step. A parvovirus replicating in a mammalian cell typically has two ITR sequences. It is, however, possible to engineer an ITR so that binding sites are on both strands of the A regions and D regions are located symmetrically, one on each side of the palindrome. On a double-stranded circular DNA template (e.g., a plasmid), the Rep78- or Rep68-assisted nucleic acid replication then proceeds in both directions and a single ITR suffices for parvoviral replication of a circular vector. Thus, one ITR nucleotide sequence can be used in the context of the present invention. Preferably, however, two or another even number of regular ITRs are used. Most preferably, two ITR sequences are used. A preferred parvoviral ITR is an AAV ITR. For safety reasons it may be desirable to construct a parvoviral (AAV) vector that is unable to further propagate after initial introduction into a cell. Such a safety mechanism for limiting undesirable vector propagation in a recipient may be provided by using AAV with a chimeric ITR as described in US2003148506.

Those skilled in the art will appreciate that the viral Rep protein(s) used for producing an AAV vector of the invention may be selected with consideration for the source of the viral ITRs. For example, the AAV5 ITR typically interacts more efficiently with the AAV5 Rep protein, although it is not necessary that the serotype of ITR and Rep protein(s) are matched.

The ITR(s) used in the invention are typically functional, i.e. they may be fully resolvable and are preferably AAV sequences, with serotypes 1, 2, 3, 4, 5 or 6 being preferred. Resolvable AAV ITRs according to the present invention need not have a wild-type ITR sequence (e. g., a wild-type sequence may be altered by insertion, deletion, truncation or missense mutations), as long as the ITR mediates the desired functions, e. g., virus packaging, integration, and/or provirus rescue, and the like.

Advantageously, by using a gene therapy vector as compared with previous approaches, the restoration of protein synthesis, i.e. factor VIII synthesis, is a characteristic that the transduced cells acquire permanently or for a sustained period of time, thus avoiding the need for continuous administration to achieve a therapeutic effect.

Accordingly, the vectors of the invention therefore represent a tool for the development of strategies for the in vivo delivery of a nucleic acid of the invention, by engineering the nucleic acid within a gene therapy vector that efficiently transduces an appropriate cell type, such as a liver cell.

In a further aspect of the invention, a host is provided comprising the vector described above. Preferably, the vector is capable of expressing the nucleic acid molecule of the invention in the host. The host may be any suitable host.

As used herein, the term "host" refers to organisms and/or cells which harbour a nucleic acid molecule or a vector of the invention, as well as organisms and/or cells that are suitable for use in expressing a recombinant gene or protein.

It is not intended that the present invention be limited to any particular type of cell or organism. Indeed, it is contemplated that any suitable organism and/or cell will find use in the present invention as a host. A host cell may be in the form of a single cell, a population of similar or different cells, for example in the form of a culture (such as a liquid culture or a culture on a solid substrate), an organism or part thereof.

A host cell according to the invention may permit the expression of a nucleic acid molecule of the invention. Thus, the host cell may be, for example, a bacterial, a yeast, an insect or a mammalian cell.

Any insect cell which allows for replication of a recombinant parvoviral (rAAV) vector and which can be maintained in culture can be used in accordance with the present invention. For example, the cell line used can be from Spodoptera frugiperda, drosophila cell lines, or mosquito cell lines, e.g., Aedes albopictus derived cell lines. Preferred insect cells or cell lines are cells from the insect species which are susceptible to baculovirus infection, including e.g. Se301, SeIZD2109, SeUCR1, Sf9, Sf900+, Sf21, BTI-TN-5B1-4, MG-1, Tn368, HzAm1, Ha2302, Hz2E5, High Five (Invitrogen, CA, USA) and expresSF+® (U.S. Pat. No. 6,103,526; Protein Sciences Corp., CT, USA).

In addition, the invention provides a method for the preparation of a parvoviral gene delivery vector, the method comprising the steps of:
 (a) providing an insect cell comprising one or more nucleic acid constructs comprising:
  (i) a nucleic acid molecule of the invention that is flanked by at least one parvoviral inverted terminal repeat nucleotide sequence;
  (ii) a first expression cassette comprising a nucleotide sequence encoding one or more parvoviral Rep proteins which is operably linked to a promoter that is capable of driving expression of the Rep protein(s) in the insect cell;
  (iii) a second expression cassette comprising a nucleotide sequence encoding one or more parvoviral capsid proteins which is operably linked to a promoter that is capable of driving expression of the capsid protein(s) in the insect cell;
 (b) culturing the insect cell defined in (a) under conditions conducive to the expression of the Rep and the capsid proteins; and, optionally,
 (c) recovering the parvoviral gene delivery vector.

In general, therefore, the method of the invention allows the production of a parvoviral gene delivery vector (comprising a nucleic acid of the invention) in an insect cell. Preferably, the method comprises the steps of: (a) culturing an insect cell as defined above under conditions such that the parvoviral (e.g. AAV) vector is produced; and, (b) recovering the recombinant parvoviral (e.g. AAV) vector. Preferably, the parvoviral gene delivery vector is an AAV gene delivery vector.

It is understood here that the (AAV) vector produced in such a method preferably is an infectious parvoviral or AAV virion that comprises a parvoviral genome, which itself comprises a nucleic acid of the invention. Growing conditions for insect cells in culture, and production of heterologous products in insect cells in culture are well-known in the art and described e.g. in the above cited references on molecular engineering of insects cells.

In a method of the invention, a nucleic acid of the invention that is flanked by at least one parvoviral ITR sequence is provided. This type of sequence is described in detail above. Preferably, the nucleic acid of the invention is sequence is located between two parvoviral ITR sequences.

The first expression cassette comprises a nucleotide sequence encoding one or more parvoviral Rep proteins which is operably linked to a first promoter that is capable of driving expression of the Rep protein(s) in the insect cell.

A nucleotide sequence encoding animal parvoviruses Rep proteins, is herein understood as a nucleotide sequence encoding the non-structural Rep proteins that are required and sufficient for parvoviral vector production in insect cells such the Rep78 and Rep52 proteins, or the Rep68 and Rep40 proteins, or the combination of two or more thereof.

The animal parvovirus nucleotide sequence preferably is from a dependovirus, more preferably from a human or simian adeno-associated virus (AAV) and most preferably from an AAV which normally infects humans (e.g., serotypes 1, 2, 3A, 3B, 4, 5, and 6) or primates (e.g., serotypes 1 and 4). Rep coding sequences are well known to those skilled in the art and suitable sequences are referred to and described in detail in WO2007/148971 and also in WO2009/014445.

Preferably, the nucleotide sequence encodes animal parvoviruses Rep proteins that are required and sufficient for parvoviral vector production in insect cells.

The second expression cassette comprises a nucleotide sequence encoding one or more parvoviral capsid proteins which is operably linked to a promoter that is capable of driving expression of the capsid protein(s) in the insect cell. The capsid protein(s) expressed may be one or more of those described above.

Preferably, the nucleotide sequence encodes animal parvoviruses cap proteins that are required and sufficient for parvoviral vector production in insect cells.

These three sequences (genome, rep encoding and cap encoding) are provided in an insect cell by way of one or more nucleic acid constructs, for example one, two or three nucleic acid constructs. Preferably then, the one or nucleic acid constructs for the vector genome and expression of the parvoviral Rep and cap proteins in insect cells is an insect cell-compatible vector. An "insect cell-compatible vector" or "vector" is understood to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the presence of the vector in the insect cell need not be permanent and transient episomal vectors are also included. The vectors can be introduced by any means known, for example by chemical treatment of the cells, electroporation, or infection. In a preferred embodiment, the vector is a baculovirus, a viral vector, or a plasmid. In a more preferred embodiment, the vector is a baculovirus, i.e. the construct is a baculoviral vector. Baculoviral vectors and methods for their use are well known to those skilled in the art.

Typically then, a method of the invention for producing a parvoviral gene delivery vector comprises: providing to a cell permissive for parvovirus replication (a) a nucleotide sequence encoding a template for producing vector genome of the invention (as described in detail herein); (b) nucleotide sequences sufficient for replication of the template to produce a vector genome (the first expression cassette defined above); (c) nucleotide sequences sufficient to package the vector genome into a parvovirus capsid (the second expression cassette defined above), under conditions sufficient for replication and packaging of the vector genome into the parvovirus capsid, whereby parvovirus particles comprising the vector genome encapsidated within the parvovirus capsid are produced in the cell. Preferably, the parvovirus replication and/or capsid coding sequences are AAV sequences.

A method of the invention may preferably comprise the step of affinity-purification of the (virions comprising the) recombinant parvoviral (rAAV) vector using an anti-AAV antibody, preferably an immobilised antibody. The anti-AAV antibody preferably is a monoclonal antibody. A particularly suitable antibody is a single chain camelid antibody or a fragment thereof as e.g. obtainable from camels or llamas (see e.g. Muyldermans, 2001, Biotechnol. 74: 277-302). The antibody for affinity-purification of rAAV preferably is an antibody that specifically binds an epitope on a AAV capsid protein, whereby preferably the epitope is an epitope that is present on capsid protein of more than one AAV serotype. E.g. the antibody may be raised or selected on the basis of specific binding to AAV2 capsid but at the same time also it may also specifically bind to AAV1, AAV3, AAV5, AAV6, AAV8 or AAV9 capsids.

The invention also provides a means for delivering a nucleic acid of the invention into a broad range of cells, including dividing and non-dividing cells. The present invention may be employed to deliver a nucleic acid of the invention to a cell in vitro, e. g. to produce a polypeptide encoded by such a nucleic acid molecule in vitro or for ex vivo gene therapy.

The nucleic acid molecule, vector, cells and methods/use of the present invention are additionally useful in a method of delivering a nucleic acid of the invention to a host in need thereof, typically a host suffering from haemophilia A.

The present invention finds use in both veterinary and medical applications. Suitable subjects for gene delivery methods as described herein include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects are most preferred. Human subjects include neonates, infants, juveniles, and adults.

The invention thus provides a pharmaceutical composition comprising a nucleic acid or a vector of the invention and a pharmaceutically acceptable carrier or diluent and/or other medicinal agent, pharmaceutical agent or adjuvant, etc.

For injection, the carrier will typically be a liquid. For other methods of administration, the carrier may be either solid or liquid. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

In general, a "pharmaceutically acceptable carrier" is one that is not toxic or unduly detrimental to cells. Exemplary pharmaceutically acceptable carriers include sterile, pyrogen-free water and sterile, pyrogen-free, phosphate buffered saline. Pharmaceutically acceptable carriers include physiologically acceptable carriers. The term "pharmaceutically acceptable carrier" includes any and all solvents, dispersion media, coatings, antibacterial and antifungal agents, isotonic and absorption delaying agents, and the like that are physiologically compatible".

By "pharmaceutically acceptable" it is meant a material that is not biologically or otherwise undesirable, i.e., the material may be administered to a subject without causing any undesirable biological effects. Thus, such a pharmaceutical composition may be used, for example, in transfection of a cell ex vivo or in administering a viral particle or cell directly to a subject.

A carrier may be suitable for parenteral administration, which includes intravenous, intraperitoneal or intramuscular administration, Alternatively, the carrier may be suitable for sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated.

Pharmaceutical compositions are typically sterile and stable under the conditions of manufacture and storage. Pharmaceutical compositions may be formulated as a solution, microemulsion, liposome, or other ordered structure suitable to accommodate high drug concentration. The carrier may be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. A nucleic acid or vector of the invention may be administered in a time or controlled release formulation, for example in a composition which includes a slow release polymer or other carriers that will protect the compound against rapid release, including implants and microencapsulated delivery systems. Biodegradable, biocompatible polymers may for example be used, such as ethylene vinyl acetate, polyanhydrides, polyglycolic acid, collagen, polyorthoesters, polylactic acid and polylactic, polyglycolic copolymers (PLG).

The parvoviral, for example AAV, vector of the invention may be of use in transferring genetic material to a cell. Such transfer may take place in vitro, ex vivo or in vivo.

Accordingly, the invention provides a method for delivering a nucleotide sequence to a cell, which method comprises contacting a nucleic acid, a vector, or a pharmaceutical composition as described herein under conditions such the nucleic acid or vector of the invention enters the cell. The cell may be a cell in vitro, ex vivo or in vivo.

The invention also provides a method of treating haemophilia comprising administering an effective amount of a nucleic acid, a protein or a vector according to the invention to a patient suffering from haemophilia. Preferably the patient is suffering from haemophilia A. Preferably, the patient is human.

Further, the invention also provides a method for delivering or administering a nucleotide sequence to a subject, which method comprises administering to the said subject a nucleic acid, a vector, or a pharmaceutical composition as described herein. In particular, the present invention provides a method of administering a nucleic acid molecule of the invention to a subject, comprising administering to the subject a parvoviral gene therapy vector according to the invention, optionally together with a pharmaceutically acceptable carrier. Preferably, the parvoviral gene therapy vector is administered in a therapeutically-effective amount to a subject in need thereof. That is to say, administration according to the invention is typically carried out under conditions that result in the expression of functional Factor VIII at a level that provides a therapeutic effect in a subject in need thereof.

Delivery of a nucleic acid or vector of the invention to a host cell in vivo may result in an increase of functional factor VIII in the host, for example to a level that ameliorates one or more symptoms of a blood clotting disorder such as haemophilia A.

The level of naturally occurring factor VIII in a subject suffering from haemophilia A varies depending on the severity of the haemophilia. Patients with a severe form of the disease have factor VIII levels of less than about 1% of the level found in a normal healthy subject (referred to herein as "a normal level". A normal level is about 50-150 IU/dL). Patients with a moderate form of the disease have factor VIII levels of between about 1% and about 5% of a normal level. Patients with a mild form of the disease have factor VIII levels of more than about 5% of a normal level; typically between about 5% and about 30% of a normal level.

It has been found that when the method of treatment of the invention is used, it can cause an increase in the level of functional factor VIII of at least about 1% of normal levels, i.e. in addition to the factor VIII level present in the subject before treatment. In a subject suffering from haemophilia, such an increase can cause amelioration of a symptom of haemophilia. In particular, an increase of at least 1% can reduce the frequency of bleeding that occurs in sufferers of haemophilia, especially those with a severe form of the disease. In one embodiment, the method of treatment causes an increase in the level of functional factor VIII of at least about 5% of normal levels. This could change the phenotype of the disease from severe to mild. Patients with a mild form of the disease rarely have spontaneous bleeding. In other embodiments, the method of treatment of the invention causes an increase in the level of functional factor VIII of at least about 2%, at least about 3%, at least about 4%, at least about 10%, at least about 15%, at least about 20% or at least about 25% of normal levels. In a particular embodiment, the method of treatment of the invention causes an increase in the level of functional factor VIII of at least about 30% of normal levels. This level of increase would virtually normalise coagulation of blood in subjects suffering haemophilia. Such subjects are unlikely to require factor VIII concentrates following trauma or during surgery.

In another embodiment, the method of treatment of the invention may cause an increase in the level of functional factor VIII to at least about 1% of normal levels. The method of treatment may cause an increase in the level of functional factor VIII to at least about 5% of normal levels. In other embodiments, the method of treatment of the invention may cause an increase in the level of functional factor VIII to at least about 2%, at least about 3%, at least about 4%, at least about 10%, at least about 15%, at least about 20% or at least about 25% of normal levels. In a particular embodiment, the method of treatment of the invention causes an increase in the level of functional factor VIII to at least about 30% of normal levels. A subject whose functional factor VIII level has been increase to 30% or more will have virtually normal coagulation of blood.

In one embodiment, the method of treatment of the invention causes an increase in the level of functional factor VIII to, at most, normal levels.

The level of functional factor VIII can be measured relatively easily and methods for measuring factor VIII levels are well known to those skilled in the art. Many clotting assays are available, including chromogenic and clotting based assays. ELISA tests are also widely available. A particular method is to measure the level of factor VIII:C which is a lab measure of the clotting activity of factor VIII. A normal level of factor VIII:C is 46.8 to 141.8 IU/dL or 0.468-1.4 IU/ml.

A further method is to measure the activated partial thromboplastin time (aPTT) which is a measure of the ability of blood to clot. A normal aPTT is between about 24 and about 34 seconds. A subject suffering from haemophilia will have a longer aPTT. This method can be used in combination with prothrombin time measurement.

Also provided is a nucleic acid molecule, protein or vector of the invention for use in therapy, especially in the treatment of haemophilia, particularly haemophilia A.

The use of a nucleic acid molecule, protein or vector of the invention in the manufacture of a medicament for the treatment of haemophilia, particularly haemophilia A, is also provided.

The invention also provides a nucleic acid or a vector of the invention for use in the treatment of the human or animal body by therapy. In particular, a nucleic acid or a vector of the invention is provided for use in the treatment of a blood clotting disorder such as haemophilia, for example haemophilia A. A nucleic acid or a vector of the invention is provided for use in ameliorating one or more symptoms of a blood clotting disorder, for example by reducing the frequency and/or severity of bleeding episodes.

The invention further provides a method of treatment of a blood clotting disorder, which method comprises the step of administering an effective amount of a nucleic acid or a vector of the invention to a subject in need thereof.

Accordingly, the invention further provides use of a nucleic acid or vector as described herein in the manufacture of a medicament for use in the administration of a nucleic acid to a subject. Further, the invention provides a nucleic acid or vector as described herein in the manufacture of a medicament for use in the treatment of a blood clotting disorder.

Typically, a nucleic acid or a vector of the invention may be administered to a subject by gene therapy, in particular by use of a parvoviral gene therapy vector such as AAV. General methods for gene therapy are known in the art. The vector, composition or pharmaceutical composition may be delivered to a cell in vitro or ex vivo or to a subject in vivo by any suitable method known in the art. Alternatively, the vector may be delivered to a cell ex vivo, and the cell administered to a subject, as known in the art. In general, the present invention can be employed to deliver any nucleic acid of the invention to a cell in vitro, ex vivo, or in vivo.

The present invention further provides a method of delivering a nucleic acid to a cell. Typically, for in vitro methods, the virus may be introduced into the cell by standard viral transduction methods, as are known in the art.

Preferably, the virus particles are added to the cells at the appropriate multiplicity of infection according to standard transduction methods appropriate for the particular target cells. Titres of virus to administer can vary, depending upon the target cell type and the particular virus vector, and may be determined by those of skill in the art without undue experimentation.

Cells may be removed from a subject, the parvovirus vector is introduced therein, and the cells are then replaced back into the subject. Methods of removing cells from subject for treatment ex vivo, followed by introduction back into the subject are known in the art. Alternatively, an AAV vector may be introduced into cells from another subject, into cultured cells, or into cells from any other suitable source, and the cells are administered to a subject in need thereof.

A further aspect of the invention is a method of treating subjects in vivo with a nucleic acid or vector of the invention. Administration of a nucleic acid or vector of the present invention to a human subject or an animal in need thereof can be by any means known in the art for administering virus vectors.

A nucleic acid or vector of the invention will typically be included in a pharmaceutical composition as set out above. Such compositions include the nucleic acid or vector in an effective amount, sufficient to provide a desired therapeutic or prophylactic effect, and a pharmaceutically acceptable carrier or excipient. An "effective amount" includes a therapeutically effective amount or a prophylactically effective amount.

A "therapeutically effective amount" refers to an amount effective, at dosages and for periods of time necessary, to achieve the desired therapeutic result, such as raising the level of functional Factor VIII in a subject (so as to lead to functional Factor VIII production to level sufficient to ameliorate the symptoms of the disease associated with a lack of that protein).

A therapeutically effective amount of a nucleic acid molecule or vector of the invention may vary according to factors such as the disease state, age, sex, and weight of the individual, and the ability of the nucleic acid molecule or vector to elicit a desired response in the individual. Dosage regimens may be adjusted to provide the optimum therapeutic response. A therapeutically effective amount is also typically one in which any toxic or detrimental effects of the nucleic acid molecule or vector are outweighed by the therapeutically beneficial effects.

Viral gene therapy vectors may be administered to a cell or host in a biologically-effective amount. A "biologically-effective" amount of the virus vector is an amount that is sufficient to result in infection (or transduction) and expression of the heterologous nucleic acid sequence in the cell. If the virus is administered to a cell in vivo (e. g., the virus is administered to a subject), a "biologically-effective" amount of the virus vector is an amount that is sufficient to result in transduction and expression of a nucleic acid according to the invention in a target cell.

For a nucleic acid molecule or vector of the invention, such as a gene therapy vector, the dosage to be administered may depend to a large extent on the condition and size of the subject being treated as well as the therapeutic formulation, frequency of treatment and the route of administration. Regimens for continuing therapy, including dose, formulation, and frequency may be guided by the initial response and clinical judgment. The parenteral route of injection into the interstitial space of tissue may be preferred, although other parenteral routes, such as inhalation of an aerosol formulation, may be required in specific administration. In some protocols, a formulation comprising the gene and gene delivery system in an aqueous carrier is injected into tissue in appropriate amounts.

Exemplary modes of administration include oral, rectal, transmucosal, topical, transdermal, inhalation, parenteral (e. g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation.

The tissue/cell type to be administered a nucleic acid molecule or vector of the invention may be of any type, but will typically be a hepatic/liver cell. It is not intended that the present invention be limited to any particular route of administration. However, in order that liver cells are transduced, a nucleic acid molecule or vector of the present invention may successfully be administered via the portal or arterial vasculature. Alternatively, the cell may be any progenitor cell. As a further alternative, the cell can be a stem cell (e. g., a liver stem cell). The tissue target may be specific or it may be a combination of several tissues, for example the liver and muscle tissues.

In the case of a gene therapy vector, the effective dose range for small animals such as mice, following intramuscular injection, may be between about $1\times10^{11}$ and about $1\times10^{12}$ genome copy (gc)/kg, and for larger animals (cats) and possibly human subjects, between about $1\times10^{10}$ and about $1\times10^{13}$ gc/kg. Dosages of the parvovirus gene therapy vector of the invention will depend upon the mode of administration, the disease or condition to be treated, the individual subject's condition, the particular virus vector, and the gene to be delivered, and can be determined in a routine manner. Typically, an amount of about $10^3$ to about $10^{16}$ virus particles per dose may be suitable. Preferably, an amount of about $10^9$ to about $10^{14}$ virus particles per dose is used. When treated in this way, a subject may receive a single dose of virus particles so that the viral particles effect treatment in a single administration.

The amount of active compound in the compositions of the invention may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation.

It may be advantageous to formulate parenteral compositions in dosage unit form for ease of administration and uniformity of dosage. "Dosage unit form" as used herein refers to physically discrete units suited as unitary dosages for subjects to be treated; each unit containing a predetermined quantity of active compound calculated to produce the desired therapeutic effect in association with the required pharmaceutical carrier. The specification for the dosage unit forms of the invention may be dictated by the unique characteristics of the active compound and the particular therapeutic effect to be achieved, and by the limitations inherent in the art of compounding such an active compound for the treatment of a condition in individuals.

Many methods for the preparation of such formulations are patented or generally known to those skilled in the art.

Also provided is a protein or glycoprotein expressed by a host cell of the invention.

Further provided is a transgenic animal comprising cells comprising a vector according to the invention. Preferably the animal is a non-human mammal, especially a primate such as a macaque. Alternatively, the animal may be a rodent, especially a mouse; or may be canine, feline, ovine or porcine.

In the aspect of the invention in which a promoter is provided comprising a nucleotide sequence having substantial homology to the nucleotide sequence of SEQ ID NO: 3, the promoter preferably has at least 85%, more preferably at least 90%, even more preferably at least 95% homology to the nucleotide sequence of SEQ ID NO: 3. The promoter is preferably less than 400 bp, more preferably less than 350 bp, even more preferably less than 300 bp in size.

The invention further provides a second vector comprising the promoter of the invention. The vector may be any appropriate vector, including viral and non-viral vectors. Viral vectors include lenti-, adeno-, herpes viral vectors. It is preferably a recombinant adeno-associated viral (rAAV) vector. Alternatively, non-viral systems may be used to introduce the promoter in to a cell, including using naked DNA (with or without chromatin attachment regions) or conjugated DNA that is introduced into cells by various transfection methods such as lipids or electroporation.

The second vector may comprise any expressible nucleotide sequence to produce an expression product, but preferably also comprises a nucleotide sequence encoding a protein or other molecule that should preferably be expressed in the liver, especially a blood clotting factor. The expressible nucleotide sequence may encode any gene that can be expressed from the liver, including those that are not specific for liver disorders. For instance, the liver may be used as a factory for synthesis of interferon that is then released and systemically distributed for the treatment of tumours at sites outside the liver. In addition to genes, the vector can also regulate the expression of sh or siRNA. The vector also preferably comprises any other components required for expression of the expressible sequence.

Also provided is a second isolated nucleic acid molecule. The isolated nucleic acid molecule comprises a first nucleotide sequence having substantial homology to the nucleotide sequence of SEQ ID NO: 1; and a second nucleotide sequence having substantial homology to the nucleotide sequence of SEQ ID NO: 3. The term substantial homology can be further defined with reference to a percentage homology. This is discussed in further detail herein.

In the second nucleic acid molecule (also referred to above in the first aspect of the invention), the two sequences may be contiguous or may be separated by a number of nucleotides. For example, the two sequences may be separated by a kozak sequence or one or more introns. The sequences are preferably operably linked, that is to say the second sequence, which encodes a promoter, is linked to the first sequence such that the first sequence may be expressed when introduced into a cell using a vector.

Also provided is a vector comprising the second nucleic acid molecule of the invention.

Further provided is a host cell comprising a vector according to the invention. The host cell may be any appropriate cell but is preferably a non-human mammalian cell, especially a primate cell. Cells may be used to produce the protein recombinantly, and any appropriate cell, such as a CHO cell, may be used.

Also provided is a protein or glycoprotein expressed by a host cell of the invention.

Further provided is a transgenic animal comprising cells comprising a vector according to the invention. Preferably the animal is a non-human mammal, especially a primate such as a macaque. Alternatively, the animal may be a rodent, especially a mouse; or may be canine, feline, ovine or porcine.

In the description above, the term "homology" is used to refer to the similarity of two sequences. This can also be described using the term "identity". The terms "homology" and "identity" can be used interchangeably herein. For the purpose of this invention, it is defined here that in order to determine the percent identity of two nucleic acid sequences, the sequences are aligned for optimal comparison purposes (e.g., gaps can be introduced in the sequence of a first nucleic acid for optimal alignment with a second amino or nucleic acid sequence). The nucleotide residues at nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, about twenty, about fifty, about one hundred, about two hundred, about five hundred, about 1000, about 2000, about 3000, about 4000, about 4500, about 5000 or more contiguous nucleic acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at http://www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The nucleic acid sequences of the present invention can further be used as a "query sequence" to perform a search against public databases to, for example, identify other family members or related sequences. Such searches can be performed using the BLASTN and BLASTP programs (version 2.0) of Altschul, et al. (1990) J. MoI. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at http://www.ncbi.nlm.nih.gov/.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

A skilled person will appreciate that all aspects of the invention, whether they relate to, for example, the nucleic acid, the vector, the host cell or the use, are equally applicable to all other aspects of the invention. In particular, aspects of the method of treatment, for example, the administration of the nucleic acid or vector, may have been described in greater detail than in some of the other aspects of the invention, for example, relating to the use of the nucleic acid or vector for treating haemophilia. However, the skilled person will appreciate where more detailed information has been given for a particular aspect of the invention, this information is likely to be equally applicable to other aspects of the invention. For example, the skilled person will appreciate that the description relating to vectors and host cells for the first aspect of the invention is applicable to all vectors and host cells of the invention. Further, the skilled person will also appreciate that the description relating to the method of treatment is equally applicable to the use of the nucleic acid or vector in treating haemophilia.

The invention will now be described in detail, by way of example only, with reference to the drawings in which:

FIG. 1: Human FVIII expression in haemophilia A mice. Top panel: A schematic of rAAV vector encoding the BDD hFVIII under the control of the LP1 liver specific promoter. Bottom panel: Human FVIII activity in mouse plasma at 8 weeks after tail vein administration of $2 \times 10^9$ vg/mouse (N=4). Naïve animals were injected with excipient.

Figure 2A:
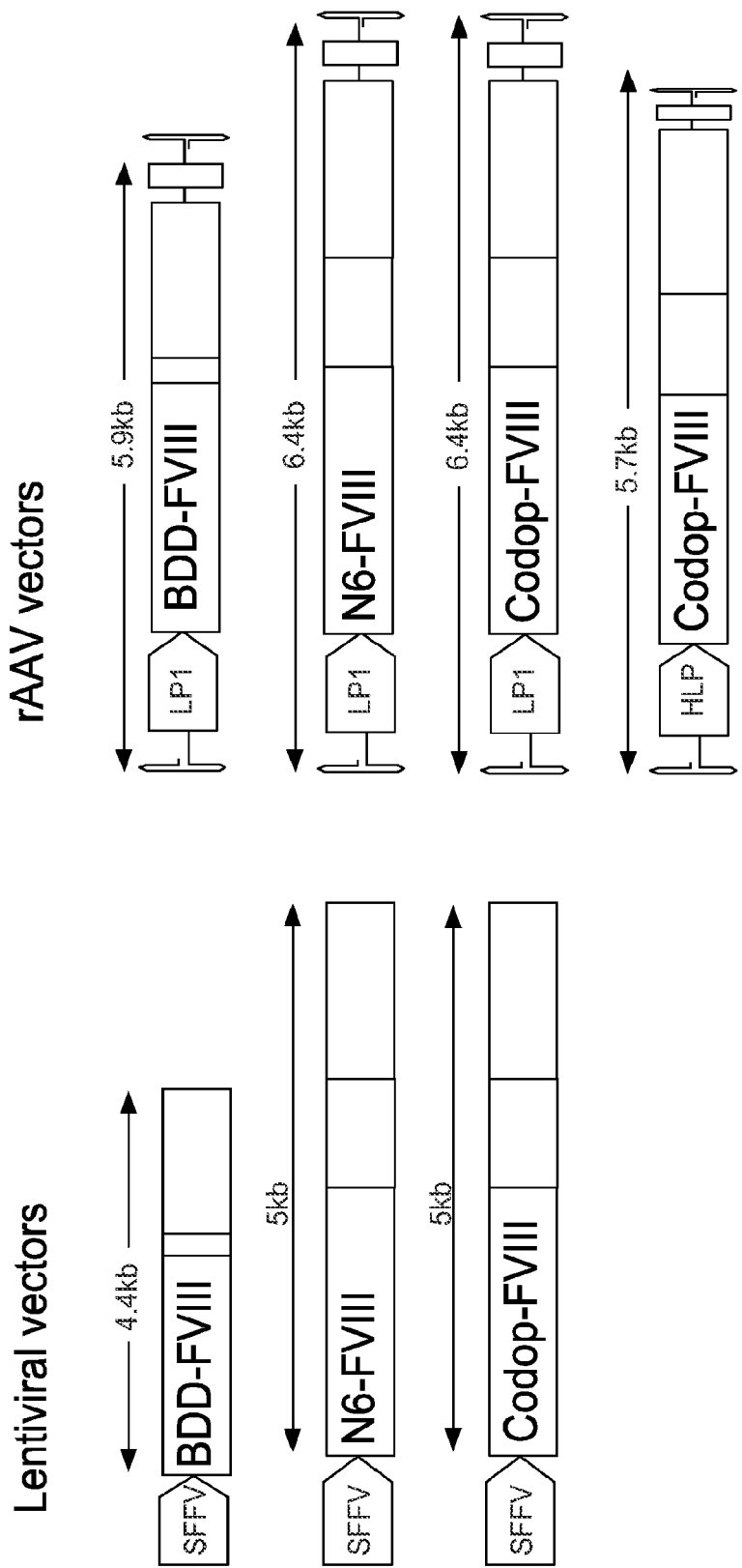
Figure 2B:
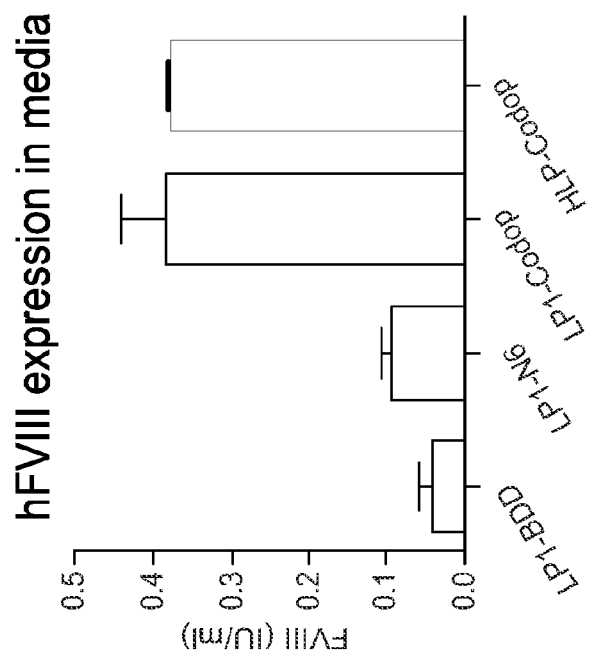
Figure 2B:
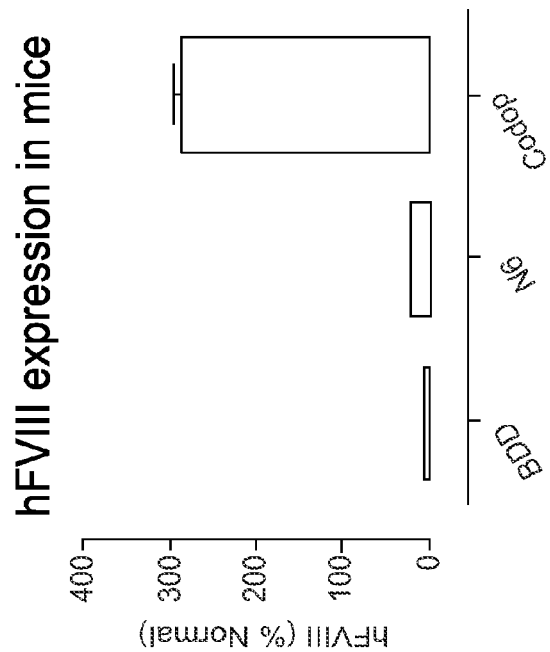

FIG. 2: A. Human FVIII activity in mouse plasma at 30 days following temporal vein administration of $1 \times 10^8$ TU of lentiviral vectors encoding either the BDD, N6 or the codop-FVIII under the control of the SFFV promoter (N=4). B. hFVIII activity in supernatant harvested from HepG2 cells transfected with rAAV plasmid encoding FVIII variants under the control of the LP1 promoter or the smaller rAAV HLP-codop-FVIII expression cassette (N=3).

Figure 3:
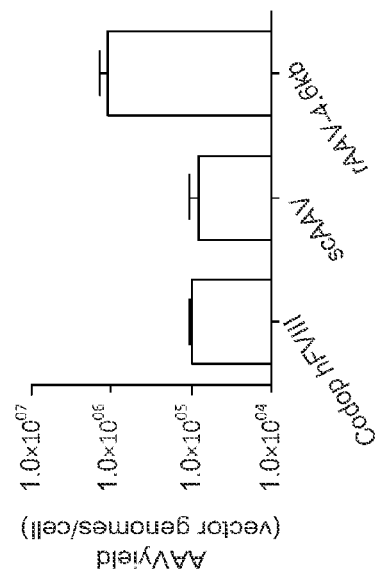
Figure 3:
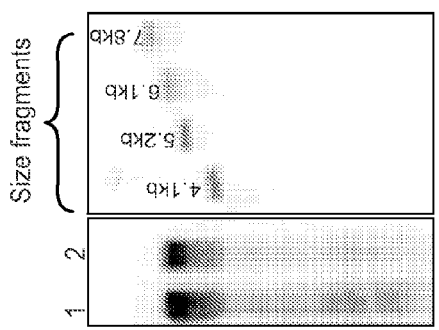
Figure 3:
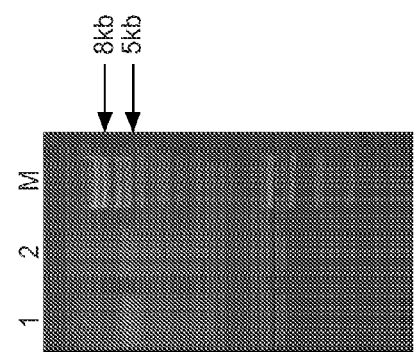

FIG. 3: A. Yield of rAAV-HLP-codop-hFVIII (n=5) pseudotyped with serotype 5 capsid when compared to the yield of scAAV-FIX containing a self complementary 2.3 kb cassette and single stranded rAAV vectors containing a 4.6 kb expression cassette. B. Native gel stained with ethidium bromide and C. Alkaline gel Southern analysis of the rAAV-HLP-codop-hFVIII viral genome derived from two separate preparations (1 and 2).

Figure 4:
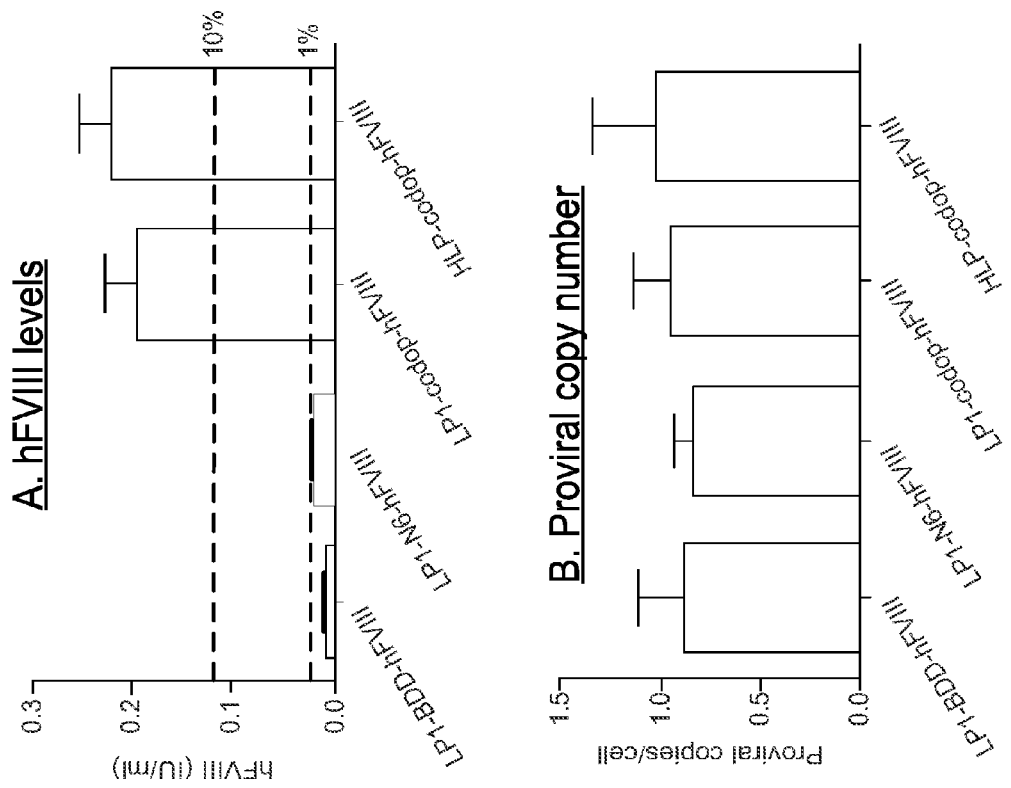

FIG. 4: A. Mean FVIII levels±SEM in murine plasma after a single tail vein administration of rAAV-hFVIII constructs pseudotyped with serotype 5 capsid (dose=$4 \times 10^{11}$ vg/mouse, N=3). B. Mean (±SEM) proviral copy number in murine liver transduced with rAAV5-hFVIII variants.

Figure 5:
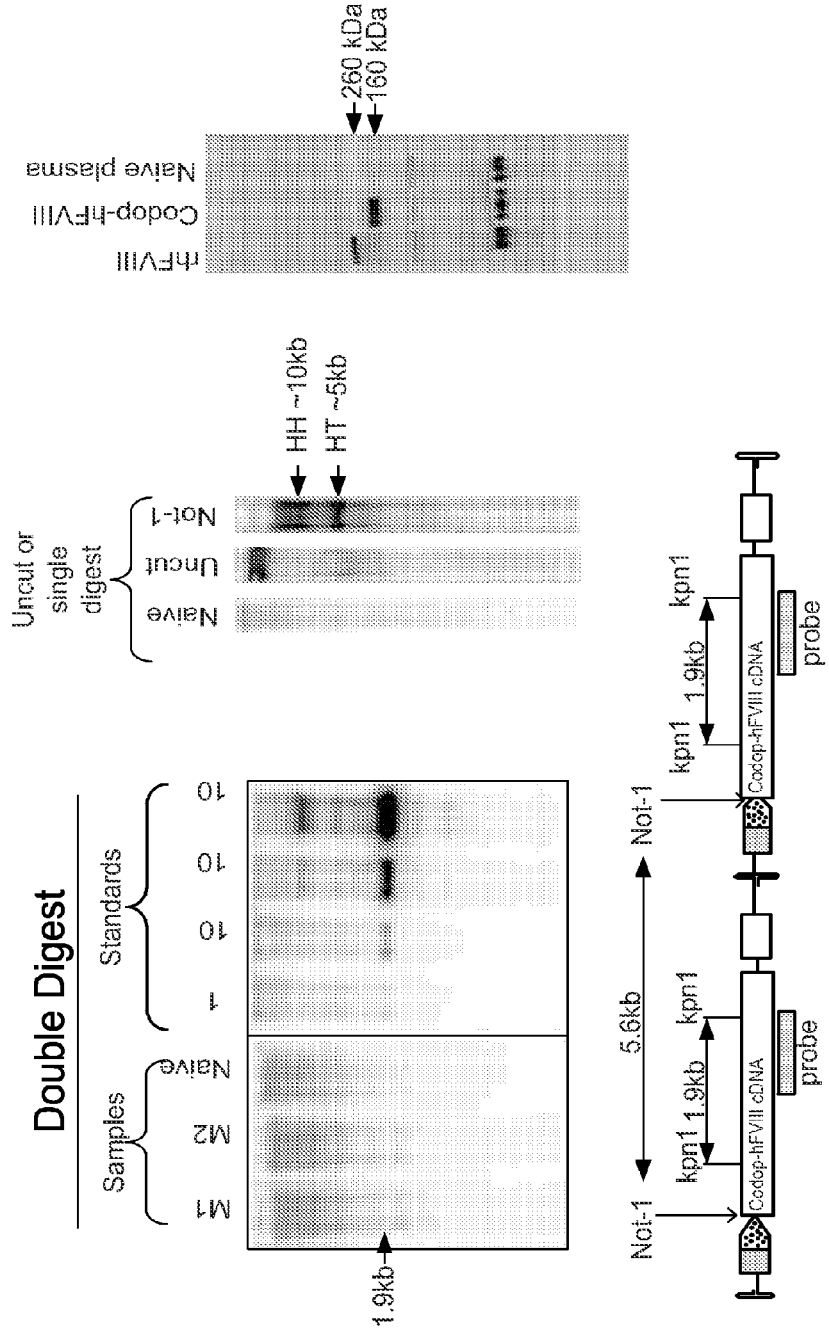

FIG. 5: A. Southern blot: Left panel showing double digest (Kpn-1) of liver genomic DNA derived from mice (M1 and M2) transduced with rAAV-HLP-codop-hFVIII. Right panel showing uncut DNA or that digested with a single cutter (Not-1). HH and HT=head to head and head to tail concantemers. B. Western blot showing a single ~210 kd band in the plasma of mice transduced with rAAV-HLP-codop-hFVIII, which is not present in naive mouse plasma or positive control consisting of full length recombinant human FVIII (rhFVIII) diluted in mouse plasma.

Figure 6:
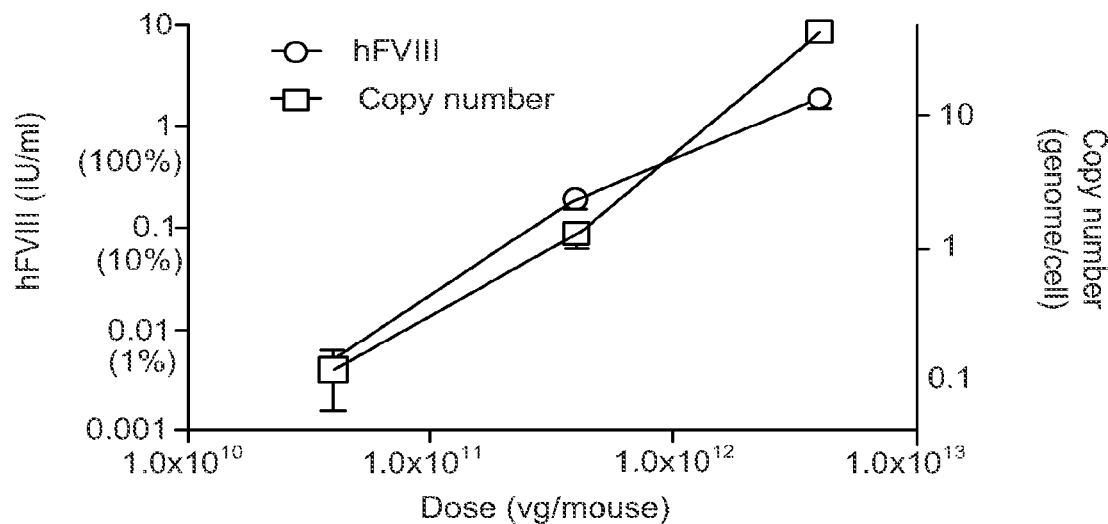
Figure 6:
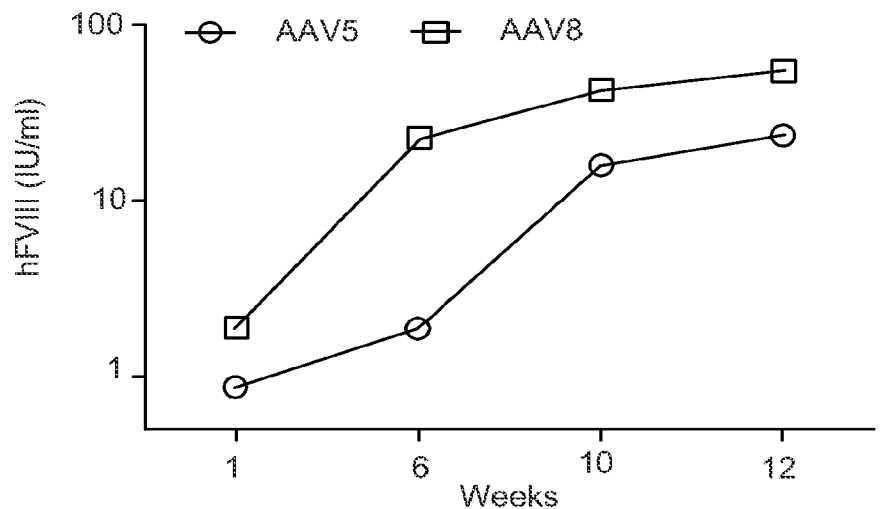

FIG. 6: A. Relationship between rAAV5-HLP-codop-hFVIII dose and hFVIII levels in murine plasma and transgene copy number at 6 weeks following gene transfer. B. Kinetics of hFVIII expression following a single tail vein administration of $4 \times 1012$ vg/mouse of rAAV-HLP-codop-hFVIII pseudotyped with serotype 5 or 8 capsid. Shown are mean levels+SEM.

Figure 7:
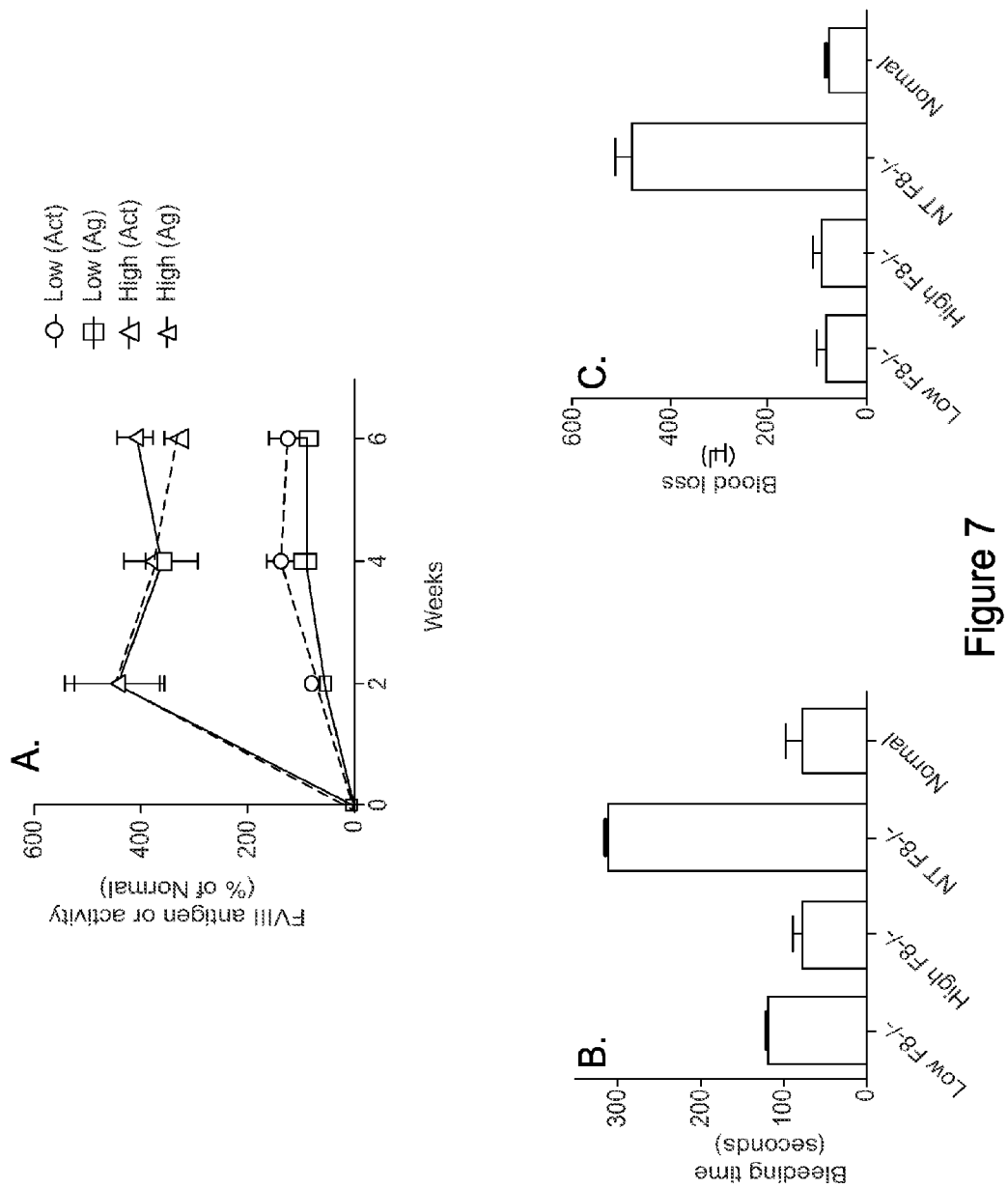

FIG. 7: A. FVIII activity and antigen level in F8−/− mice following a single tail vein administration of low and high dose of rAAV-HLP-codop-hFVIII. B and C. Bleeding time and blood loss in F8−/− mice following rAAV-HLP-codop-hFVIII gene transfer compared to untransduced F8−/− mice and normal wild type animals.

FIG. 8: (A) Schematic representation of human FVIII variants designed and cloned into a SIN lentiviral vector backbone. Nine different human FVIII variants were designed and cloned into a lentiviral vector backbone plasmid: BDD FVIII; B-domain deleted human FVIII (4.3 kb total size). FVIII Fugu B; BDD FVIII containing the Fugu B-domain (4.9 kb total size). FVIII N6; BDD FVIII containing the human N6 B-domain (5.0 kb total size). SQ FVIII; BDD FVIII containing a modified version of the SQ amino acid sequence $SQ^m$ (4.4 kb total size). SQ FVIII Fugu B; SQ FVIII containing the Fugu B-domain between the $SQ^m$ sequence to create the N terminal $SQ^a$ and C terminal $SQ^b$ sequences (5.0 kb total size). SQ FVIII N6; SQ FVIII containing the human N6 B-domain (5.1 kb total size). Constructs SQ FVIII (co) (4.4 kb total size), SQ FVIII Fugu B (co) (5.0 kb total size), and SQ FVIII N6 (co) (5.1 kb total size) are the same amino acid structure as constructs SQ FVIII, SQ FVIII Fugu B, and SQ FVIII N6, respectively, but are produced from a codon optimised cDNA sequence. Relative domain size is not accurate. Dashes on constructs mark asparagine (N)-linked glycosylation sites within the B-domain only. (B) Schematics of SQ and modified SQ sequences; $SQ^m$, $SQ^a$ and $SQ^b$. The SQ sequence is a 14 amino acid bridge between the a2 and a3 domains of FVIII created by fusing Ser743 and Gln1638 in the B-domain. The sequence promotes efficient intracellular cleavage by containing the 4 amino acid protease recognition site RHQR. A modified SQ sequence ($SQ^m$) was created containing a missense mutation from Lys 1644 to Thr1644 caused by the creation of an MluI restriction enzyme site within the cDNA sequence for insertion of the Fugu and N6 B-domains. $SQ^a$ is the 11aa sequence created at the N-terminal of the B-domain after insertion of the N6 or Fugu B-domain sequences into the SQ FV111 construct. $SQ^b$ is the 5 amino acid sequence created at the C-terminal of the B-domain after insertion of the N6 or Fugu B-domain sequences into the SQ FVIII construct, this sequence retains the 4 amino acid protease recognition site. MluI restriction sites are shown underlined and the K to T missense mutation is at the left hand amino acid position of the MluI restriction site.

Figure 9:
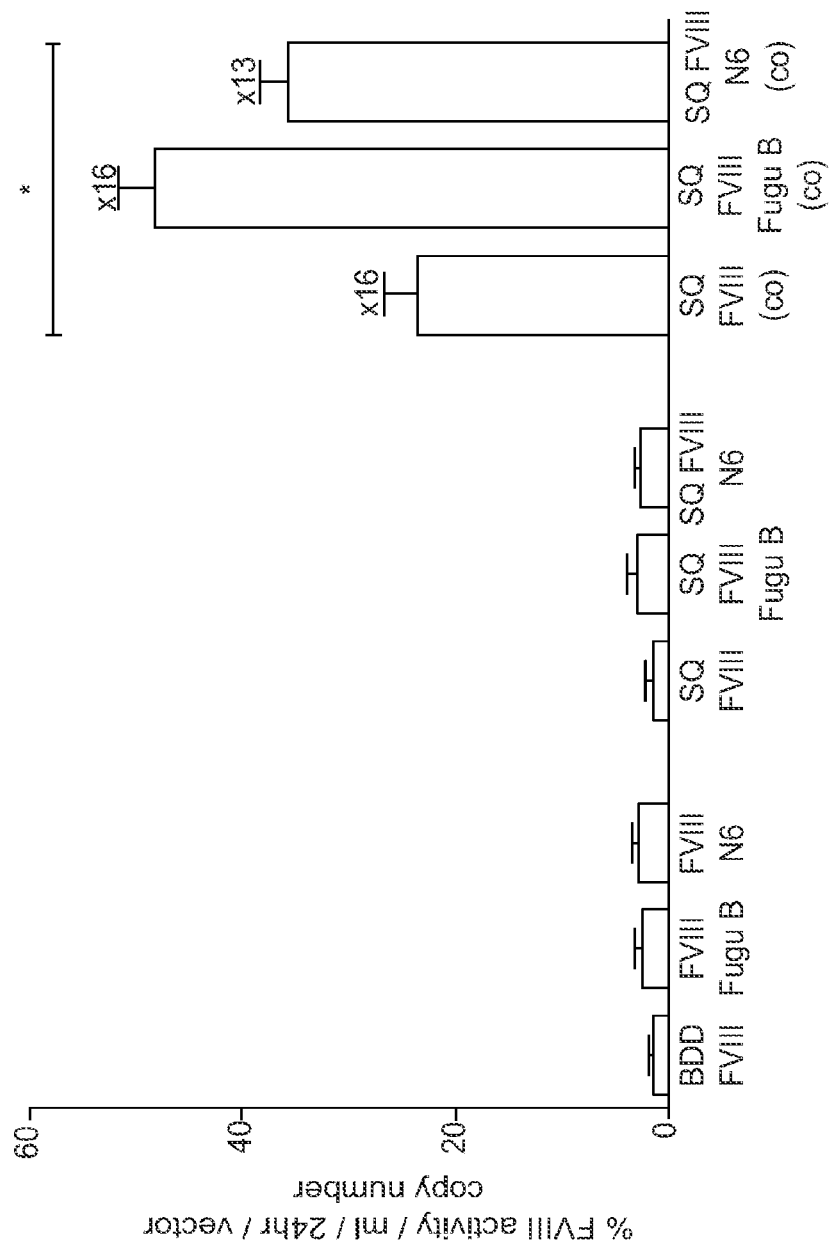

FIG. 9: Relative human FYIII activity of FVIII constructs in vitro as determined by chromogenic assay. $1 \times 10^5$ 293 T cells were transduced with serial dilutions of BDD FVIII, FVIII Fugu B, FVIII N6, SQ FVIII, SQ FVIII Fugu B, SQ FVIII N6, SQ FVIII (co), SQ FVIII Fugu B (co), or SQ FVIII N6 (co). At 48 hours cell media was changed for 5004, serum free media. After a further 24 hours incubation media was collected from all wells and assayed for factor VIII expression using a chromogenic based assay to measure factor VIII cofactor activity. Results were then normalised on copy number per cell determined by qPCR. Mean and SD shown for n=5. Values above bars represent the fold increase in FVIII expression from codon optimised constructs in comparison to equivalent non-codon optimised sequences. * Statistical analyses were performed using general linear model (GLM) based on two-way analysis of variance (ANOVA) with individual pairwise comparisons performed using Bonferroni simultaneous tests (Minitab software, Myerstown, Pa.). Results show a highly significant increase for SQ FVIII (co), SQ FVIII Fugu B (co), and SQ FVIII N6 (co) in comparison to their non codon optimised equivalents SQ FVIII, SQ FVIII Fugu B, SQ FVIII N6, respectively, (P<0.0001). In addition, results for codon optimised vectors also show a significant increase for SQ FVIII N6 (co) in comparison to SQ FVIII (co) (P<0.0001), and a significant increase for SQ FVIII Fugu B (co) in comparison to both SQ FVIII (co) and SQ FVIII N6 (co) (P<0.0001).

Figure 10:
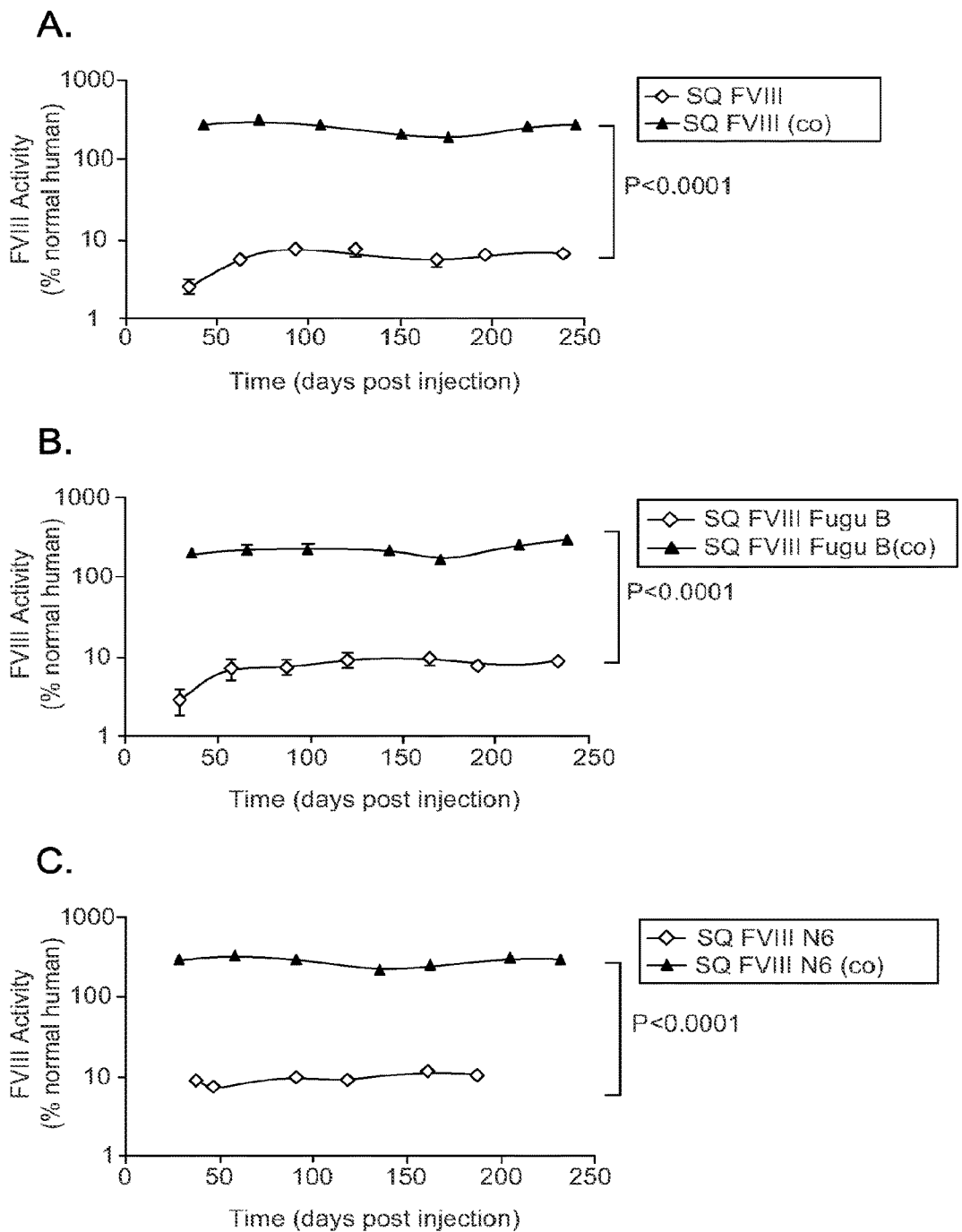

FIG. 10: Expression of human FYIII activity in vivo in blood plasma of hemophiliac mice after intravenous injection of SIN lentiviral vectors expressing bioengineered FVIII constructs. Six to ten F8$^{tm2Kaz}$ haemophilic neonatal mice were injected intravenously via the superficial temporal vein with SIN lentiviral vectors expressing bioengineered human FVIII constructs. Mice were bled at various timepoints over approximately 250 days and a chromogenic assay used to calculate the activity of human FVIII in blood plasma taken from each mouse as a percentage of normal human levels. (A) SQ FVIII (white diamonds) vs. SQ FVIII (co) (black triangles). (B) SQ FVIII Fugu B (white diamonds) vs. SQ FVIII Fugu B (co) (black triangles). (C) SQ FVIII N6 (white diamonds) vs. SQ FVIII N6 (co) (black triangles). Points on graphs represent the mean; error bars represent the standard deviation. Statistical analyses were performed using general linear model (GLM) based on two-way analysis of variance (ANOVA) with individual pairwise comparisons performed using Bonferroni simultaneous tests (Minitab software, Myerstown, Pa.).

Figure 11:
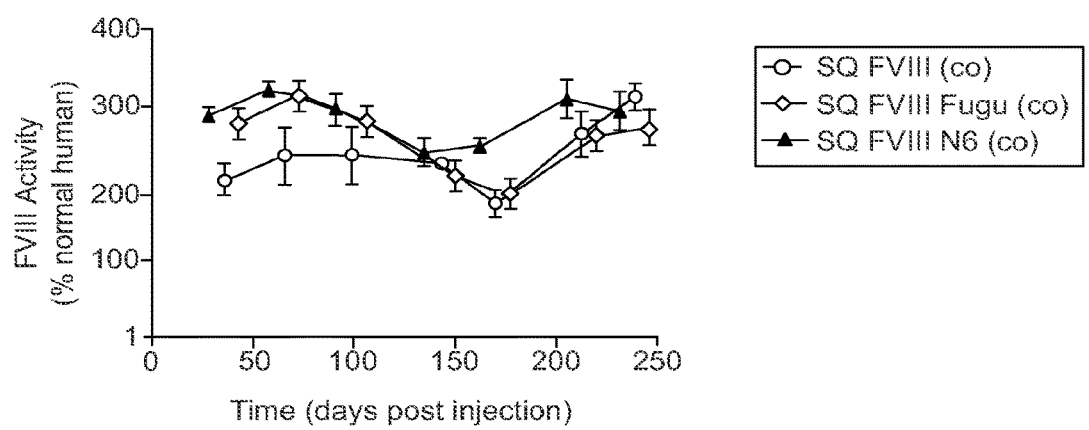

FIG. 11: FVIII activity levels in vivo in plasma taken from mice injected with vector expressing FVIII from codon optimised cDNA sequences. Activity of human FVIII in blood plasma taken from mice injected with lentiviral vector expressing SQ FVIII (co) (grey circles), SQ FVIII Fugu B (co) (white diamonds), and SQ FVIII N6 (co) (black triangles) collated. Points on graphs represent the mean, error bars represent the SD. No significant difference in expression is noted between constructs expressing different B-domains (P>0.5, Bonferroni simultaneous test).

Figure 12:
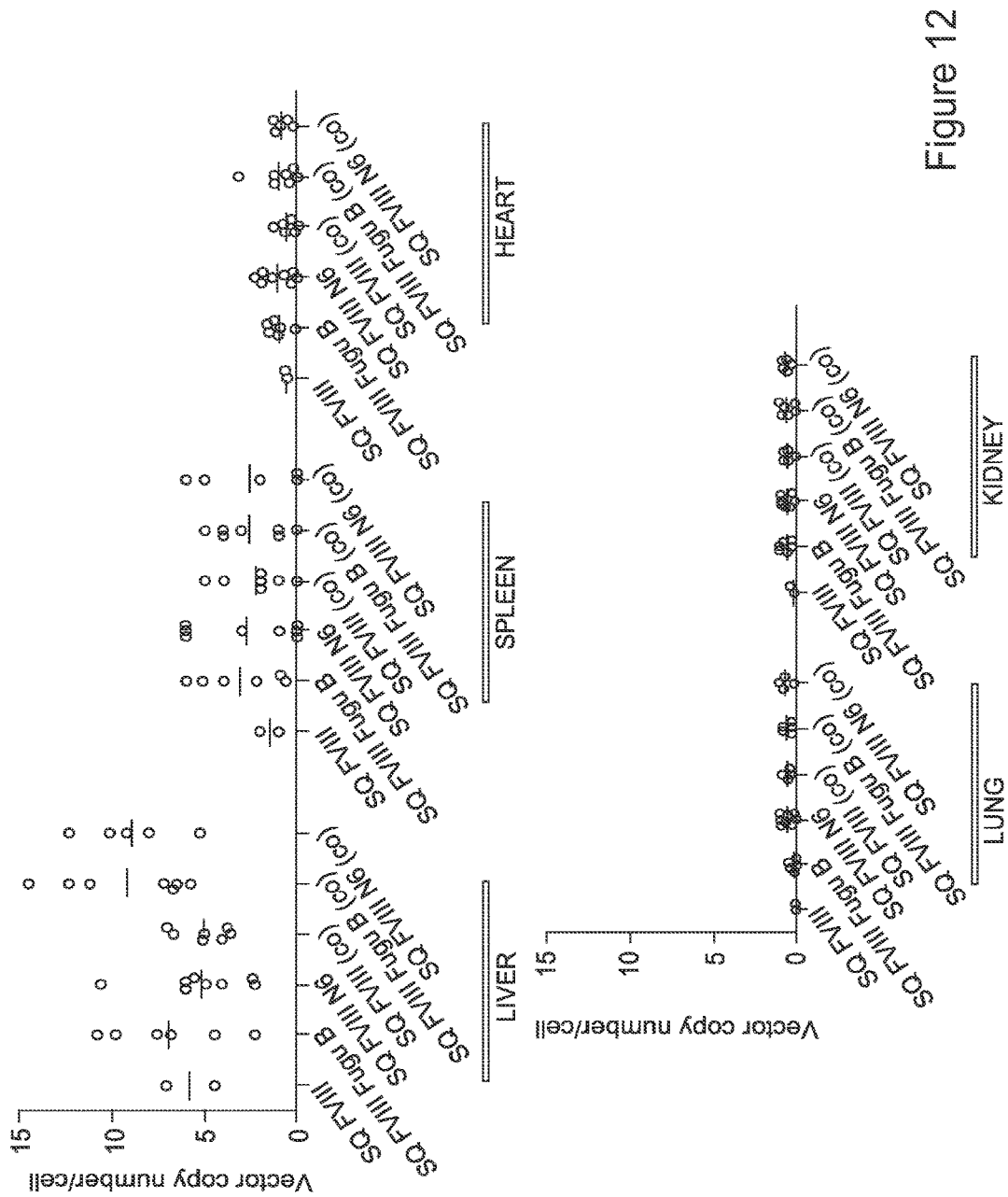

FIG. 12: Quantification of vector copy number in tissues of hemophiliac mice after intravenous injection of SIN lentiviral vectors expressing bioengineered FYIII constructs. Liver, spleen, heart, lung and kidney tissue were taken from mice sacrificed at ~250 days post neonatal injection of lentiviral vectors expressing SQ FVIII, SQ FVIII Fugu B, SQ FVIII N6, SQ FVIII (co), SQ FVIII Fugu B (co), and SQ FVIII N6 (co). Genomic DNA was extracted and viral copy number determined using qPCR. Line represents the mean of all points. No significant difference in copy number was observed between any vector group (P>0.1, Bonferroni simultaneous test).

EXAMPLE 1

Packaging of an hFVIII Expression Cassette into rAAV

The inventors have established that a 6.0 kb expression cassette containing the BDD-FVIII cDNA under the control of the previously described liver specific promoter (LP1) can be efficiently packaged into rAAV vectors pseudotyped with serotype 5 capsid proteins (rAAV5-LP1-BDD-hFVIII) using the conventional 3 plasmid transient transfection method. Tail vein administration of only 2×10$^9$ rAAV5-LP1-BDD-hFVIII particles into adult male FVIIIKO mice resulted in FVIII coagulation activity of 18±5.3% using a chromogenic assay (FIG. 1), which is significantly above the level required for amelioration of the bleeding diathesis in humans (>1% of normal).

Scale-Up of rAAV-hFVIII Vector Production

The inventors have established a GMP compatible, simple, scalable rAAV production method using the baculovirus expression vector and insect cells. A key advantage of the baculovirus system is the ease with which production can be scaled up. It has been possible to generate 1×10$^{14}$ vector genomes (vg) from a single production run using a bioreactor. This quantity would be sufficient for a Phase I/II HA clinical trial. Initial yields with our first generation FVIII vector (rAAV5-LP1-BDD-hFVIII) are in the order of 5×10$^{11}$ vg from 1 litre of cell culture.

Expression from Codon Optimised hFVIII

The inventors have designed an alternative hFVIII construct (codop-FVIII) to test the hypothesis that replacing infrequently used codons in the cDNA with those more commonly found in mammalian genes ("codon optimisation") will generate increased expression of hFVIII following gene transfer. A similar exercise for coagulation factors IX and VII improved expression by up to 10 fold when compared to the wild type cognates. The strategy for the design of the codop-hFVIII involved back translating the hFVIII amino acid sequence with a set of codons most frequently found in highly expressed mammalian genes. This modified sequence was then carefully scanned and codons were further modified to improve mRNA stability and remove undesirable sequences, such as excess CpG dinucleotides, and cryptic splice sites. The final designed codop-hFVIII sequence contains 1076 single by changes from the wild type N6-FVIII sequence, and is 42% A+T, relative to 56% A+T content of the wild type sequence. The codop FVIII sequence is the sequence of SEQ ID NO: 1. Initially, this codop-FVIII variant was cloned into a lentiviral vector down stream of the constitutive spleen focus-forming virus (SFFV) promoter and its potency assessed in new born FVIIIKO mice by injecting 1×10$^8$ TU into the temporal vein. For comparison two separate cohorts of newborn FVIIIKO mice were transduced with an equivalent titre of an identical vector encoding either the BDD or the more potent N6 FVIII variants. As shown in FIG. 2a, and consistent with previous reports, lentiviral vectors encoding the N6-FVIII (15±0.8% of normal) mediated 5 fold higher levels of transgene expression when compared to the BDD variant (3±0.6% of normal). In comparison, hFVIII expression in the plasma of codop-FVIII cohort of mice (283±0.21% of normal) was at least 18 fold higher than that achieved with N6-FVIII. The inventors have cloned the BDD, N6 and codop FVIII variants into their standard rAAV vector (Nathwani A. et al. Blood. 2007 Feb. 15; 109(4): 1414-1421) under the LP1 promoter. In addition, codop-FVIII has also been cloned down stream of a new smaller hybrid liver specific promoter (HLP). The HLP promoter has the sequence of SEQ ID NO: 3. Evaluation of these rAAV vectors plasmids in a transient transfection assay in HepG2 liver cell-line (FIG. 2b) showed that the LP1 rAAV vectors encoding codop-FVIII (0.38±0.06 IU/ml) mediated FVIII expression at levels that were between 4 (0.09±0.02 IU/ml) and 8 (0.05±0.02 IU/ml) fold higher than achieved with rAAV-LP1-N6-FVIII and rAAV-LP1-BDD-FVIII respectively. Collectively, therefore, these data suggest that the inventors codop-FVIII molecule is more potent than the N6-FVIII variant. Notably, the slightly smaller rAAV-HLP-codop-FVIII vector plasmid consistently generates between 30-50% higher yields of vector than rAAV-LP1-codop-FVIII.

HLP-Codop-hFVIII Expression Cassette can be Packaged into AAV Virions

The ~5.6 kb rAAV-HLP-codop-hFVIII expression cassettes exceed the 4.6 kb packaging limit of AAV vectors but was successfully packaged into AAV virions with the same efficiency as scAAV-FIX vector that is being used in ongoing clinic trial (FIG. 3A) using the conventional HEK293T transient transfection method. Others have shown that up to 6.6-kb vector sequence may be packaged into AAV virions. Additionally, Dr High's group at the University of Pennsylvania, independently verified that up to $6 \times 10^{13}$ rAAV8 pseudotyped particles of rAAV-HLP-codop-hFVIII could be derived following transient transfection from just 20 roller-bottles of HEK293 cells (Yield=$6 \times 10^4$ vg/293T cell). To demonstrate that the rAAV-HLP-codop-hFVIII vector genome was packaged in its entirety, DNA was extracted from virions derived from two separate stocks, after DNaseI treatment and separated on native and alkaline agarose gel and then assessed following ethidium bromide staining or Southern blot analysis respectively. A prominent band of approximately 5.7 kb was noted with both assessment methods (FIGS. 3B and C).

Codop-hFVIII is More Potent but as Safe as the N6 or BDD hFVIII Variants rAAV vectors pseudotyped with serotype 5 capsid encoding the codop, N6 and the BDD-hFVIII variant under the control of either the LP1 or HLP promoters were injected via the tail vein ($4 \times 10^{11}$ vg/mouse, N=3/group) of male 4-6 week C57Bl/6 mice. As shown in FIG. 4, a single tail vein administration of rAAV-LP1-codop-hFVIII resulted in 0.20±0.03 IU/ml (=20% of normal levels) of hFVIII in murine plasma without any toxicity. Expression of hFVIII was 10 fold lower in mice transduced with $4 \times 10^{11}$ vg/mouse of rAAV-LP1-N6-hFVIII (0.02±0.0003 IU/ml=2% of normal), which encodes the wild type hFVIII DNA sequence instead of codon-optimised FVIII nucleotide sequence in codop-hFVIII. This difference in expression between these two vectors which are otherwise identical is highly significant (p=0.0003, one way ANOVA). Replacing the LP1 promoter with the smaller liver specific HLP promoter resulted in marginally higher levels (0.22±0.04 IU/ml) of hFVIII in the plasma of mice transduced with $4 \times 10^{11}$ vg/kg of rAAV-HLP-codop-hFVTII when compared to the rAAV-LP1-codop-hFVIII cohort but this difference was not significant (p=0.6). The lowest level of hFVIII expression was observed in the plasma of mice that received $4 \times 10^{11}$ vg/mouse of rAAV-LP1-BDD-hFVIII (0.01±0.001 IU/ml), which approximates to 1% of normal levels. Importantly, these differences in the level of hFVIII expression were not related to vector copy number as qPCR analysis shows similar vector copy number in the genomic DNA extracted from liver of animals in each group ranging from 0.9-1 proviral copies/cell. Southern blot analysis of genomic DNA from the liver of mice transduced with LP1-codop-hFVIII at 6 weeks after gene transfer digested with Kpn-1, which twice cuts within the codop-hFVIII expression cassette, released a band of the expected size of approximately 1.9 kb (FIG. 5A). Digestion with Not-I, which is a single cutter, generated two bands of ~5 kb and ~10 kb corresponding to head-to-tail and head-to-head concatemer fragments in a ratio of 3:1 respectively. Western blot analysis showed that the codop-hFVIII is secreted as a single chain 210 kd protein, which as expected is smaller in size when compared to full length recombinant FVIII (Helixate, FIG. 5B, left lane) as two thirds of the B domain has been deleted from codop-hFVIII.

Next, different doses of rAAV5-HLP-codop-hFVIII were administered via the tail vein to male C57Bl/6 mice and plasma hFVIII levels were assessed at 6 weeks. As shown in FIG. 6A, a relatively linear relationship was observed between vector dose, plasma hFVIII levels and transgene copy number with no evidence of saturation kinetics even at the higher dose levels. Administration of $4 \times 10^{10}$ vg/mouse of rAAV5-HLP-codop-hFVIII resulted in low but detectable hFVIII expression at 0.5% of normal. The rAAV-HLP-codop-hFVIII transgene copy number in the liver of these animals was also 7 fold lower (0.12±0.06 copies/cell) that in the $4 \times 10^{11}$ vg/mouse dose cohort. An increase in the vector dose to $4 \times 10^{12}$ vg/mouse resulted in plasma hFVIII levels of around 190% of physiological levels (1.9±0.3 IU/ml). The rAAV-HLP-codop-hFVIII transgene copy number in the liver of these mice was over 330 fold higher (43.5±2.5 proviral copies/cell) than the levels observed in animals transduced with $4 \times 10^{11}$ vg/mouse. and approximately in the liver. No toxicity was observed at any of the dose levels and histological examination of the organ after necropsy at 6 weeks did not show any significant pathology. The transgene expression profile was next assessed in two cohorts of mice (n=3) following tail vein administration of $4 \times 10^{12}$ vg/mouse of rAAV-HLP-codop-hFVIII pseudotyped with serotype 5 and 8 capsid proteins. As per previous reports by the inventors with other single stranded rAAV vectors, hFVIII was detectable within two weeks of gene transfer prior to reaching steady state levels of 23±6 IU/ml and 54±12 IU/ml by 10 weeks in mice transduced with rAAV-HLP-codop-hFVIII pseudotyped with serotype 5 and 8 capsid respectively (FIG. 6B). At all time points the level of hFVIII in the rAAV8-HLP-codop-hFVIII cohort was between 2-10 fold higher when compared to the levels achieved in mice that received serotype 5 capsid pseudotyped vector. This difference is highly significant (p<0.001) and is consistent with similar serotype specific differences in rAAV mediated transduction reported previously. Plasma thrombin-antithrombin complexes (2.2±0.2 µg/l) were not elevated, indicating that supraphysiological levels of hFVIII do not induce a noticeable hypercoagulable state in mice. Finally, anti-hFVIII antibodies were not detected in the rAAV-HLP-codop-hFVIII mice at any stage after gene transfer.

rAAV-HLP-Codop-hFVIII Corrects Bleeding Diathesis in Haemophilia a Mice

To confirm correction of the bleeding phenotype, the inventors injected either $4 \times 10^{11}$ (low-dose cohort, n=3) or $5 \times 10^{12}$ (high-dose cohort, n=3) rAAV5-HLP-codop-hFVIII vector genomes into the tail vein of haemophilia A knockout mice, which are of mixed C57Bl6/J-129 Sv background and contain a deletion in exon 16 of murine FVIII. Peak hFVIII levels, as determined by a one-stage clotting assay, were 137±27% and 374±18% of normal levels in the low and high-dose cohorts of mice respectively (FIG. 7A). These levels were significantly above background (untreated HA haemophiliac (FVIIIKO) mice hFVIII:C level=<2% of normal) and significantly higher than the therapeutic of >5% of normal. There was very close concordance between hFVIII activity and antigen levels at all time points examined with an average ratio of 1.16. The bleeding time in the AAV treated and untreated F8–/– mice as well wild-type control mice was assessed using a tail clip assay. The time to first arrest of bleeding in the rAAV5-HLP-codop-hFVIII was significantly shorter (p=0.003) at 114±3 and 74±14 seconds in the low and high dose cohorts respectively when compared to untreated F8−/− mice (311±3 seconds) and comparable to that in control wild-type animals (74±20 seconds). Similarly, the amount of blood loss as assessed by spectrophotometric analysis of the haemoglobin content in saline into which the clipped mouse tail is immersed was substantially lower (p=0.002) in the rAAV5-HLP-codop-hFVIII F8−/− mice when compared to untreated F8−/− animals. Anti-hFVIII antibodies were not detected in the rAAV treated HA mice at any stage after gene transfer.

Collectively, therefore, these data suggest that the codop-hFVIII molecule is more potent than the N6-hFVIII variant. Additionally, the codop-hFVIII expression cassette appears to be well packaged into rAAV virons despite its relatively large size when compared to wild-type AAV genome. hFVIII is expressed as a single chain biologically active protein following rAAV gene transfer that is able to correct the bleeding phenotype in haemophilia A knock out animals.

EXAMPLE 2

Introduction

Hemophilia A is a serious bleeding disorder caused by a deficiency in, or complete absence of, the blood coagulation factor VIII (FVIII). It is the most common hereditary coagulation disorder with an incidence approaching around 1 in 5000 males[1]. The disorder is an attractive candidate for gene therapy because only a modest increase in FVIII plasma concentration is needed for therapeutic benefit, with levels of >1% able to achieve markedly reduced rates of spontaneous bleeding and long term arthropathy[2]. However, although preclinical results using gene therapy in animal models of hemophilia A have been encouraging, no approach as yet has been translated to clinical success where insufficient levels of FVIII expression have been observed[3].

Figure 8A:
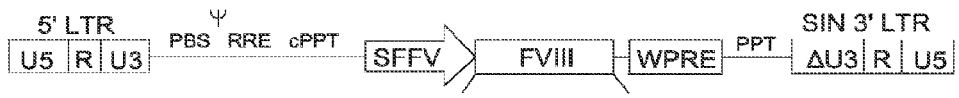
Figure 8B:
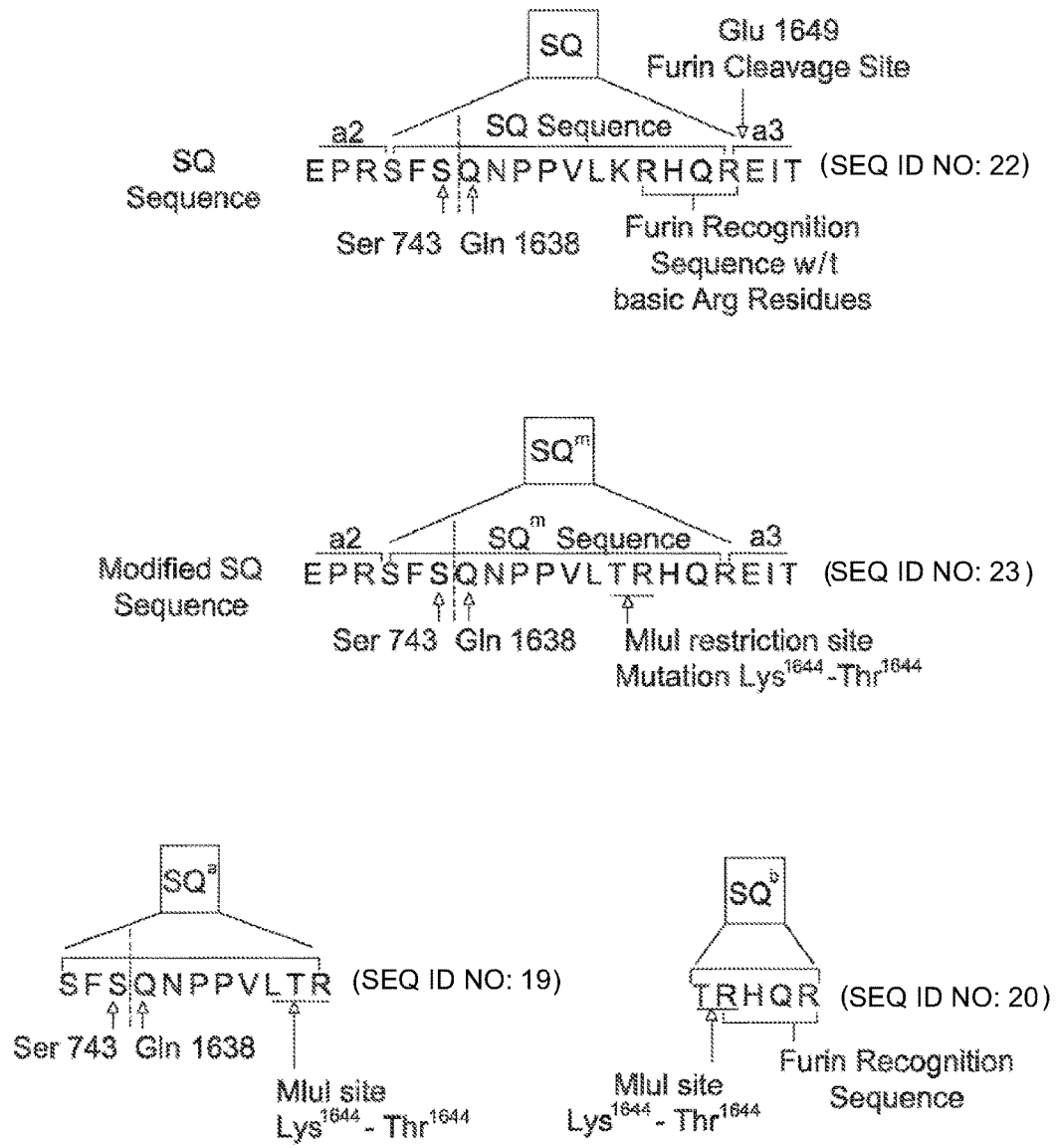

Low FVIII expression is principally caused by inefficient expression of the mRNA[4-6], a significant proportion of protein misfolding with subsequent intracellular degradation, and inefficient transport of the primary translation product from the endoplasmic reticulum (ER) to the Golgi[7; 8]. This results in expression levels of FVIII approximately 2 to 3 orders of magnitude lower than those of other comparably sized secreted proteins[4]. Insights over the past two decades into the secretion pathway, FVIII protein structure and function, and mechanisms of inhibitor development have led to the incorporation of bioengineered forms of FVIII in gene transfer systems. Bioengineering aims to improve properties such as biosynthesis, secretion efficiency, functional activity, plasma half-life, and to reduce antigenicity/immunogenicity[9]. FVIII is produced as a large 330 kDa glycoprotein with the domain structure A1-A2-B-A3-C1-C2[10; 11], where both the A and C domains have internal sequence homology and approximately 40% sequence identity to the A and C domains of factor V (FV), which shares the same domain structure[12; 13]. The B-domain, which constitutes 38% of the total sequence, shares no amino acid sequence identity with other known proteins, including the B-domain of FV. It is, however, extensively glycosylated and contains 19 of the 26 asparaginc (N)-linked glycosylation sites on the whole FVIII molecule[14]. FVIII B-domain is dispensable for procoagulant activity. FVIII in which the B-domain is deleted (BDD) and replaced by a short 11 amino acid linker (FVIII SQ; FIG. 8b) is in clinical use as a replacement recombinant FVIII product (Refacto, Wyeth Pharma)[15].

It has been shown that deletion of the entire B-domain leads to a 17-fold increase in mRNA and primary translation product, however, only a 30% increase in the levels of secreted protein, suggesting that the rate of ER-Golgi transport is actually reduced[16]. Efficient FVIII secretion requires carbohydrate-facilitated transport by LMAN1 (lectin mannosc binding-1) mediated by mannose residues of N-linked oligosaccharides post-translationally attached to the B-domain. To build on the advantages of BDD-FVIII whilst aiding LMAN1 mediated transport Miao et al. (2004)[17] added back a short B-domain sequence to the BDD-FVIII, optimally 226 amino acids and retaining 6 sites for N-linked glycosylation (226/N6). This resulted in a 10-fold increase in secretion in vitro from transfected COS-1 cells and a 5-fold increase in vivo follwing hydrodynamic hepatic gene delivery[17].

The teleost puffer fish *Fugu rubripes* is a commonly used organism for investigation of genetics. Fugu has a basic vertebrate genome and contains a similar repertoire of genes to humans, however, in 1993 it was shown that the Fugu genome is only 390 Mb, about one-eighth the size of the human genome[18]. This makes Fugu an extremely useful model for annotating the human genome and a valuable 'reference' genome for identifying genes and other functional elements. Sequence analysis of genes in the blood coagulation system showed that Fugu amino acid sequences are highly conserved relative to their human orthologues. For FVIII cDNA sequences the Fugu A1, A2, A3, C1 and C2 domains show 46, 43, 47, 52 and 50% sequence identity to human orthologues, respectively. Conversely, the Fugu factor VIII B-domain shares only 6% sequence identity to its human counterpart. However, although there is no apparent sequence conservation between B-domains the Fugu B-domain is also highly glycosylated with 11 asparagine (N)-linked glycosylation attachment sites across its 224 amino acid length[19].

In this study the inventors examined the expression of human BDD FVIII constructs containing the previously described 'SQ' B-domain element, the 226/N6 B-domain fragment and the Fugu B-domain. Constructs were tested under the control of the Spleen Focus Forming Virus (SFFV) promoter in the context of a self-inactivating (SIN) HIV-1 based lentiviral vector (LV). Furthermore, constructs were expressed from either a codon optimised or non-codon optimised cDNA sequence. Multiple transcriptional silencers and inhibitory motifs are widely distributed throughout the FVIII cDNA[4; 6; 20-22], and these sequences act as potent inhibitors of RNA production and protein formation which can hamper expression in vivo. FVIII expression for all constructs was compared in vitro by transduction of 293T cells and in vivo by intravenous injection of vector into neonatal hemophilia A mice. Varying the B-domain made a significant difference to expression of factor VIII from codon optimised cDNA sequences in vitro, however, no difference was observed in vivo. Direct comparison of bioengineered FVIII constructs showed that significantly greater levels (up to a 44-fold increase and in excess of 200% normal human levels) of active FVIII protein were detected in the plasma of mice transduced with vector expressing FVIII from a codon optimised cDNA sequence, successfully correcting the disease model. To date, this is the highest relative increase in FVIII expression following bioengineering of BDD FVIII resulting in unprecedented, stable FVIII expression in vivo using a lentiviral-based approach.

Methods

FVIII Transgene and Lentiviral Vector Construction

The expression plasmid pMT2-FVIII was obtained as a kind gift from Dr. Steven W. Pipe (University of Michigan). This plasmid contains the human FVIII gene with a Fugu B-domain. The hFVIII gene had a B-domain deletion from amino acids 740-1649 and an MluI restriction site (ACG'CGT) engineered by site directed mutagenesis at amino acid positions 739-740 causing the missense mutation Pro739 to Thr739 in the a2 domain. The Fugu B-domain had been cloned in using flanking MluI restriction sites on 5' and 3' creating a 4935 bp hFVIII Fugu B gene. The FVIII Fugu B gene was removed in three parts using a digest with XhoI and KpnI to remove a 1.83 kb fragment, a partial digest with KpnI and MluI to remove a 1.06 kb fragment, and PCR amplification of the last 2.066 kb section using primers that created MluI and SbfI sites on the 5' and 3' ends, respectively. Each section was sequentially cloned into pLNT/SFFV-MCS using the same enzymes to create pLNT/SFFV-FVIII Fugu B. The construct was fully sequenced upon completion. pLNT/SFFV-BDD FVIII was produced by digest of pLNT/SFFV-FVIII Fugu B with MluI to remove the Fugu B-domain and religation. The 226/N6 B-domain sequence was manufactured by GeneArt (Regensburg, Germany) to produce a standard GeneArt plasmid containing 226/N6; pGA_N6_nonopt, the sequence was obtained by taking the first 678 bp of the human FVIII B-domain (cDNA found at Genbank: A05328), 5' and 3' flanking MluI sites were then added. N6 was then removed from pGA_N6_nonopt and ligated into pLNT/SFFV-BDD FVIII using MluI to create pLNT/SFFV-FVIII N6. The SQ cDNA sequence was obtained from[23] and was modified to contain an MluI site (underlined) to give the SQ$^m$ cDNA sequence: 5'-AGC'TTC'AGC'CAG'AAC'CCC'CCC'GTG'CTG' ACG'CGT'CAC'CAG'CGG-3' (SEQ ID NO: 8) (FIG. 8b). LNT/SFFV-SQ FVIII Fugu B was produced by site directed mutagenesis performed by Eurofins MWG Operon (Ebersberg, Germany) to add the flanking SQa$^a$ and SQ$^b$ (FIG. 8b) sequences into the plasmid pLNT/SFFV-FVIII Fugu B to produce pLNT/SFFV-SQ FVIII Fugu B. pLNT/SFFV-SQ FVIII was then produced by removal of the Fugu B-domain from pLNT/SFFV-SQ FVIII Fugu B by digest with MluI and religation. pLNT/SFFV-SQ FVIII N6 was produced by removal of the 226/N6 B-domain from pGA_N6_nonopt by digestion with MluI and ligation into pLNT/SFFV-SQ FVIII. In this construct there is a repeat of the 11aa SQ$^a$ sequence caused by the insertion of the N6 B-domain into the SQ$^m$ sequence. Codon optimised sequences were created by analysis of the SQ FVIII Fugu B cDNA and adaption of the codon usage to the bias of *Homo sapiens* using codon adaptation index (CAI) performed by GeneArt (Regensburg, Germany) using their in-house proprietary software GeneOptimizer®. Optimisation also removed cis-acting sequence motifs including internal TATA-boxes, chi-sites and ribosomal entry sites, AT- or GC-rich sequence stretches, AU-rich elements, inhibitory and cis-acting repressor sequence elements, repeat sequences, RNA secondary structures, and all cryptic splice sites. Optimisation of SQ FVIII Fugu B included the removal of 14 splice sites, an increase in GC-content from ~45% to ~60% and an increase in CAI from 0.74 to 0.97. A Kozak sequence was introduced to increase translation initiation, and two stop codons were added to ensure efficient termination. The optimised gene retained the B domain flanking MluI restriction sites on the Fugu B domain and has 75.8% sequence similarity to the original non-optimised sequence. The optimised gene was cloned into pLNT/SFFV-MCS to give the plasmid pLNT/SFFV-SQ FVIII Fugu B (co). The plasmid pLNT/SFFV-SQ FVIII (co) was created by digestion of pLNT/SFFV-SQ FVIII Fugu B (co) with MluI and religation. The 226/N6 B domain sequence from pGA_N6_nonopt was codon optimised and manufactured by GeneArt. It was received in the plasmid pGA_N6_opt and as the MluI restriction sites were maintained cloned directly into the pLNT/SFFV-SQ FVIII (co) plasmid to obtain the construct pLNT/SFFV-SQ FVIII N6 (co), again, this construct will contain an 11aa SQ$^a$ repeat sequence caused by the insertion of the B domain into the SQ$^m$ sequence. Each construct was fully sequenced before testing. The codon optimised SQ FVIII N6 sequence is the sequence of SEQ ID NO: 4. The codon optimised SQ FVIII sequence is the sequence of SEQ ID NO: 5. The codon optimised SQ FVIII Fugu B sequence is the sequence of SEQ ID NO: 6.

Lentiviral Vector Production and Titration

Lentiviral vectors were produced by transient cotransfection of HEK293T (293T) cells with 3 plasmids (the lentiviral vector, pMD.G2 [vesicular stomatitis virus glycoprotein (VSV-G) envelope plasmid], and pCMVA8.91 [packaging plasmid, both produced by Plasmid Factory, Bielefeld, Germany], employing polyethylenimine (Sigma-Aldrich, Poole, UK). Viral supernatant was harvested and concentrated using ultracentrifugation (25,000×g for 2 h at 4° C.). Aliquots of viruses were stored at −80° C. The titres of all lentiviral vectors were determined using a colorimetric reverse transcriptase (RT) enzyme-linked immunosorbent assay (ELISA) kit (Roche, West Sussex, UK) according to the manufacturer's instructions, and qPCR to determine an approximate titre in vector genomes per mL (vg/mL).

Measurement of FVIII Activity

The cofactor activity of blood plasma samples and in vitro cell culture media samples was assessed using the Biophen Factor VIII:C Chromagenic Assay (Biophen, Quadratech Diagnostics, Epsom, UK) as per manufacturer's instructions. Samples were diluted 1:20 to 1:40 in sample diluent provided and analysed in duplicate. A standard curve in % FVIII cofactor activity was constructed by diluting normal control plasma (Biophen, Quadratech Diagnostics) 1:20, carrying out four 1:2 serial dilutions, and running in duplicate. Abnormal control plasma (Biophen, Quadratech Diagnostics) was also used as a further quality control for the assay.

Lentiviral Transduction 293T cells were maintained in Dulbecco modified Eagle medium (DMEM) (Gibco Life Technologies Ltd, Paisley, UK) and supplemented with 50 IU/mL penicillin, 50 μg/mL streptomycin, and 10% heat-inactivated fetal calf serum (FCS; Gibco). For lentiviral transduction five wells of 1×10$^5$ 293 T cells were transduced with serial dilutions of vector in a total volume of 300 μL DMEM+10% FCS. 48 hours post-transduction cell media was changed for 500 μL OptiMEM (Gibco). After a further 24 hours incubation media was collected from all wells and assayed for factor VIII activity using a FVIII chromogenic assay. Genomic DNA was then extracted from cells and viral copy number quantified using real-time quantitative PCR (qPCR).

In Vivo Methods

All mice were handled according to procedures approved by the UK Home Office and the Imperial College London Research Ethics Committee. Haemophilia A mice (F8$^{tm2Kaz}$) generated by deletion of exon 17[24] were maintained on a 129SV background. 0-1 day old neonatal mice were subject to brief (<5 minutes) hypothermic anaesthesia and 400 μL of concentrated lentiviral vector (equivalent to 4×10$^7$-1×10$^8$ transducing units per mouse) injected into the superficial temporal vein. For coagulation factor assays 1004, of peripheral blood was collected from anaesthetised mice by tail vein bleed. Blood was mixed immediately in a ratio of 1:9 with sodium citrate, centrifuged at 13000 rpm in a micro-centrifuge for five minutes and plasma transferred to fresh micro-centrifuge tube and stored at −20° C. before assaying.

Determination of Vector Copy Number by Real-Time Quantitative PCR

Genomic DNA was extracted from cells using a standard salting-out method[25]. Real-time qPCR was carried out in triplicate for each sample to determine viral copy number. qPCR was performed using an ABI 7000 Sequence Detection System (ABI, Applied Biosystems, Warrington, United Kingdom). Total viral DNA was quantified using primers 5'-TGTGTGCCCGTCTGTTGTGT-3' (SEQ ID NO: 9) and 5'-GAGTCCTGCGTCGAGAGAGC-3' (SEQ ID NO: 10) and Taqman probe (FAM) 5'-CGCCCGAACAGGGACTT-GAA-3' (TAMRA) (SEQ ID NO: 11). The mouse titin gene (Ttn) was used as an endogenous 2-copy gene control for mouse cells and was quantified using primers 5'-AAAAC-GAGCAGTGACCTGAGG-3' (SEQ ID NO: 12) and 5'-TTCAGTCATGCTGCTAGCGC-3' (SEQ ID NO: 13) and Taqman probe (FAM) 5'-TGCACG-GAATCTCGTCTCAGTC-3' (TAMRA) (SEQ ID NO: 14). The human beta-actin gene (ACTS) was used as an endogenous 2-copy gene control for HEK-293T cells and was quantified using primers 5'-TCACCCACAAGTTGC-CCATCTACGA-3' (SEQ ID NO: 15) and 5'-CAGCG-GAACCGCTCATTGCCAATGG-3' (SEQ ID NO: 16) and Taqman probe (FAM) 5'-ATGCCCTCCCCCATGCCATC-CTGCGT-3' (TAMRA) (SEQ ID NO: 17).

Statistical Analysis

Data are expressed as mean values plus or minus SD. Statistical analyses were performed using a general linear model (GLM) based on one-way analysis of variance (ANOVA) with individual pairwise comparisons performed using Bonferroni simultaneous tests (Minitab software, Myerstown, Pa.).

Results

Generation of Bioengineered FVIII Variants and Production of FVIII-Expressing SIN Lentiviral Vectors To overcome low protein expression associated with haemophilia A gene transfer applications the inventors investigated the expression from bioengineered FVIII transgenes containing various B-domain elements from codon optimised or non-codon optimised cDNA sequences. The following FVIII variants were generated (FIG. 8a): BDD human FVIII containing a B-domain deletion between amino acids 740-1649 with a missense mutation Pro739 to Thr739 in the a2 domain previously described by Miao et al. (2004)[17] (herein referred to as BDD FVIII); BDD FVIII containing the 201aa Fugu B-domain containing 11 (N)-linked glycosylation sites between aa's 740 and 1649 (herein referred to as FVIII Fugu B); BDD FVIII containing the 226aa/N6 human B-domain fragment containing 6 (N)-linked glycosylation sites between aa's 740 and 1649 previously described by Miao et al. (2004)[17] (herein referred to as FVIII N6); BDD FVIII containing a modified 14-amino acid SQ activation peptide $SQ^m$ between aa's 740 and 1649 (SFSQNPPVLTRHQR) (SEQ ID NO: 18) (missense mutation Lys to Thr underlined), contains the RHQR furin recognition sequence to increase intracellular cleavage, the original SQ activation peptide sequence described by Sandberg et al. (2001)[23] (herein referred to as SQ FVIII); SQ FVIII containing the Fugu B-domain inserted into the $SQ^m$ sequence. This causes the $SQ^m$ sequence to be split either side of the B-domain insert with the N-terminal sequence (SFSQNPPVLTR) (SEQ ID NO: 19) is referred to as $SQ^a$, and the C-terminal sequence containing the furin recognition site RHQR as $SQ^b$ (TRHQR) (SEQ ID NO: 20) (herein referred to as SQ FVIII Fugu B); SQ FVIII containing the 226aa/N6 B-domain inserted into the $SQ^m$ sequence creating $SQ^a$ and $SQ^b$ sequences on the N- and C-terminal sides of the B-domain, respectively. In this construct there is a repeat of the 11aa $SQ^a$ sequence caused by the insertion of the N6 B-domain into the $SQ^m$ sequence. It is unknown the effect that this repeat will have upon FVIII secretion and function (herein referred to as SQ FVIII N6). Constructs 'SQ FVIII (co)', 'SQ FVIII Fugu B (co)' and 'SQ FVIII N6 (co)' are identical in amino acid structure as constructs 'SQ FVIII', 'SQ FVIII Fugu B' and SQ FVIII N6', respectively, but are translated from a codon optimised cDNA sequence (FIG. 8a). Representation of SQ, $SQ^m$, $SQ^a$, and $SQ^b$ are shown in FIG. 8b. All constructs were cloned into a SIN lentiviral backbone under control of the SFFV promoter and transgene sequences were confirmed by automated DNA sequencing.

Vectors were produced for all nine factor VIII constructs and tested for physical titre using the reverse transcriptase protein assay. They were then tested using qPCR to determine an approximate titre in vector genomes per mL (vg/mL) (Table 1). There was no substantial difference in titre between constructs.

TABLE 1

Physical titre of FVIII vectors as determined by reverse transcriptase assay and qPCR.

| Virus | Average Reverse Transcriptase (ng/μL) | Estimated Titre (TU/mL) | Titre (vg/mL) |
|---|---|---|---|
| BDD FVIII | 10.9 | $3.71 \times 10^9$ | $1.14 \times 10^8$ |
| FVIII Fugu B | 46.5 | $1.58 \times 10^{10}$ | $1.58 \times 10^9$ |
| FVIII N6 | 30.7 | $1.04 \times 10^{10}$ | $1.07 \times 10^9$ |
| SQ FVIII | 68.3 | $2.32 \times 10^{10}$ | $2.91 \times 10^9$ |
| SQ FVIII Fugu B | 44.8 | $1.52 \times 10^{10}$ | $1.18 \times 10^9$ |
| SQ FVIII N6 | 78.0 | $2.65 \times 10^{10}$ | $2.0 \times 10^9$ |
| SQ FVIII (co) | 69.6 | $2.37 \times 10^{10}$ | $4.45 \times 10^9$ |
| SQ FVIII Fugu B (co) | 71.8 | $2.40 \times 10^{10}$ | $2.65 \times 10^9$ |
| SQ FVIII N6 (co) | 87.9 | $2.99 \times 10^{10}$ | $3.39 \times 10^9$ |

Quantification of reverse transcriptase (RT) protein concentration in viral stocks, measured by performing a RT colorimetric assay, quantified in ng/μL and estimated titre calculated from this. Mean shown of n = 3. Quantification of titre in vector genomes per mL was determined using qPCR. $1 \times 10^5$ 293T cells were transduced with a serial dilution of vector, after 72 hours genomic DNA was extracted from cells and qPCR carried out for both WPRE and the human housekeeping gene β-actin. Mean shown of n = 5.

Expression of FVIII In Vitro

Relative FVIII protein expression was measured for each construct in the human embryonic kidney cell line 293T. Cells were transduced with a serial dilution of vector and cultured for 48 hours, after which cells were washed, fresh serum free media added and chromogenic assays performed after a further 24 hours to determine FVIII activity. Genomic DNA was also extracted from cells to determine viral copy number by qPCR. Expression values were then normalised against copy number allowing accurate values for FVIII protein expression per gene copy to be determined (FIG. 9). All constructs produced detectable FVIII activity using a chromogenic assay (FIG. 9) and FVIII antigen by ELISA (data not shown).

Cells transduced with constructs expressed from non-codon optimised cDNA sequences produced on average 1.40 to 2.89% FVIII activity/mL/24 hr/vector copy number. There was no significant difference in expression of FVIII between equivalent constructs where the $SQ^m$, $SQ^a$ and $SQ^b$ activation peptide sequences were present (P>0.05). In addition, there was no significant increase in expression where the Fugu B or 226/N6 B-domains were present in comparison to SQ FVIII or BDD FVIII constructs (P>0.05).

However, a highly significant increase in expression was observed with constructs expressed from codon optimised cDNA sequences. Cells expressing SQ FVIII (co), SQ FVIII Fugu B (co), and SQ FVIII N6 (co) produced 22.89±3.68, 47.20±2.71, and 35.8±2.39% FVIII activity/mL/24 hr/vector copy number, respectively, a 13- to 16-fold increase in comparison to expression from equivalent non-codon optimised cDNA sequences (P<0.0001). A significant increase in expression was also observed from constructs containing the Fugu and 226/N6 B domains in comparison to SQ FVIII (co) (P<0.0001), furthermore, the SQ FVIII Fugu B (co) had expression significantly higher than both SQ FVIII (co) and SQ FVIII N6 (co) (P<0.0001).

Comparison of FVIII Expression In Vivo after Intravenous Delivery of Vector into Neonatal Haemophilia a Mice SQ-containing FVIII expression cassettes were tested in vivo. Six constructs; SQ FVIII, SQ FVIII Fugu B, SQ FVIII N6, SQ FVIII (co), SQ FVIII Fugu B (co), and SQ FVIII N6 (co) were tested by direct intravenous injection of lentiviral vector into neonatal (0-1 day old) haemophiliac (FVIIIKO) mice. All mice received between $4.72 \times 10^7$ and $1.78 \times 10^8$ vector genomes (vg) with 6 to 10 mice injected per vector group. Blood plasma samples were collected via tail vein bleed approximately every 30 days for a total of ~250 days. FVIII activity was assessed using a functional chromogenic assay.

Functional FVIII was detected in the plasma of all transduced mice at all time points (FIG. 10). Plasma from mice transduced with vector containing non-codon optimised FVIII sequences; SQ FVIII, SQ FVIII Fugu B, or SQ FVIII N6 contained on average 5.72%±2.31%, 7.79%±3.66%, and 9.53%±2.24% normal human FVIII activity, respectively, for the duration of the experiment. The ability to clot rapidly following tail vein bleeds indicated that the mice treated with sequences SQ FVIII Fugu B, or SQ FVIII N6 were able to achieve adequate haemostasis, however 4 of the 6 mice injected in the SQ FVIII vector group did not survive, indicating that the levels of FVIII were insufficient to correct the murine haemophilia A phenotype. None of the other vector groups showed morbidity associated with low FVIII expression. For mice transduced with vector containing codon optimised FVIII cDNA sequences; SQ FVIII (co), SQ FVIII Fugu B (co), or SQ FVIII N6 (co), average FVIII levels were detected at 256.1%±63.4%, 232.2%±74.1%, and 283.7%±56.2% normal human FVIII activity, respectively, for the duration of the experiment. This is a 44-, 29-, and 29-fold increase in expression for SQ FVIII (co), SQ FVIII Fugu B (co), and SQ FVIII N6 (co), respectively, in comparison to expression from equivalent non-codon optimised sequences (P<0.0001, Bonferroni simultaneous test). Furthermore, no substantial loss in FVIII expression was observed in any vector groups. Importantly, no significant difference in expression was observed for constructs containing different B-domain elements for vectors containing codon optimised or non-codon optimised cDNA sequences (FIG. 11).

Analysis of Viral Copy Number in the Organs of Transduced Mice

From 187 and 246 days post-injection, mice were sacrificed to determine vector copy number in liver, spleen, heart, lung and kidney tissue by real time qPCR (FIG. 12). Vector genomes were detected predominantly in the liver and spleen tissue with negligible copies in heart, lung and kidney tissues for all mice in all vector groups. Liver tissue taken from mice transduced with vector containing non-codon optimised cDNA sequences contained an average of 5.75, 6.97 and 5.25 vector copies per cell for SQ FVIII, SQ FVIII Fugu B, and SQ FVIII N6, respectively. In spleen tissue average copy number was 1.50, 3.13 and 2.75 copies per cell for SQ FVIII, SQ FVIII Fugu B, and SQ FVIII N6, respectively. There was no significant difference in the vector copy number detected in liver tissues of animals injected with vector containing codon optimised sequences (P>0.1, Bonferroni simultaneous test). Average copy number in liver tissue was detected at 5.04, 9.17 and 8.80 copies per cell, and in spleen tissue copy was 2.28, 2.57 and 2.60 copies per cell, for SQ FVIII (co), SQ FVIII Fugu B (co), and SQ FVIII N6 (co), respectively. In all cases, similar copy number was found in all tissues for all animals regardless of vector group.

DISCUSSION mRNA instability, interactions with resident ER chaperone proteins, and the requirement for carbohydrate-facilitated transport from the ER to the Golgi apparatus means that FVIII is expressed at much lower levels from mammalian cells than other proteins of similar size and complexity[7; 26]. This has been a limiting factor both in the commercial production of recombinant FVIII for replacement therapy and in the success of gene therapy for haemophilia A. A number of bioengineered forms of human FVIII have been incorporated into gene transfer systems and have been shown to have enhanced expression both in vitro and in vivo. B-domain deleted (BDD) factor VIII constructs are used widely in gene transfer experiments as there is no loss of FVIII procoagulant function and its smaller size is more easily incorporated into vectors. A variation of this construct is a BDD FVIII containing the 14 amino acid link SQ between the A2 and A3 domains, currently produced as a recombinant product and marketed as Refacto™ (Wyeth)[23]. The SQ link has previously been shown to promote efficient intracellular cleavage of the primary single chain translation product of FVIII as it contains the intracellular furin recognition and cleavage site[21; 27]. This construct has been incorporated into plasmid vectors where it has conferred therapeutic levels of expression[28-30]. Miao et al., in 2004[17] have also shown that after plasmid transfection of COS-1 cells a human BDD FVIII construct containing the first 226 amino acids of the B-domain including 6 N-linked asparagine glycosylation sites was secreted 4-fold more efficiently in comparison to BDD FVIII and 5-fold more efficiently in vivo following hydrodynamic hepatic gene delivery[17]. This construct has now been incorporated into many gene transfer vectors including plasmid[31], lentiviral vectors[32], and gammaretroviral vectors[33] and is more efficiently secreted both in vitro[17; 33-35] and in vivo[17; 35].

One of the significant limitations in the generation of efficient viral gene delivery systems for the treatment of hemophilia A by gene therapy is the large size of the FVIII cDNA. The goal of this study was to investigate the effect of FVIII expression cassettes with various B-domain constructs. These consist of SQ FVIII, FVIII N6 and a BDD FVIII construct containing the entire B-domain from the puffer fish *Fugu rubripes* which contains 11 N-linked asparagine glycosylation sites which potentially would promote more efficient trafficking from the ER to the Golgi and therefore be more efficiently secreted. We also investigated the expression of these constructs from cDNA sequences which had been codon optimised for expression in *Homo sapiens*. All constructs were tested using a SIN lentiviral vector, however, the results are applicable to any gene delivery system. Our study found that in vitro no difference in FVIII expression was found between constructs with or without the modified SQ sequence. Incorporation of B-domain regions into constructs also did not cause a significant increase in expression for non-codon optimised constructs in comparison to their B-domain deleted equivalents. However, for codon optimised sequences significantly higher expression of both SQ FVIII Fugu B (co) and SQ FVIII N6 (co) were observed in comparison to SQ FVIII (co). A 13- to 16-fold increase in expression of functional factor VIII per integrated gene copy were also observed from codon optimised sequences.

In vivo, after neonatal injection of a similar number of lentiviral vector genomes the presence of a B-domain did not significantly affect the steady state levels of circulating FVIII activity for either codon optimised or non-codon optimised constructs. However, we observed a 29- to 44-fold increase in steady state plasma levels of functional FVIII in hemophilia A mice to levels above 200% normal human FVIII expression from codon optimised constructs in comparison to non-codon optimised equivalents. Importantly, these levels of circulating FVIII were associated with a correction of the bleeding diatheses. In contrast, the levels of FVIII activity observed in mice treated with non-codon optimised FVIII expression cassettes were associated with fatal haemorage following tail bleeds.

Multiple transcriptional silencers and inhibitory sequences are widely distributed throughout the FVIII cDNA[4; 6; 21; 22] and the increased expression following codon optimisation may be in part due to the elimination of such sequences. However, deletion of the entire B-domain which led to a 17-fold increase in mRNA and primary translation product only resulted in a 30% increase in the levels of secreted protein, suggesting that the rate of ER-Golgi transport was reduced[16] and that levels of FVIII mRNA were not limiting expression. The introduction of multiple N-linked glycosylation sites known to be important in ER-Golgi transport of FVIII increased levels of secreted FVIII, suggesting that the rate of ER-Golgi transport may be a rate limiting step[17]. However, a significant amount of FVIII within the ER never transits to the Golgi compartment due to a failure to fold correctly and misfolded FVIII accumulation in the ER can result in oxidative damage and apoptosis, perhaps suggesting that FVIII folding is the rate limiting step in FVIII expression[34]. Although protein secondary structure is determined primarily by the amino acid sequence, protein folding within the cell is affected by a range of factors: these include interaction with other proteins (chaperones) and ligands, translocation through the ER membrane and redox conditions. The rate of translation can also affect protein folding and it has been suggested that codon usage may be a mechanism to regulate translation speed and thus allow stepwise folding of individual protein domains[36; 37]. FVIII is a complex multi-domain protein in which nonsequential segments of the nascent polypeptide chain may interact in the three dimensional fold. Ribosome stalling at 'rare' codons may therefore lead to alternative folding pathways generating altered conformations and potentially misfolded protein. A potential explanation for the observed effect of codon optimised sequences utilised in this study may be that they allow efficient translation and transport across the ER membrane allowing the nascent FVIII polypeptide chain to fold correctly leading to the increased levels of secreted FVIII observed in vitro and in vivo.

Expression of >200% is not required in hemophilia patients, and production of such high levels of FVIII may be detrimental to producer cells[4; 34]. However, a major advantage of the optimised sequence is the ability to minimize the number of genetically modified cells needed to produce therapeutic levels, thereby reducing the risk of insertional mutagenesis and insertion site-dependent positional effects. Also, the use of strong, ubiquitous promoter elements such as SFFV that were previously required to drive high expression of FVIII constructs could be replaced by weaker, tissue specific promoters which are less prone to transcriptional silencing[31].

Previous in vivo studies have demonstrated expression of therapeutic levels of FVIII in vivo in adult haemophilia A mice after systemic injection of vector[32; 38-40], transplant of transduced bone marrow cells[31; 33], transplant of transduced bone marrow cells with targeted platelet-specific expression[41; 42], and transplant of transduced blood outgrowth endothelial cells[43]. However, FVIII expression levels mediated from many of these approaches have been low (1-5% normal human) and expression transient due to formation of neutralising antibodies. In this study we used a lentiviral gene delivery system to investigate FVIII expression from FVIII constructs containing various B-domains from non-codon optimised and codon optimised cDNA sequences. We observed a dramatic increase in the level of secreted FVIII from a codon optimised cDNA using this system, however, as this expression cassette is only ~5 kb in size it is applicable for any viral (including AAV) or non-viral gene delivery system and will allow the development of safer, more efficacious vectors for gene therapy of haemophilia A.

REFERENCES

1. Hoyer L W. Hemophilia A. N. Engl. J. Med. 1994; 330:38-47.
2. High K A. Gene transfer as an approach to treating hemophilia. Semin. Thromb. Hemost. 2003; 29:107-120.
3. Viiala N O, Larsen S R, Rasko J E. Gene therapy for hemophilia: clinical trials and technical tribulations. Semin. Thromb. Hemost. 2009; 35:81-92.
4. Lynch C M, Israel D I, Kaufman R J, Miller A D. Sequences in the coding region of clotting factor VIII act as dominant inhibitors of RNA accumulation and protein production. Hum. Gene Ther. 1993; 4:259-272.
5. Kaufman R J, Wasley L C, Davies M V et al. Effect of von Willebrand factor coexpression on the synthesis and secretion of factor VIII in Chinese hamster ovary cells. Mol. Cell Biol. 1989; 9:1233-1242.
6. Hoeben R C, Fallaux F J, Cramer S J et al. Expression of the blood-clotting factor-VIII cDNA is repressed by a transcriptional silencer located in its coding region. Blood 1995; 85:2447-2454.
7. Dorner A J, Bole D G, Kaufman R J. The relationship of N-linked glycosylation and heavy chain-binding protein association with the secretion of glycoproteins. J. Cell Biol. 1987; 105:2665-2674.
8. PIPE S W, Kaufman R J. Factor VIII C2 domain missense mutations exhibit defective trafficking of biologically functional proteins. J. Biol. Chem. 1996; 271:25671-25676.

9. PIPE SW. The promise and challenges of bioengineered recombinant clotting factors. J. Thromb. Haemost. 2005; 3:1692-1701.
10. Fang H, Wang L, Wang H. The protein structure and effect of factor VIII. Thrombosis Research 2007; 119:1-13.
11. Lenting P J, van Mourik J A, Mertens K. The life cycle of coagulation factor VIII in view of its structure and function. Blood. 1998; 92:3983-3996.
12. Kane W H, Davie E W. Cloning of a cDNA coding for human factor V, a blood coagulation factor homologous to factor VIII and ceruloplasmin. Proc. Natl. Acad. Sci. U.S.A 1986; 83:6800-6804.
13. Jenny R J, Pittman D D, Toole J J et al. Complete cDNA and derived amino acid sequence of human factor V. Proc. Natl. Acad. Sci. U.S.A 1987; 84:4846-4850.
14. PIPE SW. Functional roles of the factor VIII B domain. Haemophilia. 2009
15. Toole J J, Pittman D D, Orr E C et al. A large region (approximately equal to 95 kDa) of human factor VIII is dispensable for in vitro procoagulant activity. Proc. Natl. Acad. Sci. U.S.A. 1986; 83:5939-5942.
16. Pittman D D, Marquette K A, Kaufman R J. Role of the B domain for factor VIII and factor V expression and function. Blood. 1994; 84:4214-4225.
17. Miao H Z, Sirachainan N, Palmer L et al. Bioengineering of coagulation factor VIII for improved secretion. Blood. 2004; 103:3412-3419.
18. Brenner S, Elgar G, Sandford R et al. Characterization of the pufferfish (Fugu) genome as a compact model vertebrate genome. Nature 1993; 366:265-268.
19. Davidson C J, Hirt R P, Lal K et al. Molecular evolution of the vertebrate blood coagulation network. Thromb. Haemost. 2003; 89:420-428.
20. Chuah M K, VANDENDRIESSCHE T, Morgan R A. Development and analysis of retroviral vectors expressing human factor VIII as a potential gene therapy for hemophilia A.
Hum. Gene Ther. 1995; 6:1363-1377.
21. Koeberl D D, Halbert C L, Krumm A, Miller A D. Sequences within the coding regions of clotting factor VIII and CFTR block transcriptional elongation. Hum. Gene Ther. 1995; 6:469-479.
22. Fallaux F J, Hoeben R C, Cramer S J et al. The human clotting factor VIII cDNA contains an autonomously replicating sequence consensus- and matrix attachment region-like sequence that binds a nuclear factor, represses heterologous gene expression, and mediates the transcriptional effects of sodium butyrate. Mol. Cell Biol. 1996; 16:4264-4272.
23. Sandberg H, Almstedt A, Brandt J et al. Structural and functional characteristics of the B-domain-deleted recombinant factor VIII protein, r-VIII SQ. Thromb. Haemost. 2001; 85:93-100.
24. Chuah M K, Schiedner G, THORREZ L et al. Therapeutic factor VIII levels and negligible toxicity in mouse and dog models of hemophilia A following gene therapy with high-capacity adenoviral vectors. Blood 2003; 101: 1734-1743.
25. Miller S A, Dykes D D, Polesky H F. A simple salting out procedure for extracting DNA from human nucleated cells. Nucleic Acids Res. 1988; 16:1215.
26. Marquette K A, Pittman D D, Kaufman R J. A 110-amino acid region within the A1-domain of coagulation factor VIII inhibits secretion from mammalian cells. J. Biol. Chem. 1995; 270:10297-10303.
27. Lind P, Larsson K, Spira J et al. Novel forms of B-domain-deleted recombinant factor VIII molecules. Construction and biochemical characterization. Eur. J. Biochem. 1995; 232:19-27.
28. Doering C B, Denning G, Dooriss K et al. Directed engineering of a high-expression chimeric transgene as a strategy for gene therapy of hemophilia A. Mol. Ther. 2009; 17:1145-1154.
29. Doering C B, Healey J F, Parker E T, Barrow R T, Lollar P. High level expression of recombinant porcine coagulation factor VIII. J. Biol. Chem. 2002; 277:38345-38349.
30. Ye P, Thompson Ark., Sarkar R et al. Naked DNA transfer of Factor VIII induced transgene-specific, species-independent immune response in hemophilia A mice. Mol. Ther. 2004; 10:117-126.
31. Dooriss K L, Denning G, Gangadharan B et al. Comparison of factor VIII transgenes bioengineered for improved expression in gene therapy of hemophilia A. Hum. Gene Ther. 2009; 20:465-478.
32. Sinn P L, Goreham-Voss J D, Arias A C et al. Enhanced gene expression conferred by stepwise modification of a nonprimate lentiviral vector. Hum. Gene Ther. 2007; 18:1244-1252.
33. Ramezani A, Hawley R G. Correction of murine hemophilia A following nonmyeloablative transplantation of hematopoietic stem cells engineered to encode an enhanced human factor VIII variant using a safety-augmented retroviral vector. Blood 2009; 114:526-534.
34. Malhotra J D, Miao H, Zhang K et al. Antioxidants reduce endoplasmic reticulum stress and improve protein secretion. Proc. Natl. Acad. Sci. U.S.A 2008; 105:18525-18530.
35. Cerullo V, Seiler M P, Mane V et al. Correction of Murine Hemophilia A and Immunological Differences of Factor VIII Variants Delivered by Helper-dependent Adenoviral Vectors. Mol. Ther. 2007;
36. Marin M. Folding at the rhythm of the rare codon beat. Biotechnol. J. 2008; 3:1047-1057.
37. Tsai C J, Sauna Z E, Kimchi-Sarfaty C et al. Synonymous mutations and ribosome stalling can lead to altered folding pathways and distinct minima. J. Mol. Biol. 2008; 383:281-291.
38. Kootstra N A, Matsumura R, Verma I M. Efficient production of human FVIII in hemophilic mice using lentiviral vectors. Mol. Ther. 2003; 7:623-631.
39. Park F, Ohashi K, Kay M A. Therapeutic levels of human factor VIII and IX using HIV-1-based lentiviral vectors in mouse liver. Blood 2000; 96:1173-1176.
40. Kang Y, Xic L, Tran D T et al. Persistent expression of factor VIII in vivo following nonprimate lentiviral gene transfer. Blood. 2005; 106:1552-1558.
41. Shi Q, Wilcox D A, Fahs S A et al. Factor VIII ectopically targeted to platelets is therapeutic in hemophilia A with high-titer inhibitory antibodies. J. Clin. Invest 2006; 116:1974-1982.
42. Ohmori T, Mimuro J, Takano K et al. Efficient expression of a transgene in platelets using simian immunodeficiency virus-based vector harboring glycoprotcin Ibalpha promoter: in vivo model for platelet-targeting gene therapy. FASEB J. 2006; 20:1522-1524.
43. Matsui H, Shibata M, Brown B et al. Ex Vivo Gene Therapy for Hemophilia A That Enhances Safe Delivery and Sustained In Vivo FVIII Expression From Lentivirally-engineered Endothelial Progenitors. Stem Cells. 2007.

The invention claimed is:

1. A vector comprising a promoter, wherein the promoter comprises the nucleotide sequence of SEQ ID NO: 3.

2. The vector of claim 1 which is a recombinant adeno-associated virus (rAAV) vector.

3. An isolated host cell comprising the vector of claim 1.

* * * * *